US012048679B2

(12) United States Patent
Machida

(10) Patent No.: US 12,048,679 B2
(45) Date of Patent: Jul. 30, 2024

(54) P53-DESTABILIZING PROTEIN ASSOCIATED WITH PROTO-ONCOGENE STEMNESS AS A THERAPEUTIC TARGET AND INHIBITORS THEREOF FOR USE IN TREATMENT OF CANCER

(71) Applicant: University of Southern California, Los Angeles, CA (US)

(72) Inventor: Keigo Machida, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 19 days.

(21) Appl. No.: 17/716,645

(22) Filed: Apr. 8, 2022

(65) Prior Publication Data

US 2022/0323386 A1 Oct. 13, 2022

Related U.S. Application Data

(60) Provisional application No. 63/172,519, filed on Apr. 8, 2021.

(51) Int. Cl.

*A61K 31/191* (2006.01)
*C12Q 1/6886* (2018.01)
*G01N 33/53* (2006.01)

(52) U.S. Cl.

CPC .......... *A61K 31/191* (2013.01); *C12Q 1/6886* (2013.01); *C12Q 2600/136* (2013.01); *C12Q 2600/158* (2013.01)

(58) Field of Classification Search

CPC ................ A61K 31/191; C12Q 1/6886; C12Q 2600/136; C12Q 2600/158; G01N 33/5011; G01N 33/5044; G01N 33/53; G01N 2500/02; G01N 2500/10

See application file for complete search history.

(56) References Cited

PUBLICATIONS

Latanoprost, 2024, https://www.ncbi.nlm.nih.gov/books/NBK540978/#:~:text=Latanoprost%20is%20a%20United%20States,a%20prostaglandin%20F2%20alpha%20analog.*

Machida et al., TLR4-Dependent Tumor-Initiating Stem Cell-Like Cells (TICs) in Alcohol-Associated Hepatocellular Carcinogenesis, Biological Basis of Alcohol-Induced Cancer, Advances in Experimental Medicine and Biology, 2014, vol. 815, pp. 131-144.

Yu et al., TBC1D15/RAB7-regulated mitochondria-lysosome interaction confers cardioprotection against acute myocardial infarction-induced cardiac injury, Theranostics 2020, 2020, vol. 10(24), pp. 11244-11263.

Chen et al., NANOG Metabolically Reprograms Tumor-Initiating Stem-like Cells through Tumorigenic Changes in Oxidative Phosphorylation and Fatty Acid Metabolism, Cell Metabolism 23, 2016, pp. 206-219.

Choi et al., p53 destabilizing protein skews asymmetric division and enhaces NOTCH activation to direct self-reneval of TICs, Nature Communications, 2020, vol. 11(3084), pp. 1-16.

Feldman et al., The TBC1D15 Oncoprotein Controls Stem Cell Self-Renewal through Destabilization of the Numb-p53 Complex, PLOS One, 2013, vol. 8(2), pp. 1-14.

Ejlerskov et al., IFNB/interferon-B regulates autophagy via a MIR1-TBC1D15-RAB7 pathway, Autophagy, 2020, vol. 16(4), pp. 767-769.

* cited by examiner

*Primary Examiner* — Sun Jae Yoo
(74) *Attorney, Agent, or Firm* — Nixon Peabody LLP

(57) ABSTRACT

The molecular mechanism of the function of TBC1D15 in NOTCH activation and stabilization is associated with maintenance and expansion of tumor-initiating stem-like cells (TICs). We herein demonstrate that TBC1D15 preferentially binds an NUMB isoform and NOTCH1-PEST domain and stabilizes NOTCH1 protein. This interaction enhances phosphorylation of NUMB, taking it away from NUMB-mediated ubiquitin degradation of NOTCH. Thus, TBC1D15 acts as a switch to augment NOTCH signaling in TICs. We also have identified inhibitors of TBC1D15 such as latanoprost acid and a salt thereof, which blocks the NOTCH-TBC1D15 interaction and selectively kills CD133-positive TICs, resulting in a reduction in the tumor size in a patient-derived, hepatocellular carcinoma xenograft model.

13 Claims, 33 Drawing Sheets

Specification includes a Sequence Listing.

Conserved Cdc phosphodegron site

| | | |
|---|---|---|
| NOTCH1 | 2510 | F L T P S P E (SEQ ID NO:2) |
| c-Myc | 56 | L P T P S L S (SEQ ID NO:3) |
| c-Jun | 237 | G E T P S L S (SEQ ID NO:4) |
| Cyclin E | 378 | L L T P S Q S (SEQ ID NO:5) |

P53-DESTABILIZING PROTEIN ASSOCIATED WITH PROTO-ONCOGENE STEMNESS AS A THERAPEUTIC TARGET AND INHIBITORS THEREOF FOR USE IN TREATMENT OF CANCER

CROSS-REFERENCE TO RELATED APPLICATIONS

This application includes a claim of priority under 35 U.S.C. § 119(e) to U.S. provisional patent application no. 63/172,519, filed Apr. 8, 2021, the entirety of which is hereby incorporated by reference.

STATEMENT REGARDING FEDERALLY SPONSORED RESEARCH OR DEVELOPMENT

This invention was made with government support under Grant Nos. AA018857, AA025204, AA025470, DK048522, AA011999, CA014089, and AA012885 awarded by National Institutes of Health. The Government has certain rights in the invention.

REFERENCE TO SEQUENCE LISTING

The Sequence Listing submitted Apr. 8, 2022 as a text file named "SequenceListing-065715-000121US00_ST25" created on Apr. 4, 2022 and having a size of 3,911 bytes, is hereby incorporated by reference.

FIELD OF INVENTION

This invention relates to identification and testing of small molecule inhibitors in treatment of liver cancer and molecular targets associated therewith.

BACKGROUND

Tumor-initiating stem-like cells (TICs) represent a small subset of tumor cells with enhanced self-renewal capability, which play an important role in cancer development, treatment resistance, and cancer recurrence. A majority of cancers arise from highly proliferative expansion of a differentiated progeny derived from TICs that concomitantly maintain a minority population of TICs. TICs are defective in maintaining asymmetric cell division and responsible for chemotherapy/radiation resistance and tumor recurrence. Unlike TICs, stem cells are maintained through asymmetric self-renewing divisions in which one daughter cell commits to a specific fate while the other retains the multipotent characteristics of its parent. The NUMB protein, is an endocytic adaptor protein, which acts as a tumor suppressor by inhibiting the ubiquitin ligase HDM2 (human homolog of murine double minute 2), thereby preventing the destruction of p53. It preserves the intrinsic cellular asymmetry and functions as a vital barrier against unchecked expansion of tumor-associated stem cells as seen in TICs. But how TICs overcome this control on asymmetric division to cause cancer is unknown. Accurately identifying a TIC population has been challenging, which also hinders the development of TIC-targeted therapeutics.

NUMB is a conserved endocytic adaptor protein expressed in both developing and adult tissues. NUMB is vital for mammalian development, and failure to express NUMB (or the absence of Numb function) results in severe defects in nervous system development with associated embryonic lethality. NUMB protein has an amino-terminal phospho-tyrosine-binding (PTB) domain and a carboxy-terminal proline-rich region (PRR) containing two aspartic acid-proline-phenylalanine (DPF) motifs and an asparagine-proline-phenylalanine (NPF) motif. These tripeptide motifs are important for NUMB binding to the clathrin adaptor complex AP-2 complex and to Eps15 homology (EH) domain-containing proteins. EH-containing and EH-binding proteins establish a complex network of interactions within the cell that regulates internalization (or endocytosis) and trafficking processes. Mammalian NUMB genes are alternatively spliced to produce multiple (six) functionally specific isoforms, resulting from the presence or absence of three coding exons (exon 6, exon 10, and exon 12). The most abundantly expressed isoforms differ by the inclusion of two coding exons: exon 3 (E3), corresponding to an 11-amino-acid region within the PTB domain, and exon 9 (E9), corresponding to a 49-amino-acid region within the central region of the protein. Evidence indicates that differential expression and function of the Numb isoforms during development is regulated by alternative splicing. The Numb 1/3 isoforms are predominantly expressed in progenitor tissues, whereas the 2/4 isoforms are highly expressed in adult tissues. Changes in NUMB isoforms also appear to modify the function of NUMB as an inhibitor of the NOTCH signaling pathway. Activation of the NOTCH pathway in both lung and breast adenocarcinoma has been linked to global downregulation of NUMBs at the protein level. Recent studies indicate that Numb AS is mis-regulated in cancer. This regulation of NUMB expression is associated with altered NUMB isoform expression and with subsequent effects on NOTCH pathway activation, thus implying a functional role for NUMB alternative splicing downstream of the oncogenic signaling pathway.

NOTCH signaling is important for inducing tumor progression in many cancers, notably in liver cancer, breast cancer, and others. Targeting and inhibition of NOTCH signaling is complicated in cancers because NOTCH has multiple important tissue-specific roles in the homeostasis of many organ tissues. Deregulation of the NOTCH signaling pathway is involved in maintenance and survival of cancer stem cells (CSCs), which likely underlies the observed resistance to chemotherapy.

Prominin 1 (CD133, encoded by the PROM 1 gene) is a marker of TICs in various carcinomas and used as a factor to define cancer stemness and disease severity in patients. Studies have shown that PROM 1(+) cells accumulate in the mouse liver injury model and in the livers of patients with alcoholic hepatitis.

A unique NOTCH/NUMB-interacting protein, TBC1D15 (Tre2/Bub2/Cdc16 domain family member 15, or Tre-2/Bub2/Cdc16 domain family member 15, or Tre2-Bub2-Cdc16 domain family member 15) is overexpressed and contributes to p53 degradation in PROM 1(+) liver TICs. There remains a great need to elucidate TBC1D15-mediated oncogenesis or tumorigenesis and importantly, identify therapeutic agents to target this pathway in the treatment of related cancers.

Further complexity in the NOTCH pathway has been studied through immunoaffinity purification of TBC1D15-interacting proteins followed by liquid chromatography-tandem mass spectrometry (LC-MS/MS). TBC1D15 interacts with all NOTCH isotypes in addition to NUMB to activate the NOTCH signaling pathway. Thus, Nanog and hepatic TICs can induce self-renewal.

TBC1D15 has additional functions including its role as a mitochondrial Rab GTPase-activating protein (Rab-GAP) and is known to affect processes such as autophagy and/or mitophagy in other organisms. In certain types of cancers, TICs have a distinct metabolism relying on the mitochondrial respiration for survival. One study reported that NOTCH1 might also regulate the transcription of mitochondrial proteins consistent with increased mitochondrial respiration.

Yet a precise mechanistic involvement by which TBC1D15 regulates the NOTCH1 signaling pathway is still unclear. Compounds remains to be identified for targeting the NOTCH1 domain that binds TBC1D15 or targeting the TBC1D15, as a potential therapeutic modality for CD133$^{+}$ TIC targets.

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

SUMMARY OF THE INVENTION

Methods for treating a subject with a tumor or suspected of having a tumor, comprising administering an effective amount of a composition comprising an inhibitor of Tre2-Bub2-Cdc16 domain family member 15 (TBC1D15) and a pharmaceutically acceptable excipient to the subject, wherein the inhibitor of TBC1D15 inhibits binding between TBC1D15 and neurogenic locus notch homolog protein 1 (NOTCH1), or wherein the inhibitor of TBC1D15 inhibits expression of TBC1D15 gene.

In some embodiments, the inhibitor of TBC1D15 is a small molecule which inhibits the binding between TBC1D15 and NOTCH1. In some embodiments, the inhibitor of TBC1D15 blocks the binding between the TBC1D15 and a Ser-Thr-rich (STR) domain within a NOTCH-intracellular domain (NICD) of the NOTCH1, or the inhibitor of TBC1D15 blocks the binding between the TBC1D15 and a PEST domain within the NICD of the NOTCH1.

In further embodiments, the inhibitor of TBC1D15 also induces toxicity selectively to a CD133$^{+}$ tumor cell or a CD133$^{+}$ tumor-initiating stem-like cell (TIC) over a CD133$^{-}$ TIC or a normal cell, and/or reduces gene expression of NOTCH and/or NANOG in a tumor cell or a TIC.

Exemplary inhibitors of TBC1D15 that inhibits binding between TBC1D15 and NOTCH1 include but are not limited to a prostaglandin analogue, such as latanoprost or latanoprost acid, or a pharmacologically active metabolite, salt, solvate or racemate of prostaglandin analogue.

In other embodiments, the inhibitor of TBC1D15 inhibits expression of the TBC1D15 gene, and the inhibitor of TBC1D15 can be, but is not limited to, a guide RNA that targets the TBC1D15 gene for nuclease cleavage.

The methods can be used to treat a subject with a cancer comprising hepatocellular carcinoma, liver cancer, lung cancer, breast cancer, ovary cancer, or a combination thereof, or having a chronic inflammation (such as liver inflammation, hepatitis) and being at risk of developing a cancer (such as liver cancer).

In some embodiments, the subject in the methods is a human or a mammal detected with an increased expression level of TBC1D15 protein or gene in a tumor sample, compared to that in a non-tumor sample, or the increased expression level in a tissue suspected of having a tumor of the subject, compared to that in a matched tissue from a subject free of the tumor. In some embodiments, the subject is one whose tumor sample is positive for CD133 and CD49f, or one detected with a presence of CD133$^{+}$ and CD49f$^{+}$ TICs. In yet another embodiment, the subject has an increased phosphorylation of NUMB isoform 5 in CD133$^{+}$ TICs or CD133$^{+}$ tumor cells, compared to that in CD133$^{-}$ TICs or CD133$^{-}$ tumor cells, prior to the administration of the inhibitor of TBC1D15; and/or prior to the administration, the subject has an increased number of mitochondria in CD133$^{+}$ TICs or CD133$^{+}$ tumor cells, compared to that in CD133$^{-}$ TICs or CD133$^{-}$ tumor cells.

In some embodiments, the treatment methods further include detecting an increased p53 protein level expression, a decreased NOTCH1 expression level, a decreased NANOG expression level, or a combination thereof in a tumor sample of the subject following the administration, compared to respective level before the administration.

Methods are also provided for identifying an agent for use in treating a subject with a cancer or inhibiting tumor growth, wherein the agent inhibits binding between TBC1D15 and NOTCH1/NOTCH3.

BRIEF DESCRIPTION OF THE FIGURES

Exemplary embodiments are illustrated in referenced figures. It is intended that the embodiments and figures disclosed herein are to be considered illustrative rather than restrictive.

(1A) Expression of TBC1D15 in various human tissues. Distribution of log 10 (gene-level transcripts per kilobase million, TPM) of TBC1D15 RNA-seq expression levels in 21 human tissues were downloaded from the GTEx portal v8.

(1B) Kaplan-Meier analysis of liver, lung, breast, and ovary cancer patients with primary tumors expressing high or low levels of TBC1D15. p-value from stratified Cox proportional hazards model.

(1C) Representative immunohistochemistry images for localized TBC1D15, NOTCH1, and NUMB in human normal liver vs hepatocellular carcinoma tissues. Scale bars, 50 μm. Insets represent 10× magnification of the image shown at 40×.

(1D) Co-IP-Western blot analysis for identifying domains involved in interaction of NICD with TBC1D15 in CD133(+) TICs.

(1E) Co-IP-Western blot analysis for identified interaction with domain of STR and Pin1 in CD133(+) TICs with or without Pin1-overexpressing.

Figure 1A:
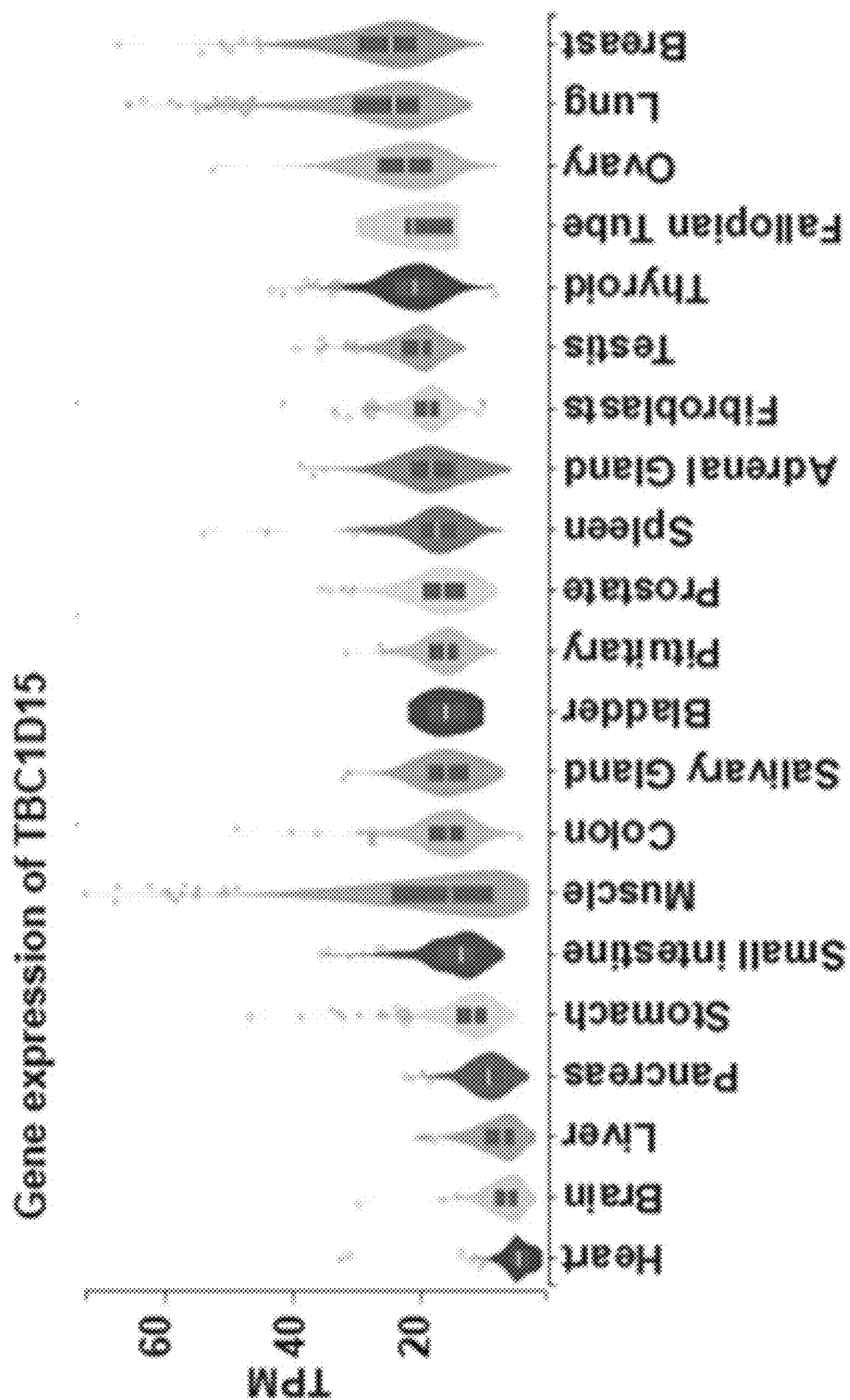
FIGS. 1A-1E depict that TBC1D15 binds to human NOTCH1-PEST domain.
Figure 1B:
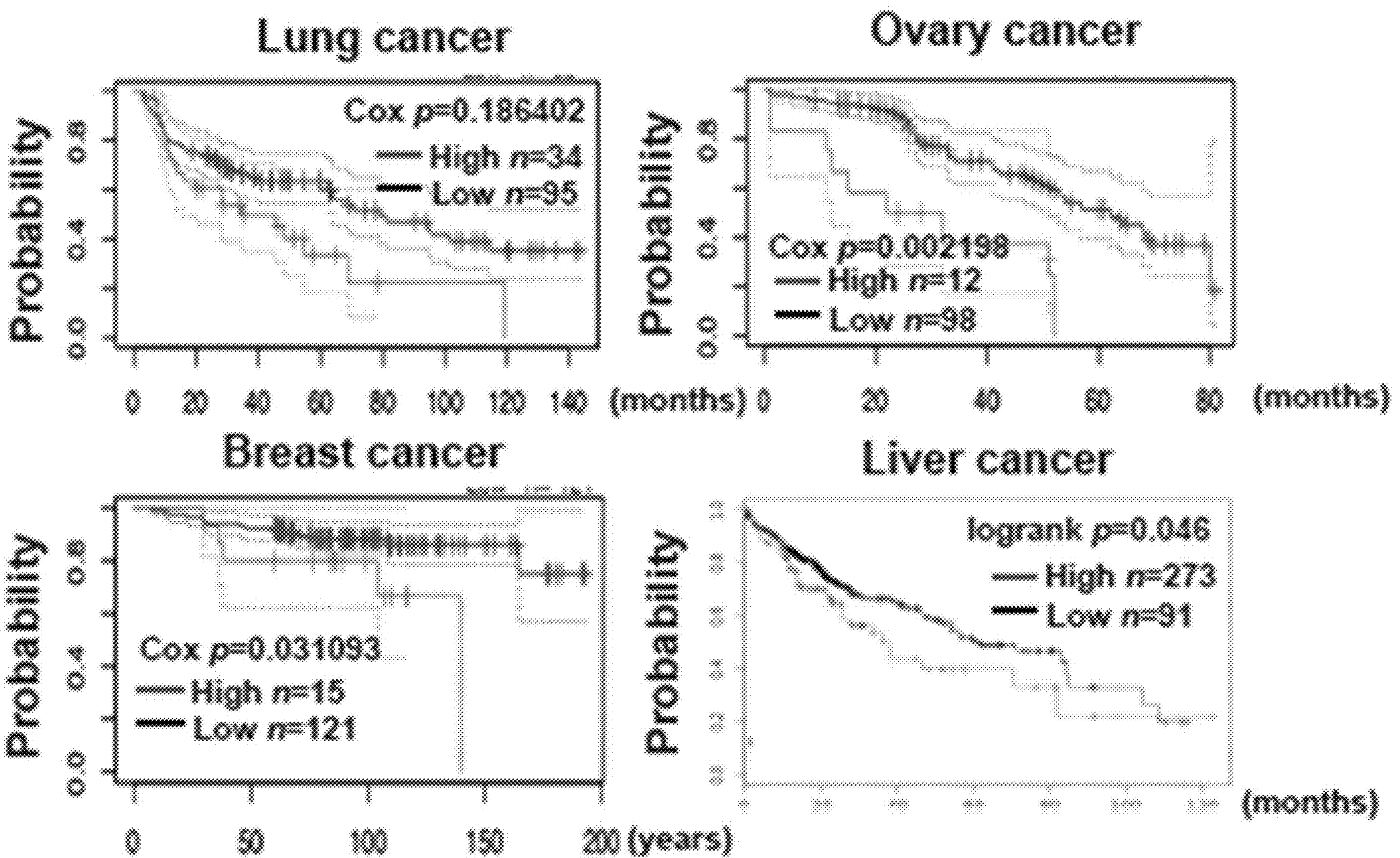
Figure 1C:
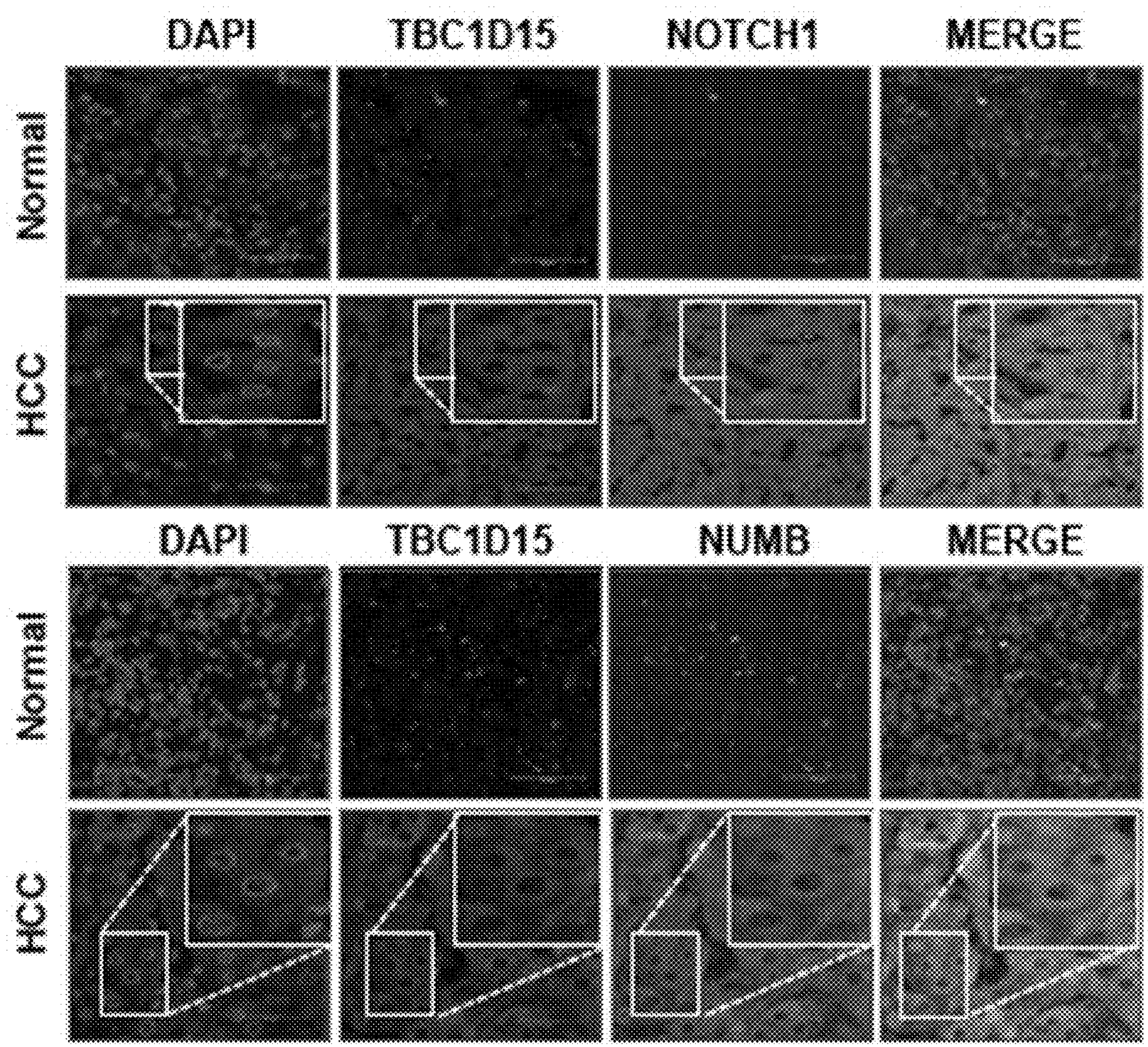
Figure 1D:
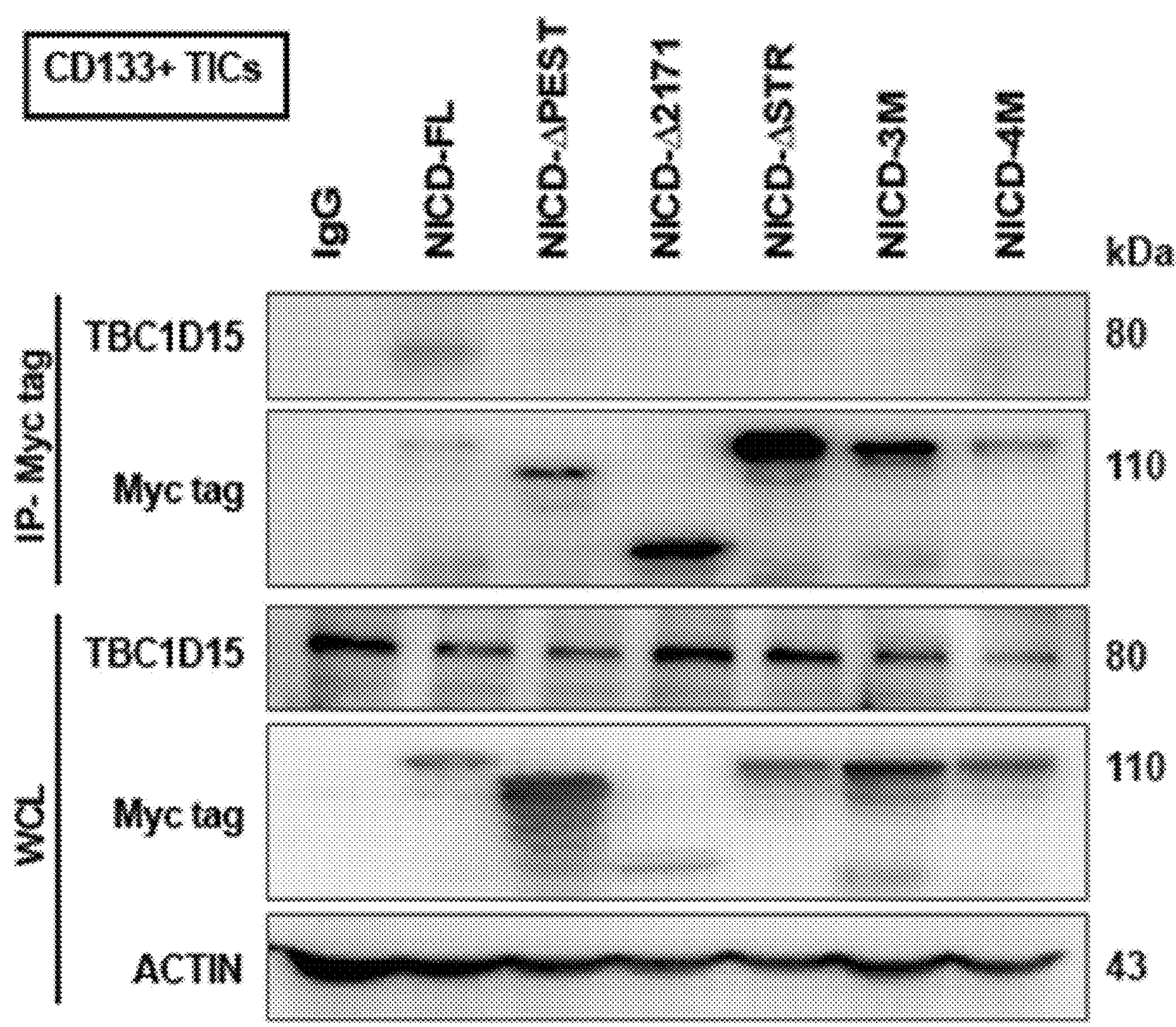
Figure 1E:
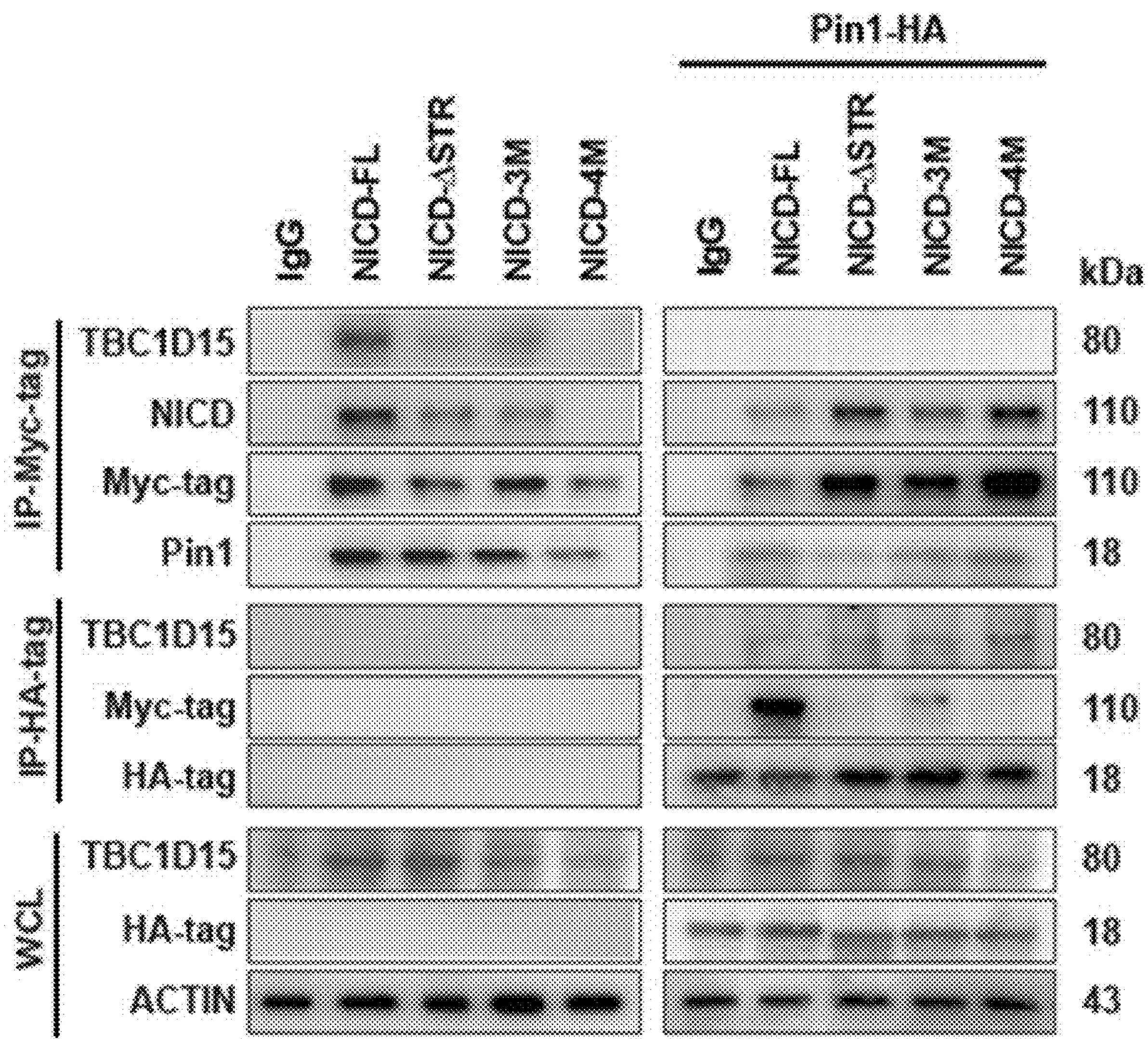
Figure 1F:
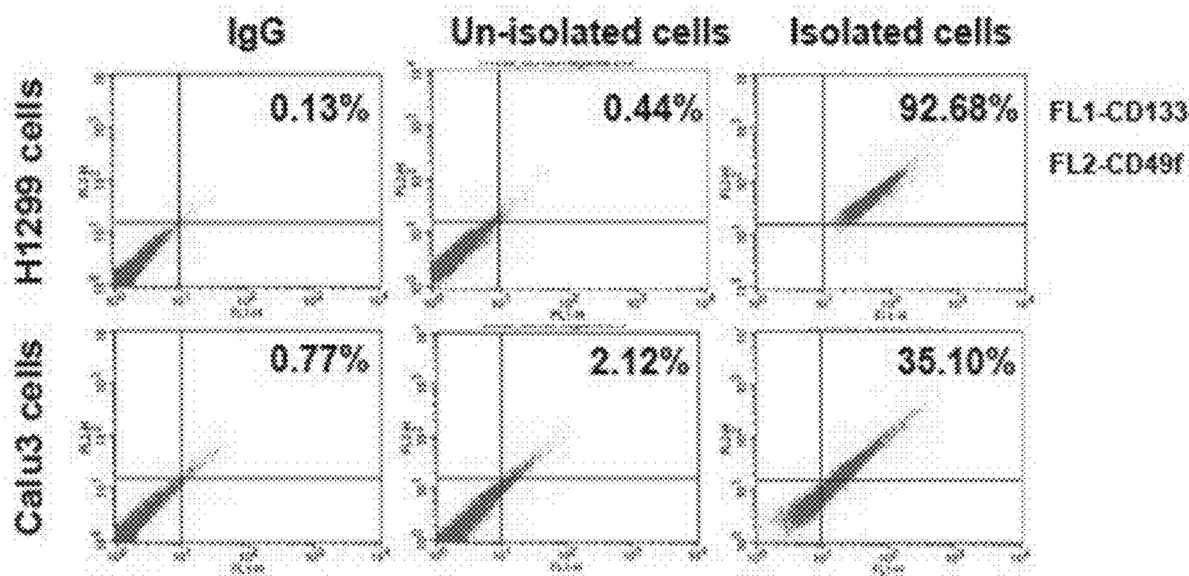
Figure 1G:
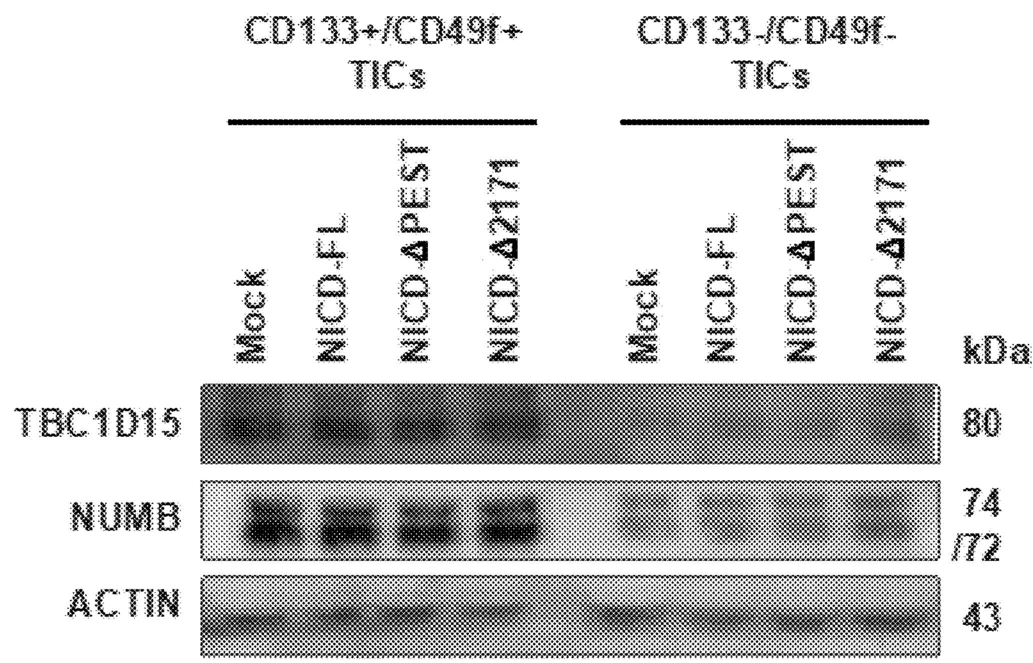

FIGS. 1F and 1G depict the CD133/CD49f TICs isolated in Lung cancer cell lines.

(1F) FACS analysis of CD133+/CD49f+ TICs from isolation of CD133/CD49f TICs from H1299 and Calu3 cells using the affinity magnetic-microbead kit.

(1G) Western blotting for TBC1D15, NUMB, and ACTIN in isolated CD133+/CD49f+ or CD133−/CD49f− TICs.

FIGS. 1H-1L depict that the NICD C-terminal PEST domain interacts with TBC1D15 in CD133-positive TICs.

(1H) Co-expression analysis of NOTCHs and TBC1D15. Genes that co-expressed with NOTCHs and TBC1D15 revealed by the Oncomine database. Range of the of mRNA expression values is represented by the color palette. Red color represents the higher expression and blue represents the lower expression of the mRNA.

(1I) Schematic illustration of NICD domain deletion mutant constructs.

(1J) Co-IP-Western blot analysis for identified interaction domains of NICD and TBC1D15 in CD133-positive TICs with or without TBC1D15-overexpressing.

(1K) Co-IP-Western blot analysis for identified interaction domains of NICD and TBC1D15 in CD133-negative TICs with or without TBC1D15-overexpressing.

(1L) Left panel, Western blot analysis for knockdown of TBC1D15 expression in shTBC1D15 lentiviral transducing-CD133-positive TICs. Middle panel, Co-IP-Western blot analysis for confirmed interaction PEST domains of NICD and TBC1D15 in shTBC1D15 lentiviral transducing-CD133-positive TICs. Right panel, Co-IP-Western blot analysis for confirmed interaction PEST domains of NICD and TBC1D15 in shTBC1D15 lentiviral transducing-CD133-positive TICs with TBC1D15-overexpressing.

Figure 1H:
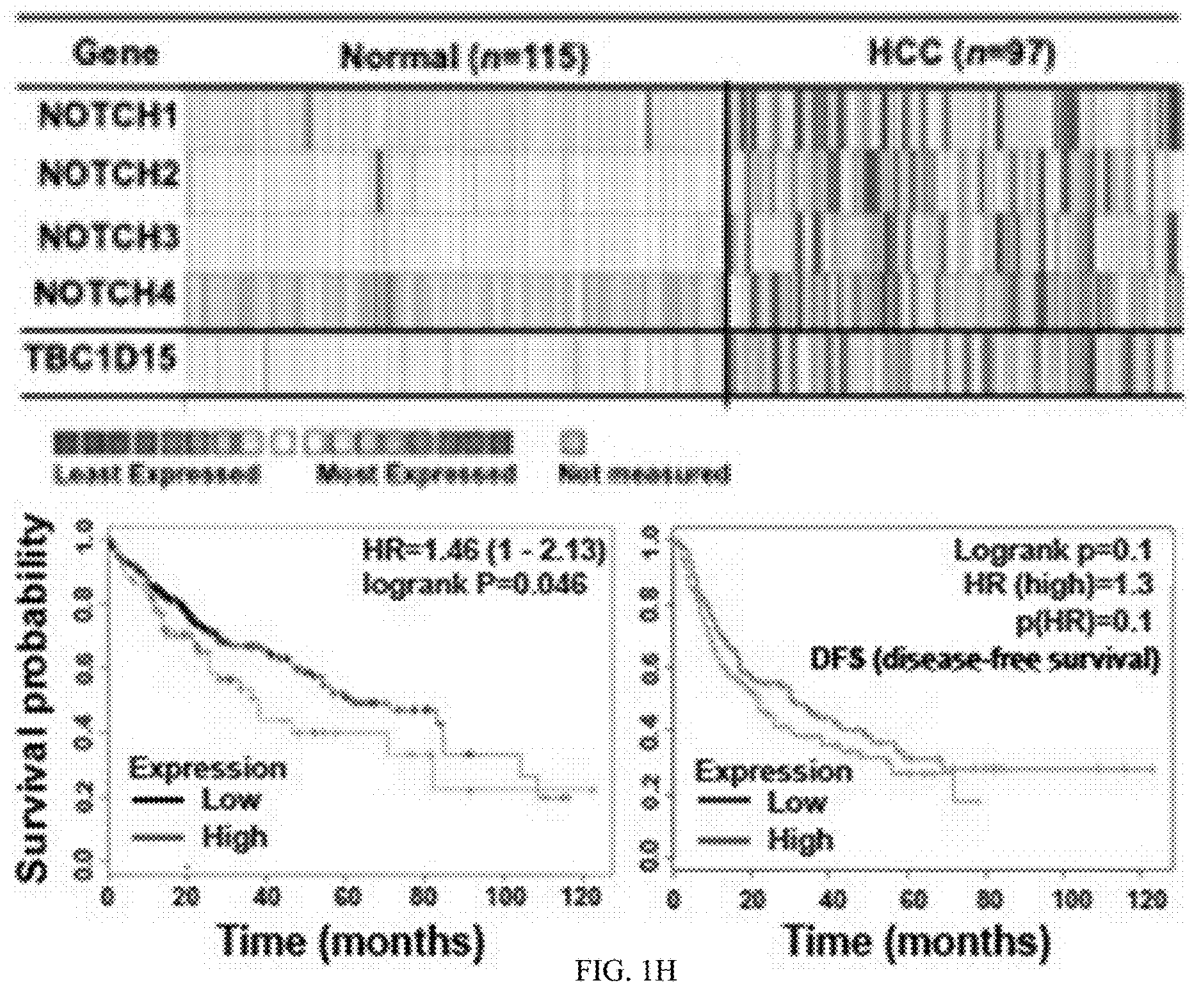
Figure 1I:
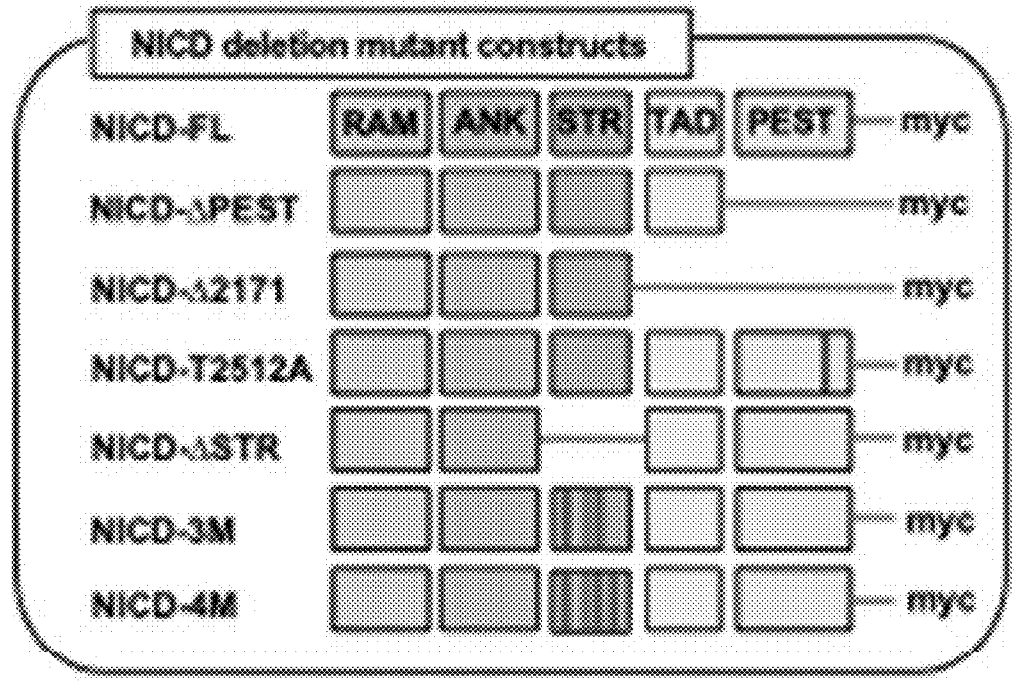
Figure 1J:
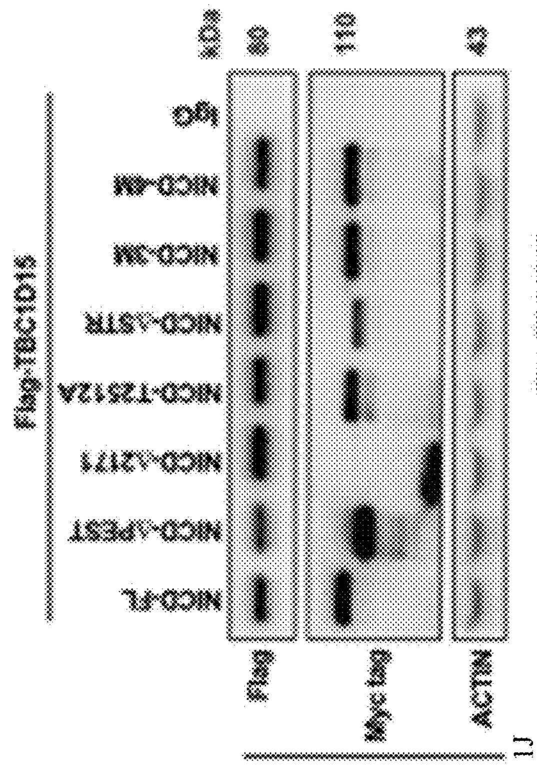
Figure 1J:
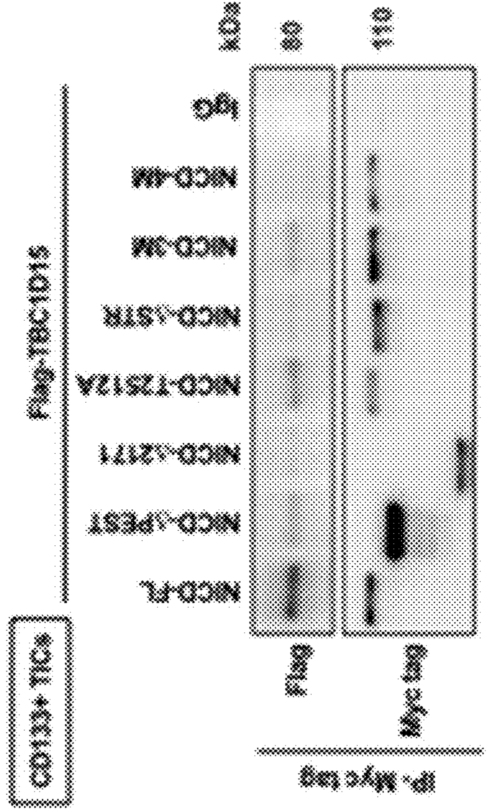
Figure 1K:
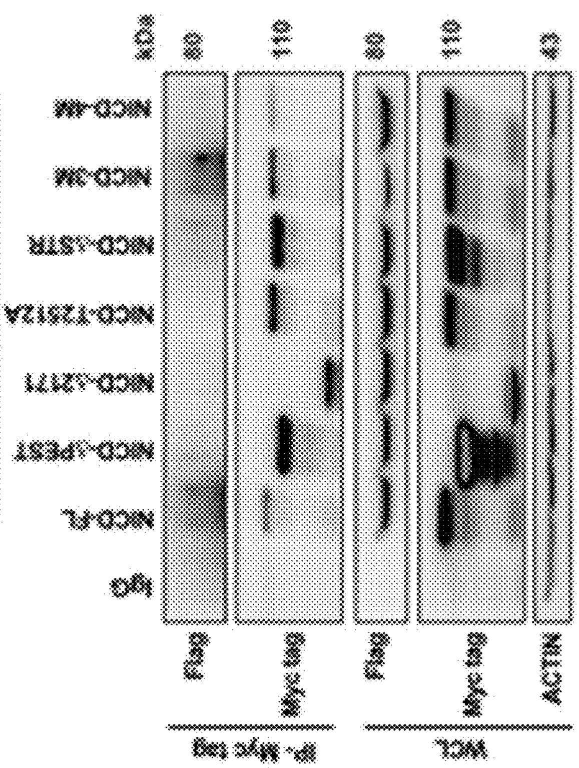
Figure 1K:
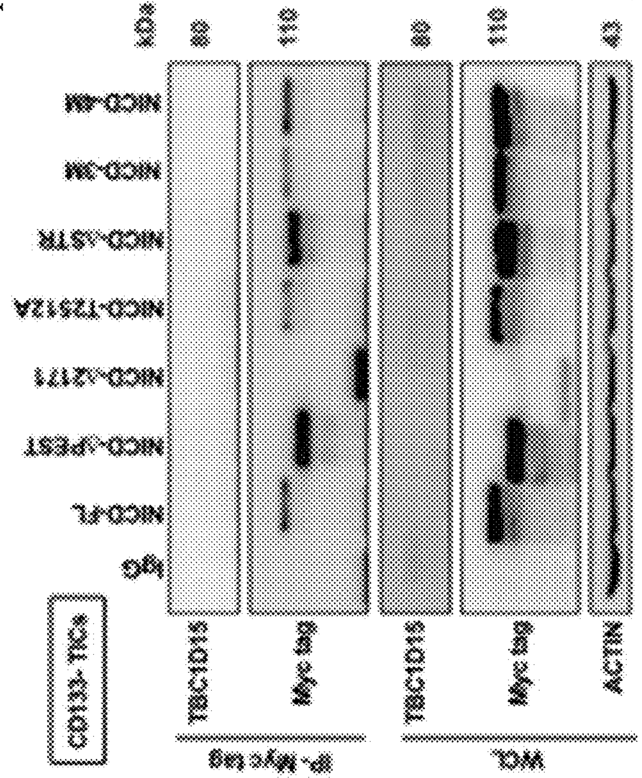
Figure 1L:
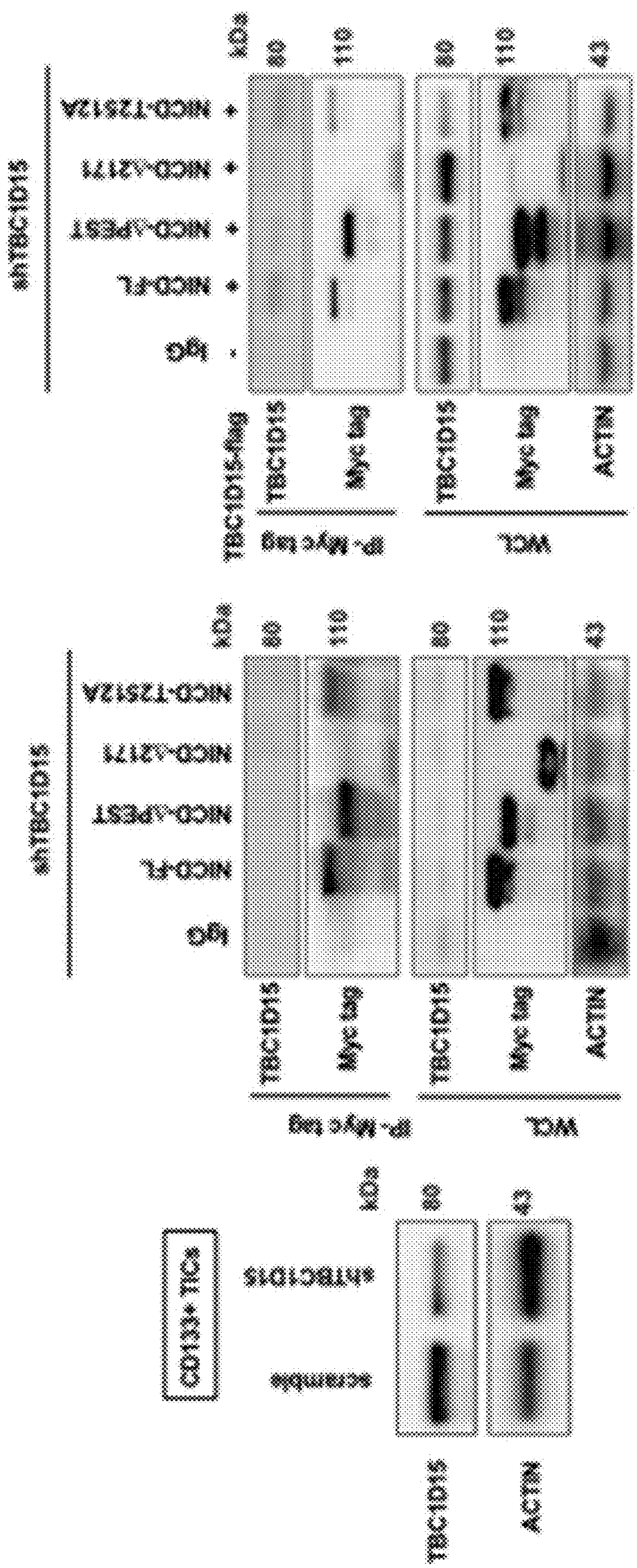
Figure 1M:
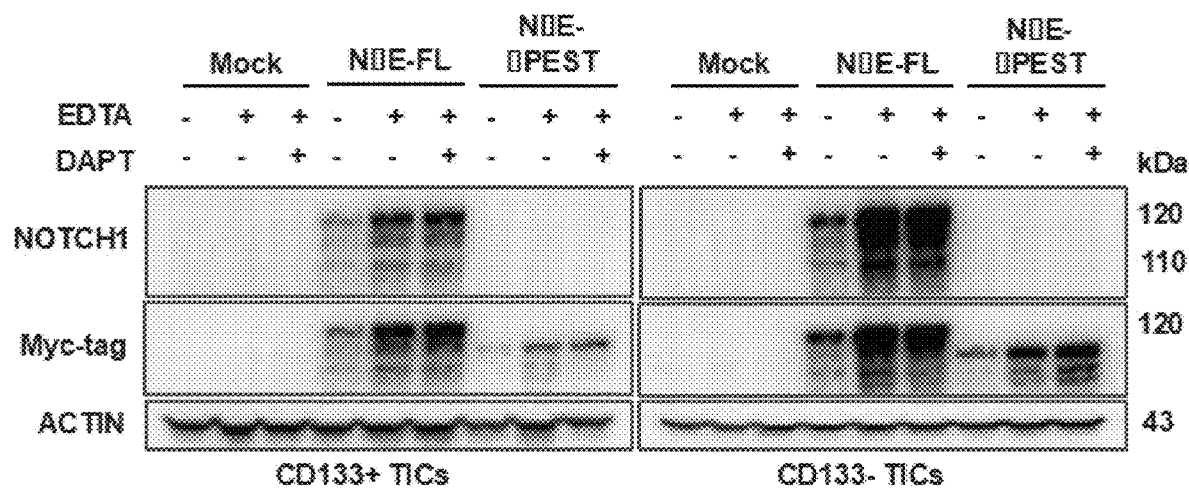
Figure 1N:
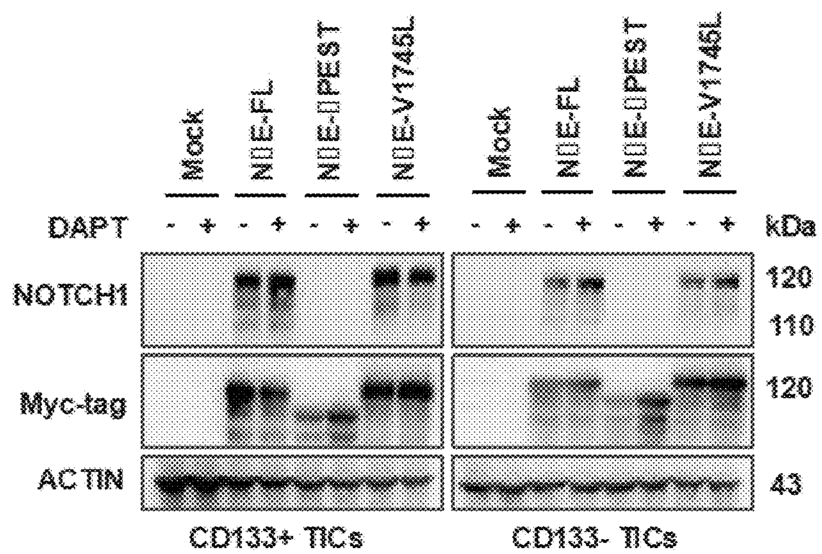

FIGS. 1M and 1N depict that TBC1D15 affects NOTCH1 processing.

(1M) Western blot analysis for expression of endogenous NOTCH1 and N1ΔE-myc tag in CD133-positive and negative TICs, transfected with N1ΔE-FL and N1ΔE-ΔPEST and treated with vehicle or 20 μM DAPT (for 4 h), and 5 mM EDTA (for 20 min).

(1N) Western blot analysis for endogenous NOTCH1 and N1ΔE-myc tag in CD133-positive and negative TICs, transfected with N1ΔE-FL, N1ΔE-ΔPEST, and N1ΔE-V1745L (inhibition of gamma-secretase cleavage) and treated with vehicle or 20 μM DAPT.

Figure 1O:
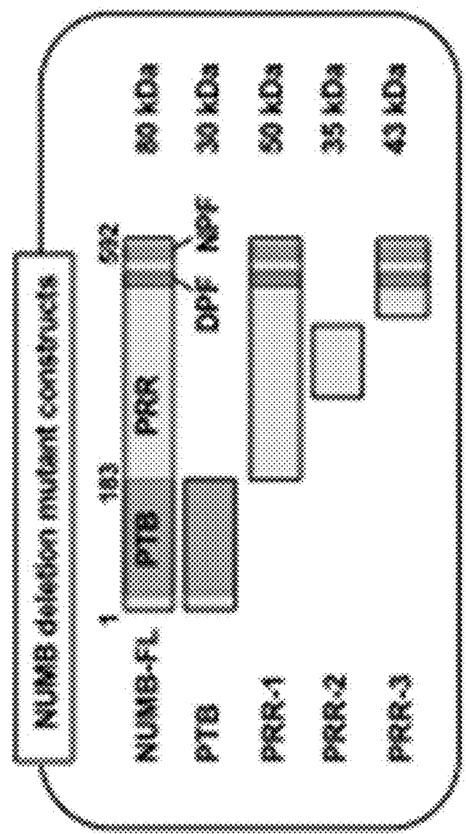
Figure 1P:
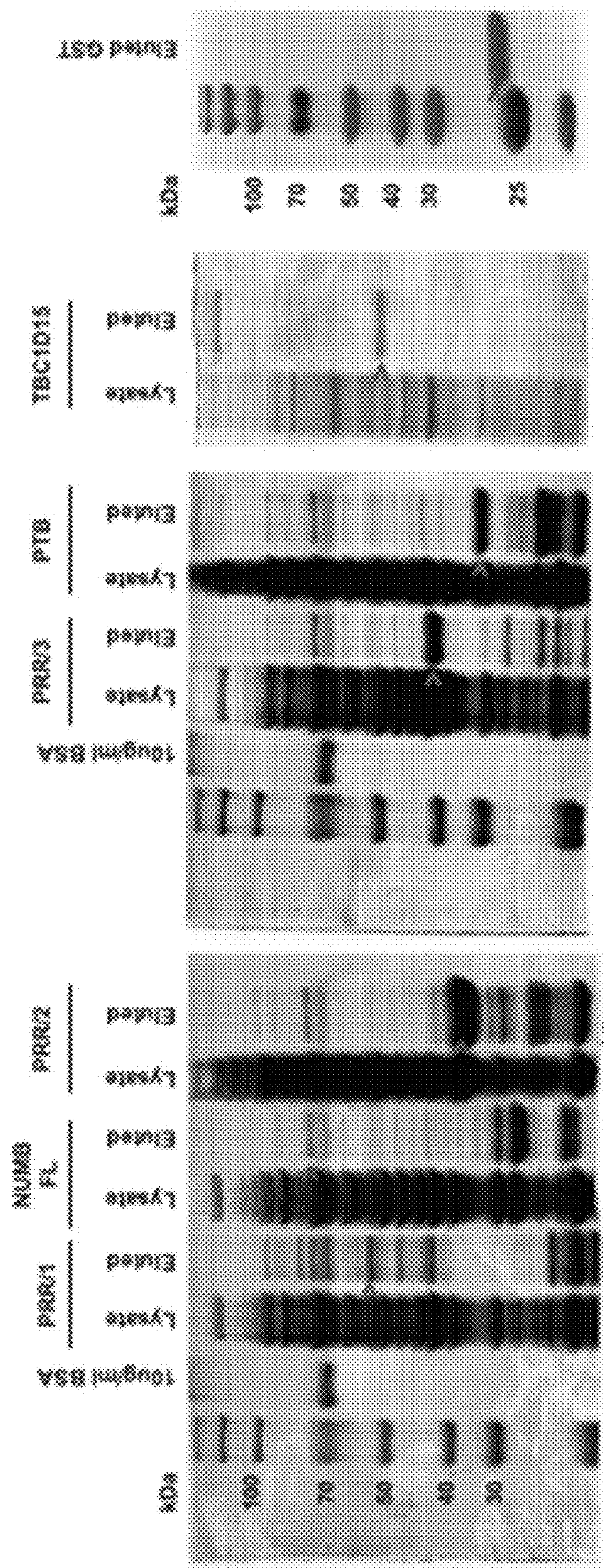
Figure 1Q:
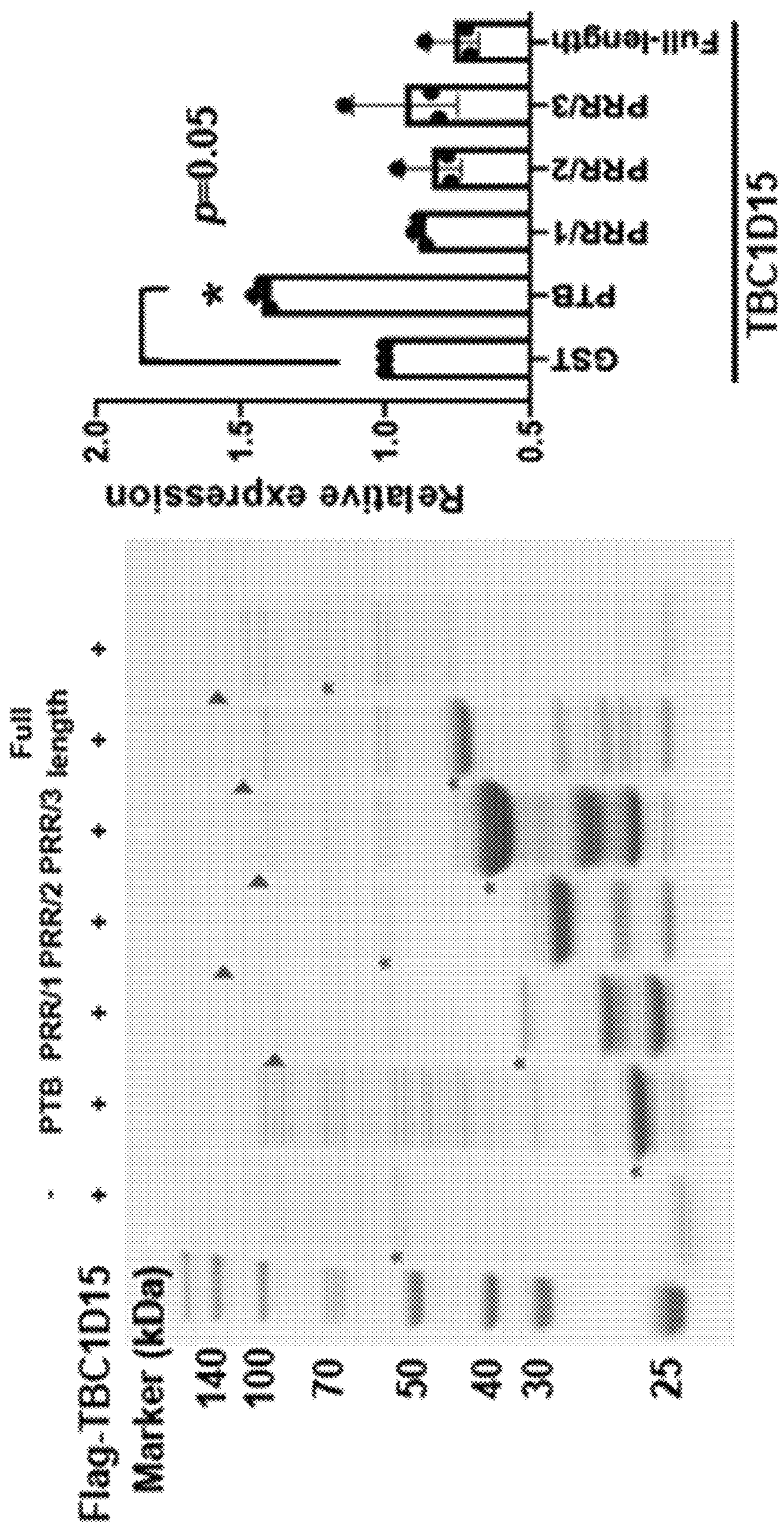

FIGS. 1O-1Q depict the NUMB PTB domain interaction with TBC1D15.

(1O) Schematic illustration of NUMB domain deletion mutant constructs.

(1P) SDS-PAGE analyses from the purification of GST-tag NUMB domain constructs, and with 10 mM imidazole in the sample. The gels were stained with Coomassie blue.

(1Q) Left panel, cell-free in vitro binding assay for identified interaction domain of NUMB and TBC1D15. Right panel, data from Cell-free in vitro binding assay were used for this bar graph. The densitometry quantification was done using the NIH image J program as described in methods.

FIGS. 2A-2F depict that TBC1D15 interacts with NUMB isoform 5.

(2A) Co-IP-Western blot analysis for investigated NUMB phosphorylation and expression in TBC1D15 KD of CD133(+) TICs and TBC1D15-overexpressing of CD133(−) TICs.

(2B) Cell-free in vitro binding assay for identified interaction domain of NUMB full length, NUMB isoform 5, 6 and TBC1D15. Ponceau staining showed loading control.

(2C) Co-IP-Western blot analysis for identified interaction NUMB isoforms and TBC1D15 in indicated cells with NUMB full length or isoform 5, 6.

(2D) Co-IP Western blot analysis for interacted with TBC1D15 (Flag-tag), NUMB full-length and isoform 5 (GFP-tag), and PEST domain of NICD (MYC-tag) in CD133(+) TICs.

(2E) Confocal images of localization in TICs with TBC1D15 (endogenous, third column from the left) and GFP-NUMBs (second column from the left) and DAPI (first column from the left). Scale bars: 7.2 μm.

(2F) Confocal images of localization in TICs with TOM20 (outer membrane of mitochondria marker, third column from the left), GFP-NUMB (second column from the left) and DAPI (first column from the left). Scale bar 6.14 μm.

Figure 2A:
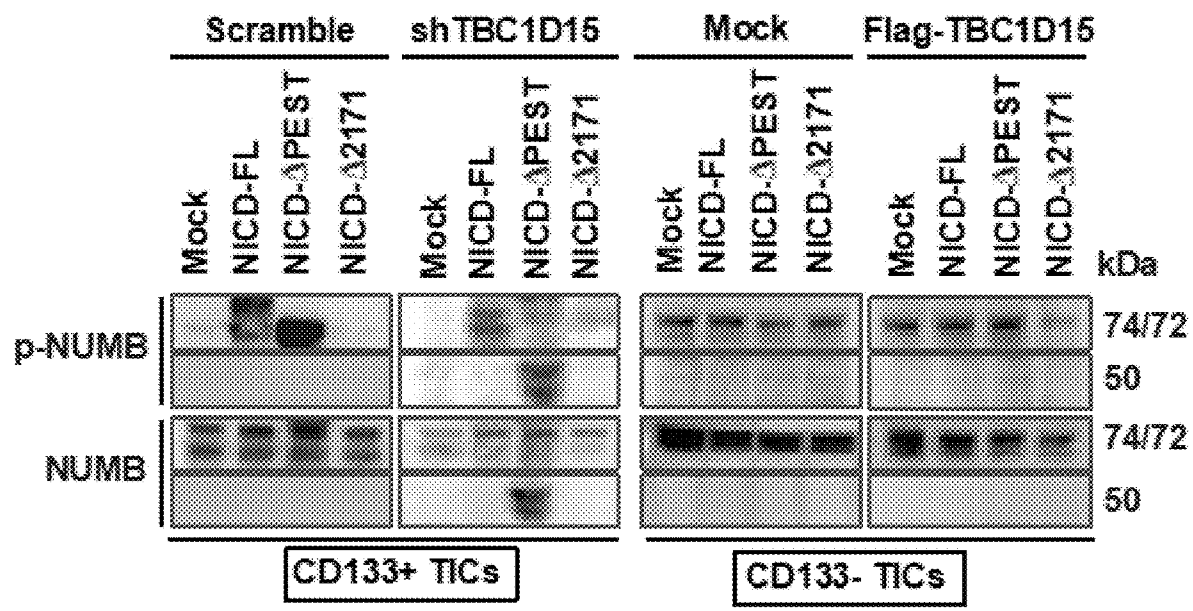
Figure 2B:
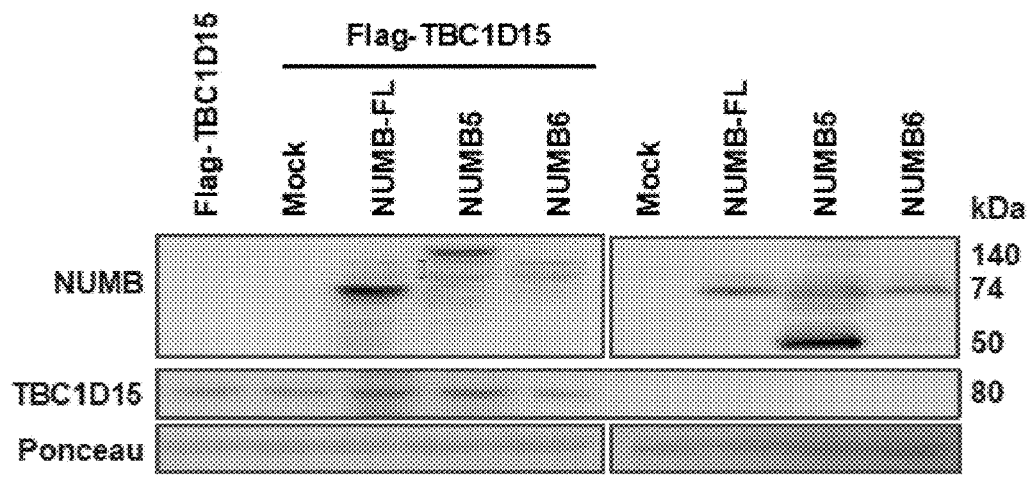
Figure 2C:
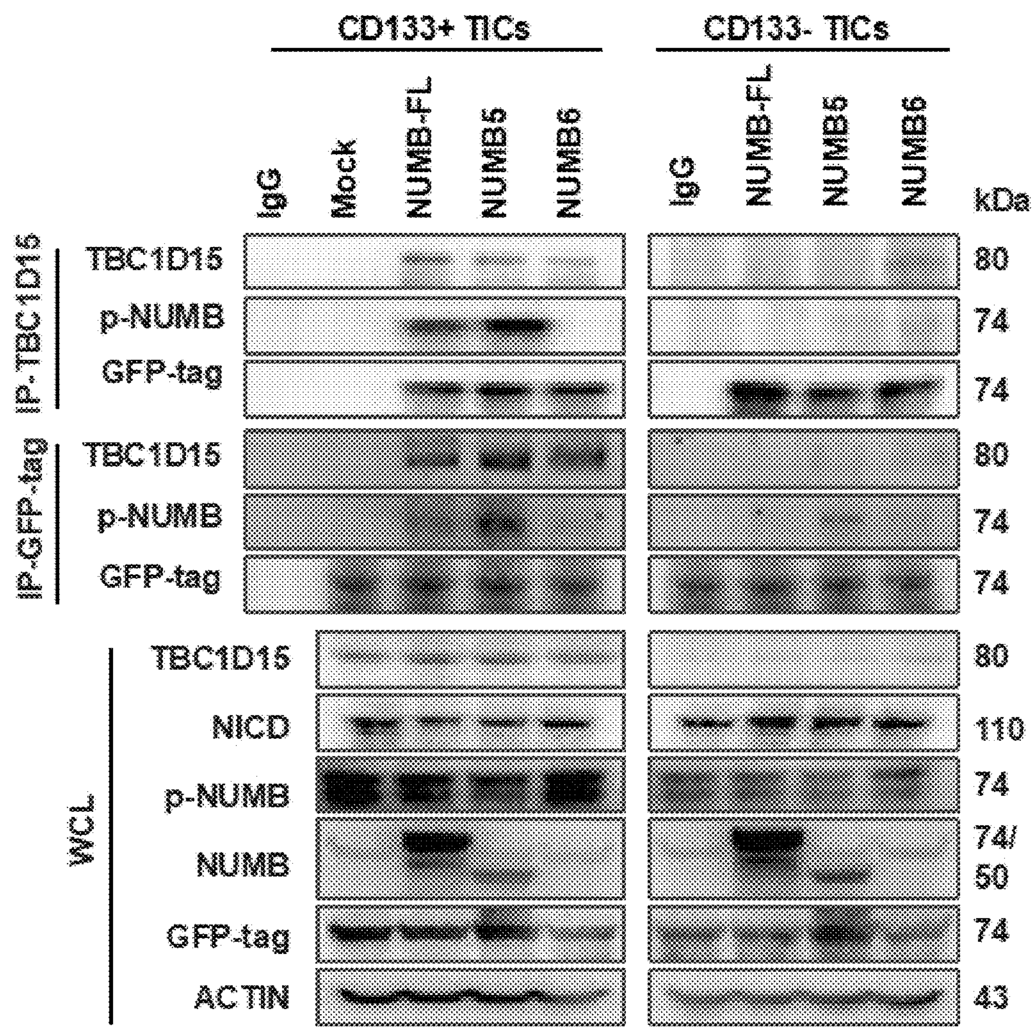
Figure 2D:
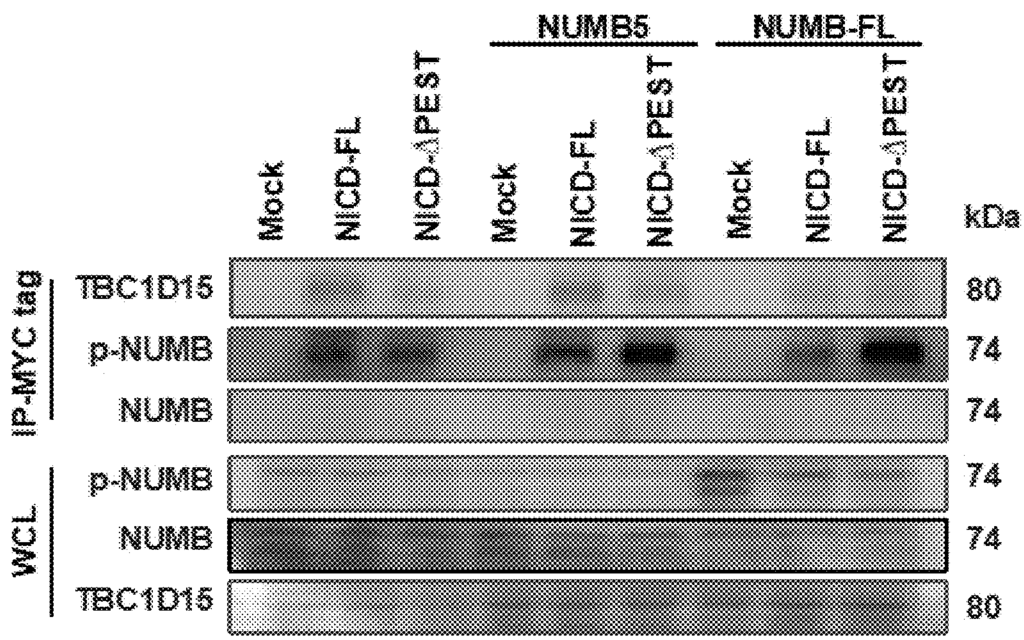
Figure 2E:
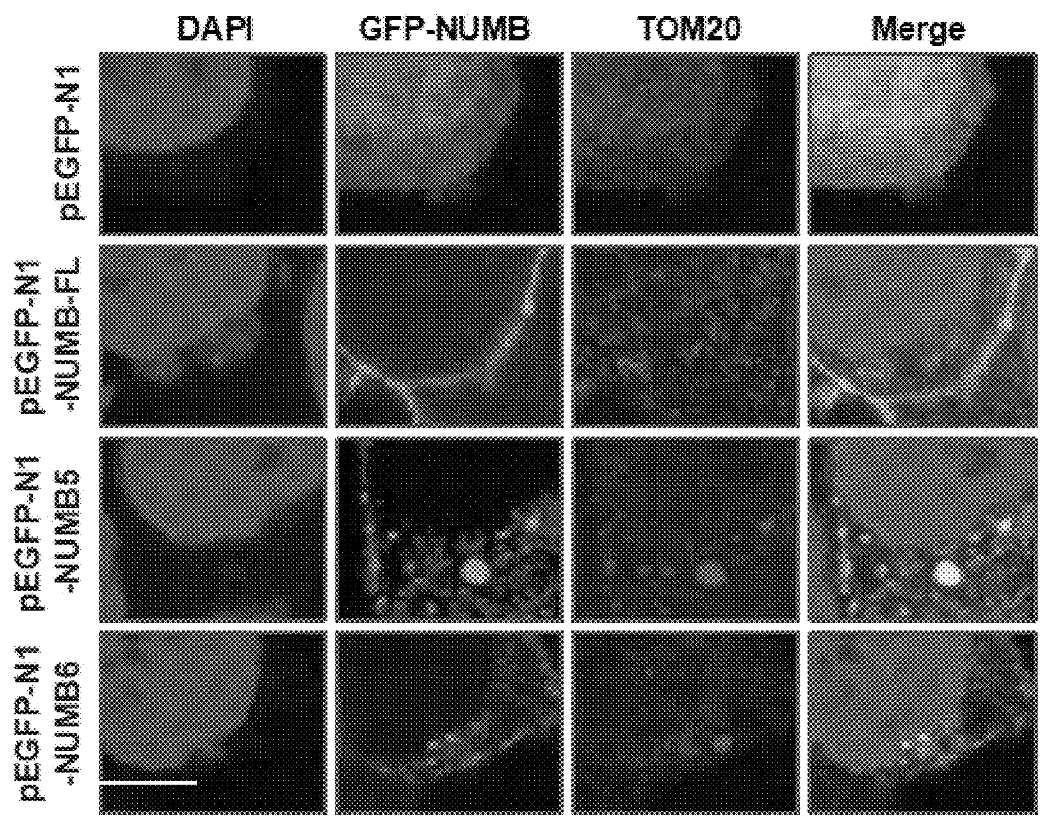
Figure 2F:
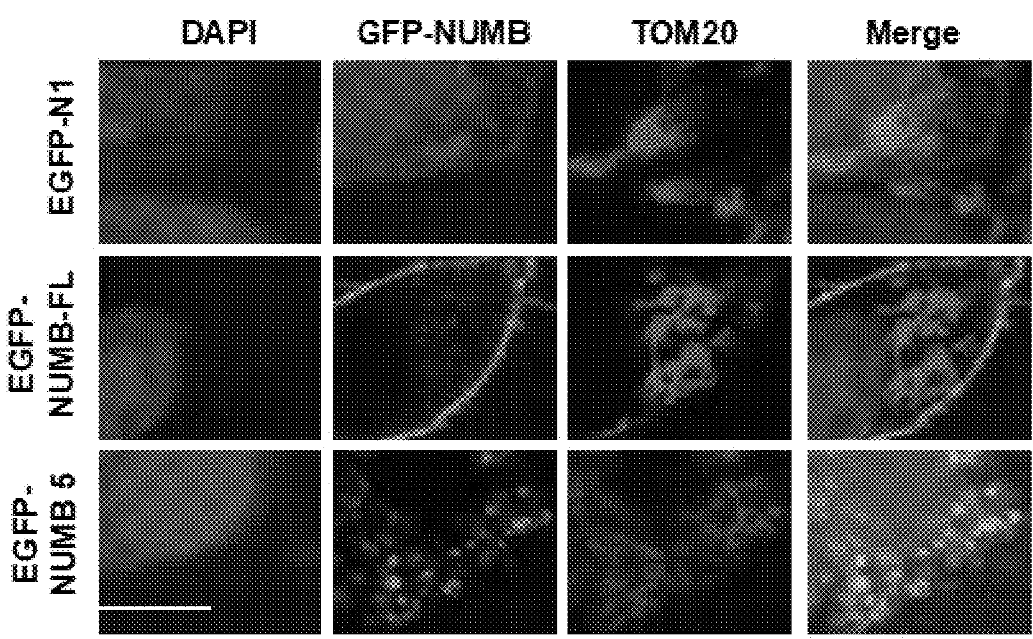
Figure 2G:
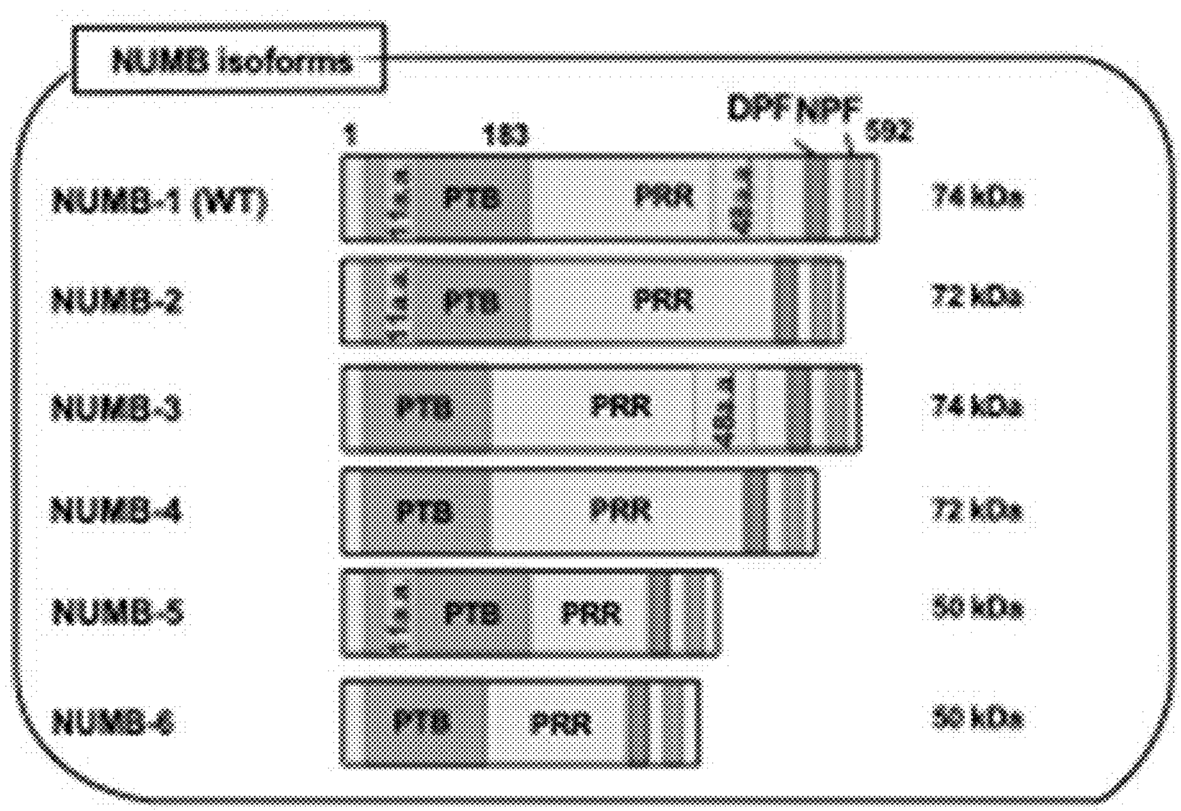
Figure 2G:
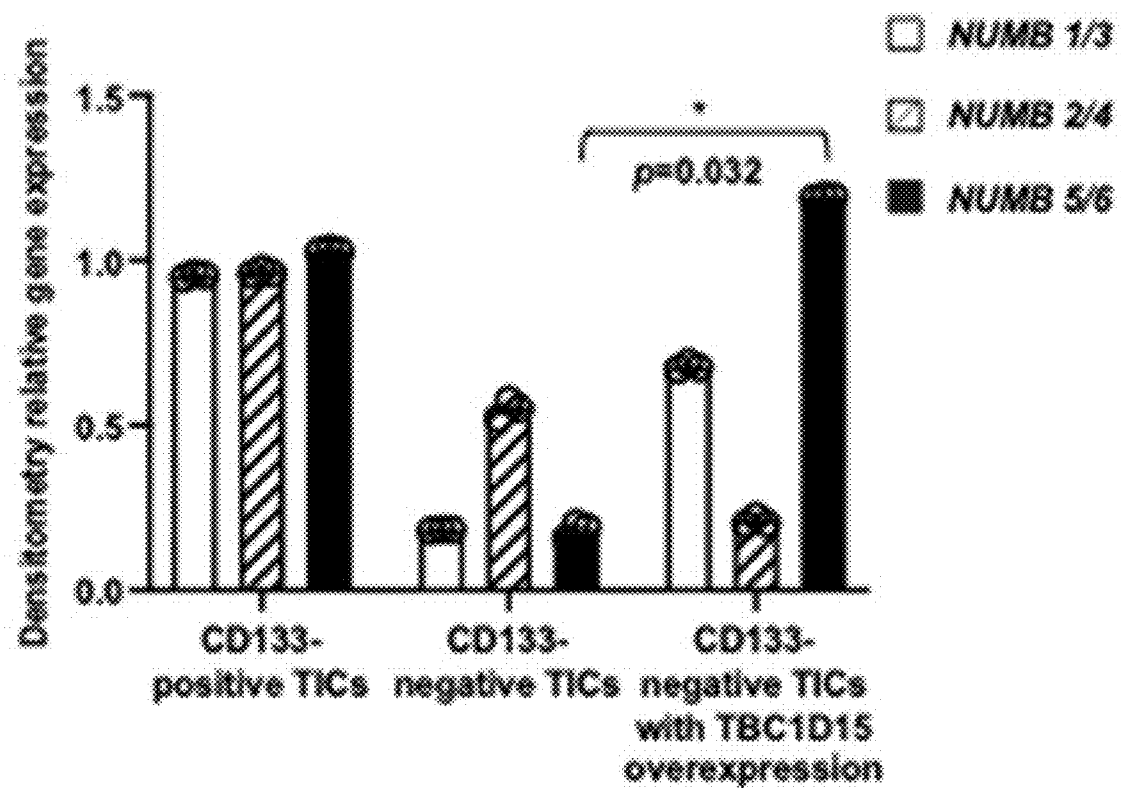

FIG. 2G, in the left panel, is a schematic illustration of NUMB isoforms constructs and protein sizes; and in the right panel, depicts Semi-qPCR analysis of NUMB isoforms expression in indicated cells. Graph data from agarose images of semi-qPCR analysis were used for this bar graph. The densitometry quantification was done using the NIH image J program.

Figure 2H:
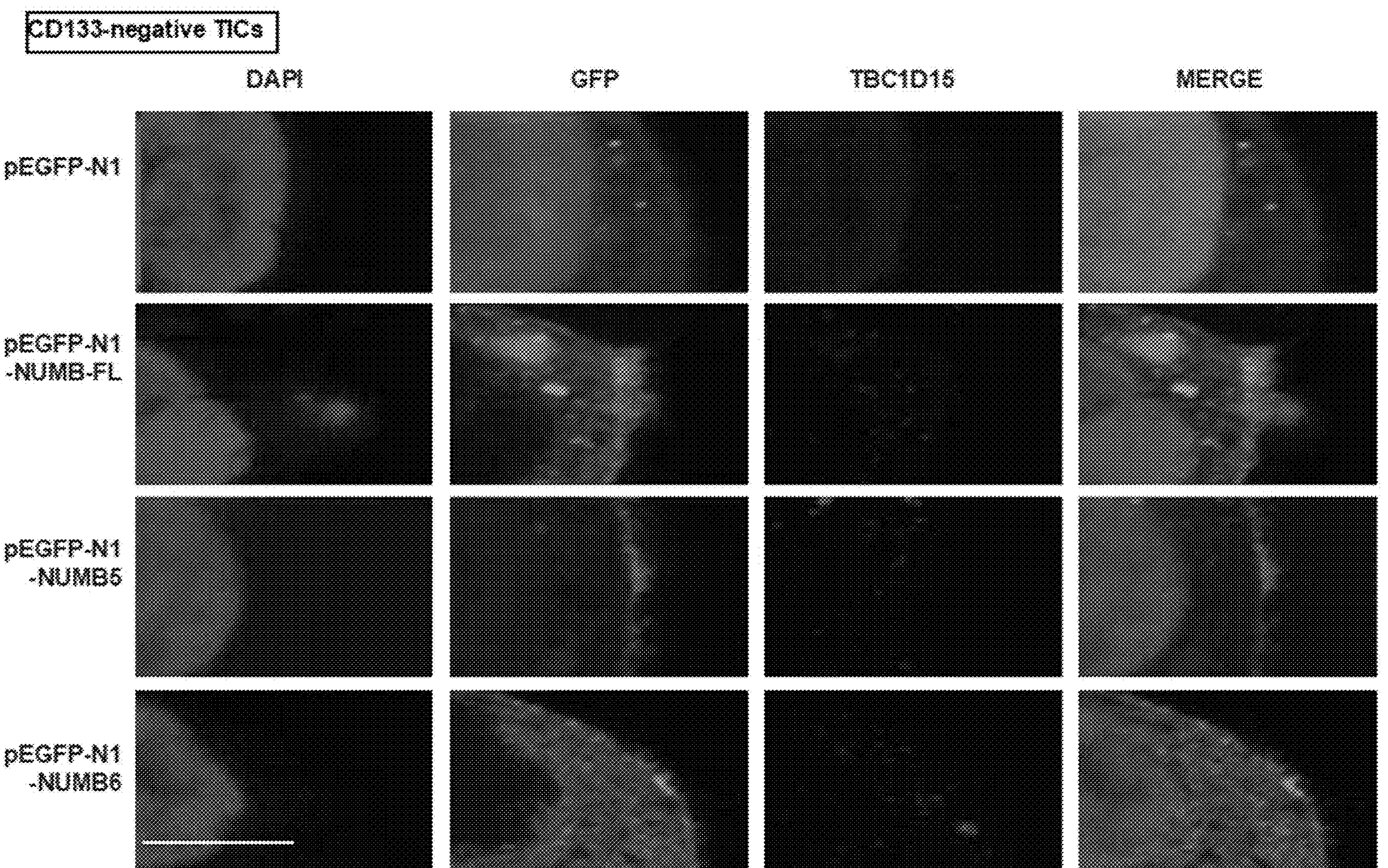

FIG. 2H depicts that TBC1D15 and NUMB isoforms are localization in CD133-negative TICs. CD133-negative TICs were transfected with GFP-NUMB full-length, GFP-NUMB5, or GFP-NUMB6, and analyzed by immunofluorescence microscopy. Merge images show TBC1D15 (endogenous, third column) and GFP-NUMBs (second column). Scale bars: 7.4 μm.

FIGS. 3A-3H depict that the TBC1D15-NICD complex increases mitochondrial number and recruits mitochondria to the nucleus.

(3A) ChIP-seq analysis with anti-NOTCH1 of TBC1D15 in CD133 TICs. Upper panel (left), scheme of ChIP-seq experiment and analysis. Bottom panel, Gene set depletion analysis using Gene Ontology (GO) cellular components terms by Enrichr analysis website (maayanlab.cloud/Enrichr/). Bar graphs indicated statistical significance shown as p-value (upper right and lower panels). All the genes that are significantly depleted in ChIP-seq with anti-NOTCH1 of TBC1D15 KO vs. WT in CD133(+) TICs and anti-NOTCH1 of TBC1D15 in CD133(+) vs. negative TICs analysis are used for the analysis.

(3B) Western blot analysis for fraction of cytoplasm, nuclei, and mitochondria in NICD mutant-transfected CD133(+) TICs.

(3C) Co-IP Western blot analysis for fraction of cytoplasm, nuclei, and mitochondria in NICD mutant-transfected CD133(+) TICs.

(3D) Confocal images of localization in TICs with TOM20 (outer membrane of mitochondria marker), FIS1, TBC1D15 and DAPI (nucleus). Scale bar 7.2 μm.

(3E) Graph for number of mitochondria from (D) confocal images. Mitochondria numbers were counted as mean±SD (n=450). p-Values by two-tailed unpaired t test.

(3F) Graph for diameter of mitochondria. Mitochondria diameters were counted as mean±SD (n=400). p-Values by two-tailed unpaired t test.

(3G) Graph for distance from nucleus. Mitochondria distance from nucleus were counted as mean±SD (n=400). p-Values by two-tailed unpaired t test.

(3H) qRT-PCR analysis of mitochondria metabolic-related genes (SLC25A16, FIS1, ATP5B and MRPS10) in indicated cells. Data are represented as ±SD (n=3). p-Values by two-tailed unpaired t test.

Figures 4A, 4B:
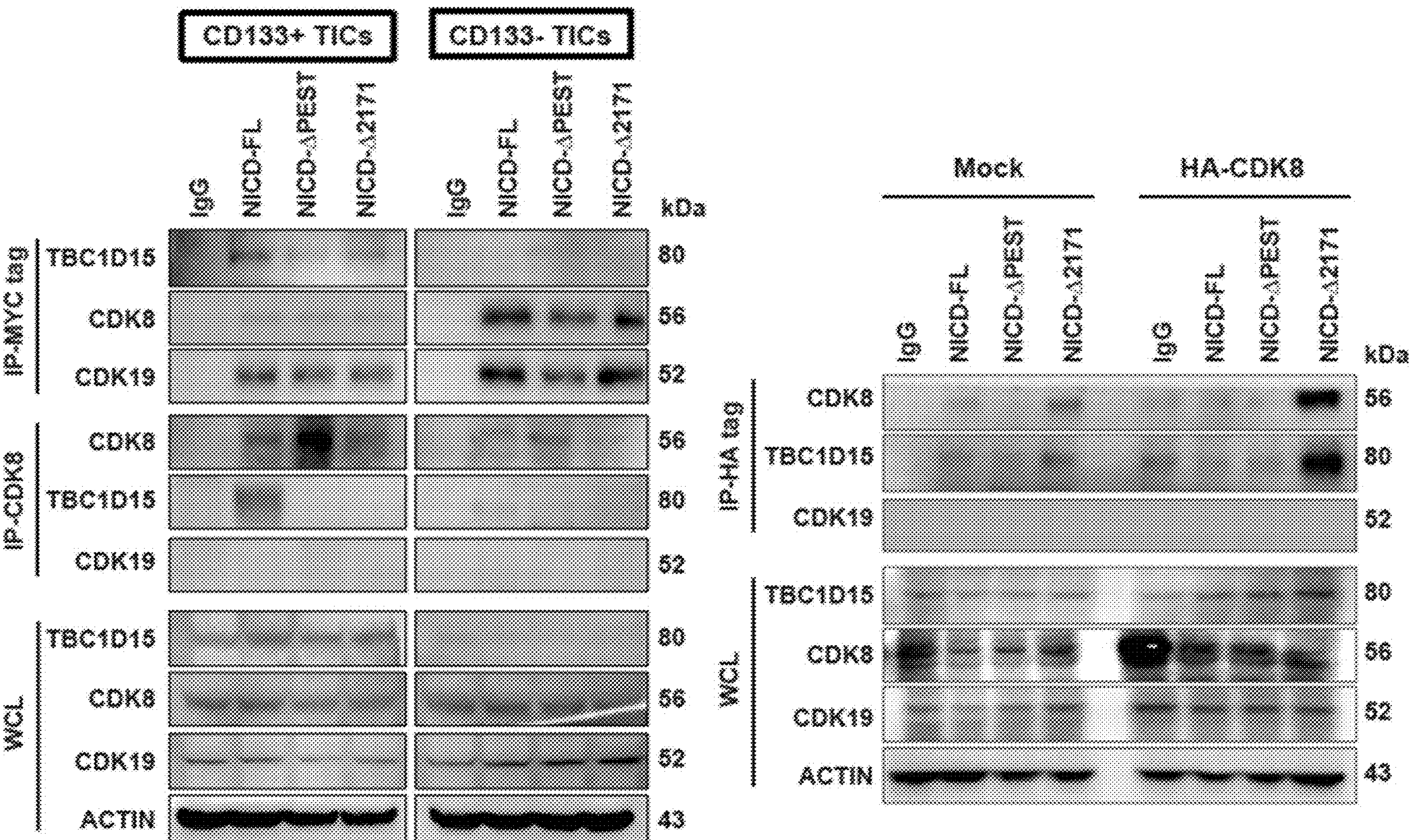
Figure 4C:
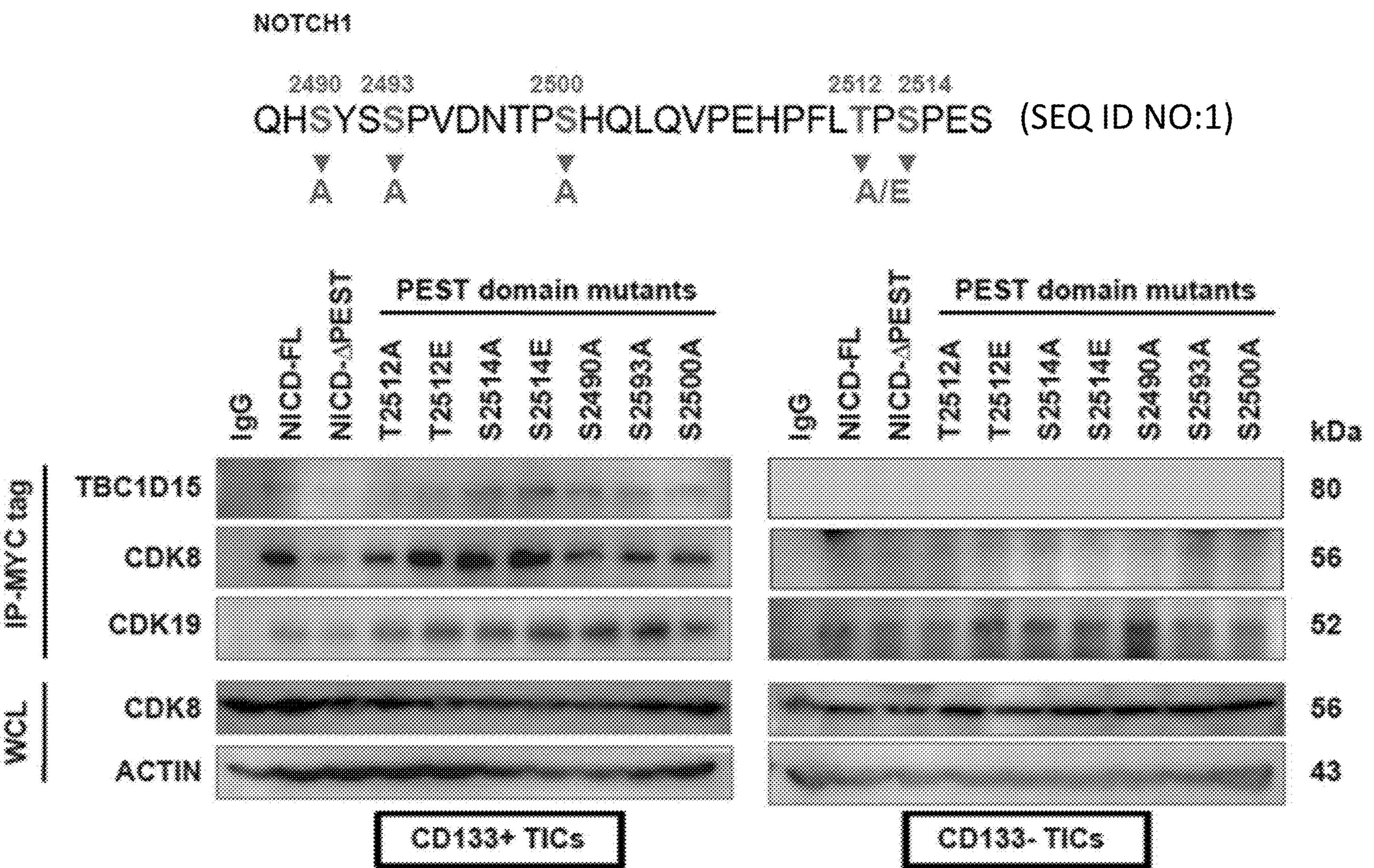

FIGS. 4A-4C depict the Phosphorylation of NICD by TBC1D15 and CDK8 complexes in the PEST domain.

(4A) CD133-positive and CD133-negative TICs transfected with myc-NICD-FL, or a NICD deletion mutant (ΔPEST or Δ2171) were analyzed for the expression of TBC1D15, CDK8 and CDK19 protein by Co-IP-Western blotting.

(4B) CD133-positive TICs co-transfected with HA-CDK8 and myc-NICD-FL, or a NICD deletion mutant (ΔPEST or Δ2171) were analyzed for the expression of TBC1D15, CDK8 and CDK19 protein by Co-IP-Western blotting.

(4C) Top, representative phosphorylation site and mutation sites of PEST domain of NICD. Residues 2488-2517 are described in SEQ ID NO:1. Bottom panel, Co-IP Western blot analysis for interacted with TBC1D15 and mutants of PEST domain in CD133 positive vs negative TICs.

FIGS. 5A-5D depict that NICD T2512A/52514A mutant shows increased stability and decreased binding to Fbw7.

(5A) Co-IP Western blot analysis for interaction of Fbw7 with T2512/S2514 mutants of PEST domain in CD133-positive TICs.

(5B) Top panel, representative images show sequence alignment of NOTCH1, Cyclin E, c-Myc, and c-Jun Fbw7 phospho-degrons as SEQ ID NOs:2-5, respectively. Bottom panel, Co-IP Western blot analysis for interaction with c-Jun, c-Myc and mutants of PEST domain in CD133-positive TICs.

(5C) Co-IP Western blot analysis for interaction with Fbw7, c-Jun and mutants of c-Jun in CD133 positive vs negative TICs.

(5D) Ubiquitination assay of anti-Myc IP of CD133(+) TICs treated with the proteasome inhibitor MG132 (carbobenzoxy-Leu-Leu-leucinal) after transfection with the indicated plasmids.

Figure 6A:
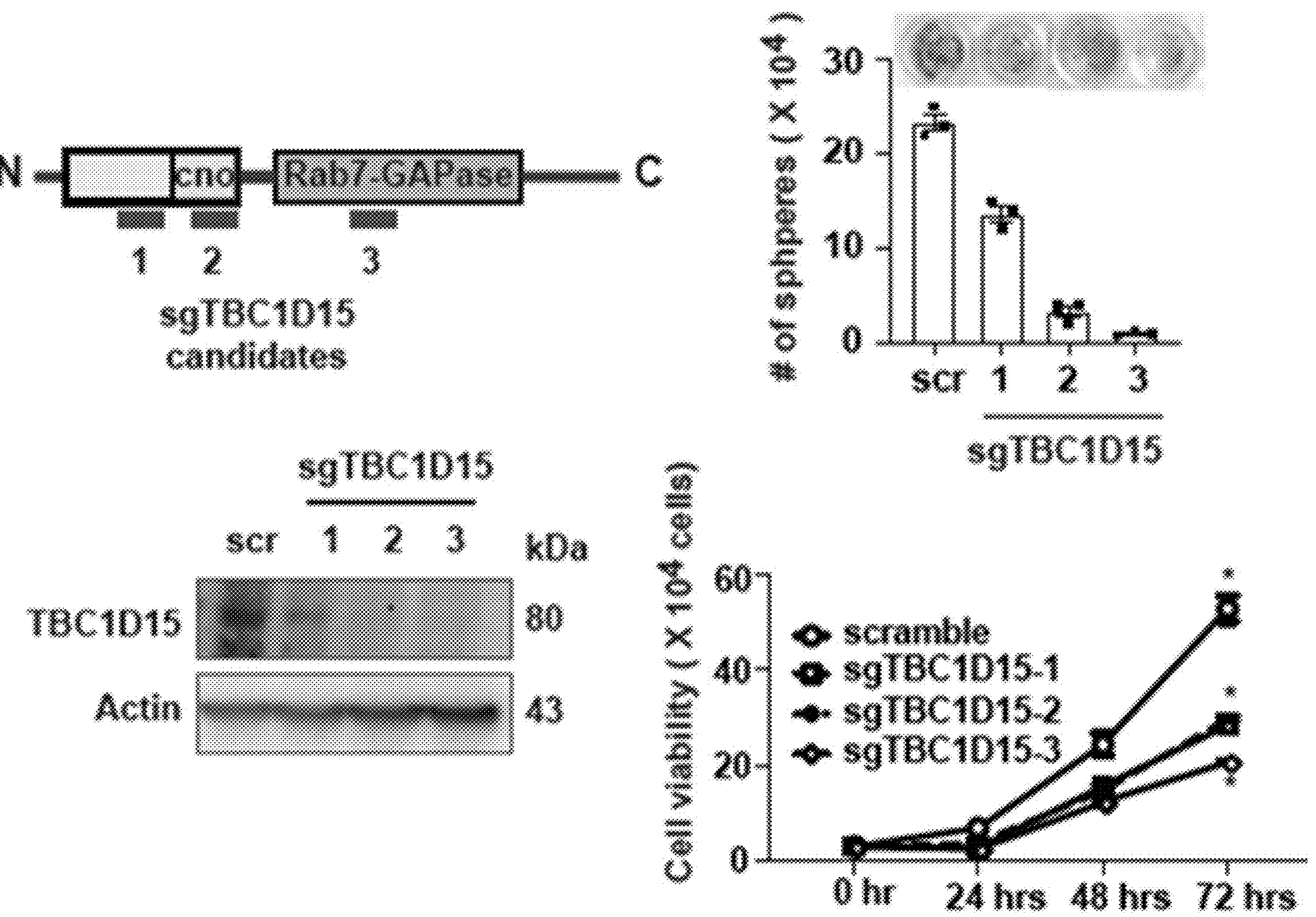
Figure 6B:
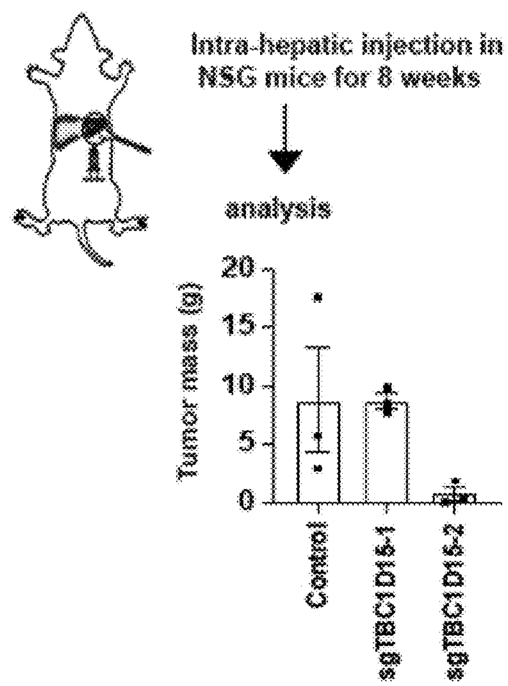
Figure 6C:
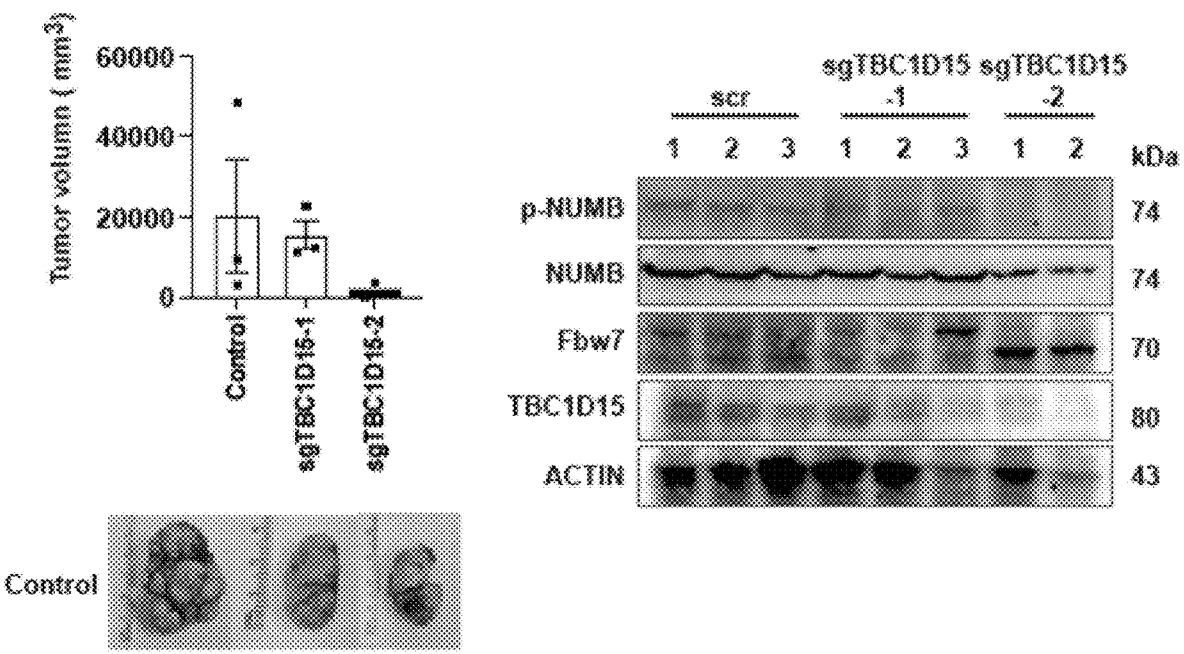

FIGS. 6A-6C depict that TBC1D15 knock-out (KO) reduced tumorigenesis.

(6A) Left panel, Schematic illustrations of three target position for TBC1D15 for knockout (KO), Western blot analysis for expression of TBC1D15 in CRISPR RNP-Cas9 TBC1D15 KO CD133(+) TICs. Right panel, the number of spheres and cell viability that formed in indicated cells.

(6B) Schematic illustration of intra-hepatic injection in NSG mice with CD133(+) TICs or CRISPR RNP-Cas9 TBC1D15 KO CD133(+) TICs and tumor mass.

(6C) Tumor volumes of intra-hepatic injection in NSG mice with CD133(+) TICs or CRISPR RNP-Cas9 TBC1D15 KO CD133(+) TICs. (Right) Immunoblot analyses showed that TBC1D15 protein was reduced in sgRNA targeting TBC1D15.

FIGS. 7A-7G depict that activated NOTCH can be targeted by small molecule inhibitors.

(7A) Analyses of 3D structure of TBC1D15-NOTCH1 interaction identified TBC1D15 N terminal region docking with a.a.1805-2113 of NOTCH1. Inhibitor A efficiently binds both interactions domains for TBC1D15-NOTCH and TBC1D15-NUMB.

(7B) A diagram depicting the screening scheme for selective inhibitors of TBC1D15-NOTCH interaction using the wild type NOTCH1 PEST/STR domain peptide and its mutant. See SEQ ID NOs:6-12 and 1, as depicted. Both were labeled with FITC and used with recombinant TBC1D15 for fluorescence polarization assay. The mutant served as a negative control. Mutant peptides lost binding ability to TBC1D15, indicating that these Tyrosine (Y) residues are primary binding sites of the PEST domain and NOTCH1 Intracellular Domain (NICD). The lower right panel depicts the interaction of Wild Type or Mutant NOTCH-STR/PEST with TBC1D15, without a small molecule inhibitor, in the polarization assay.

(7C) Inhibitor A blocked NOTCH1/3-TBC1D15 interactions (left), selectively kills $CD133^+$ Huh7 cells but not $CD133^-$ Huh7 cells or primary hepatocytes (middle) and abrogates NOTCH-CFP and NANOG-GFP reporter activities (right). $^{**}p<0.01$. Huh7 is a differentiated hepatocyte-derived carcinoma cell line.

(7D) A dose-dependent inhibitory effect of Inhibitor A on tumor growth in NSGTM mice transplanted with dsRed-labeled TICs.

(7E) Imaging for dsRed-labeled tumors in the mice described above. Tumors with fluorescence emission were detected only in the mice treated with vehicle or 10 mg/kg dose, but not in those treated with higher doses.

(7F) Inhibitor A suppressed the growth of patient HCC transplanted into NSGTM mice, and this effect largely diminished when HCC tissues were infected with an adeno-associated virus (AAV) vector delivering both N1ICD (that is, NOTCH1's intracellular domain) and HA-NUMB-3D prior to the transplantation. Inhibitor A suppressed the growth of patient HCC transplanted into NSGTM mice (PDX model), and this effect was negated by N1ICD and NUMB-3D co-transduction. HA-NUMB-3D is HA-tagged phosphor-mimetic mutant of NUMB protein wherein three serine resides of phosphorylation sites are all replaced with phosphor-mimetic amino acid, D (aspartic acid), to have constitutively phosphorylated status of NUMB protein that reduce the binding ability between NOTCH and NUMB. (Phosphomimetics are amino acid substitutions that mimic a phosphorylated protein. For example, aspartic acid is chemically similar to phosphor-serine.)

(7G) Inhibitor A-treated xenograft tumors have an elevated p53 protein level, but reduced N1ICD and NANOG protein levels. We then tested the therapeutic efficacy of the Inhibitor A in the PDX model of HCC. When the two oncogenic targets were restored by use of AAV vector-mediated co-transduction of both activated N1ICD and phosphormimetic NUMB, the tumor-killing effect of Inhibitor A was negated. Inhibitor A's tumor killing effects are largely dependent upon the inhibition of NOTCH activation and suppressing NUMB phosphorylation status.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3*rd ed., Revised*, J. Wiley & Sons (New York, NY 2006); March, *Advanced Organic Chemistry Reactions, Mechanisms and Structure* 7*th ed.*, J. Wiley & Sons (New York, NY 2013); and Sambrook and Russel, *Molecular Cloning: A Laboratory Manual* 4*th ed.*, Cold Spring Harbor Laboratory Press (Cold Spring Harbor, NY 2012), provide one skilled in the art with a general guide to many of the terms used in the present application. For references on how to prepare antibodies, see D. Lane, Antibodies: *A Laboratory Manual* 2*nd ed.* (Cold Spring Harbor Press, Cold Spring Harbor NY, 2013); Kohler and Milstein, (1976) Eur. J. Immunol. 6: 511; Queen et al. U.S. Pat. No. 5,585,089.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

An "effective amount" of an agent (e.g. an inhibitor of TBC1D15) is an amount sufficient to provide an observable improvement over the baseline clinically observable signs and symptoms of the depressive disorder treated with the agent.

The term "treat" means to relieve, reduce or alleviate at least one symptom of a disease in a subject. For example, in relation to tumor or carcinoma, the term "treat" may mean to reduce a tumor size, or to arrest, delay and/or reduce the risk of tumor growth or worsening of the cancer.

The term "subject" is intended to include animals, which are capable of suffering from or afflicted with tumors or TICs, as well as conditions caused by TICs. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a tumor, or conditions caused by the tumor.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

Pharmacologically active metabolites include those that are inactive but are converted into pharmacologically active forms in the body after administration.

Pharmaceutically acceptable salts comprise, but are not limited to, soluble or dispersible forms of compounds that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum. In some aspects, a pharmaceutically acceptable salt is a salt of an acid and a basic nitrogen atom of a purine compound.

An "analog," "structural analog," or "chemical analog" is a compound having a structure similar to that of another compound, but differing from it in one or more atoms, functions groups, or substructures. A structural analog in theory can be formed from the other compound. Herein a latanoprost analog can be travoprost, unoprostone or bimatoprost. They are analogs of prostaglandin, belonging to a class of eicosanoids or to a prostanoid class of fatty acid derivatives. In some aspects, a prostaglandin analog has a structure of a five-membered ring (saturated or unsaturated) substituted with (1) two hydroxyl groups, or one hydroxyl group and one ketone group, or two ketone groups, and (2) two independent C3-C20 alkane or alkene chains, each independently with one or more substitutions/functional groups such as carboxylic acid, ketone, hydroxyl, phenyl, heteroatoms (e.g., O, N, or S), amide, or branched C2-C5 alkane or alkene optionally with heteroatoms (e.g., F, Cl).

Herein, we describe the NUMB-mediated NOTCH1 activation mechanism by which TBC1D15 inhibits NOTCH1 activation in CD133(+) TICs and its effect on mitochondrial metabolism. Further, we have identified small molecule substances targeting the NOTCH1 domain that binds TBC1D15, which can be used as a therapeutic against CD133(+) TICs.

In screening for such a property, we have discovered that TBC1D15 interacts with all NOTCH isoforms, activates NOTCH pathway, and induces Nanog and TIC self-renewal in a NOTCH-dependent manner. Here we examined HCC development in alcohol Western diet-fed Tg mice with hepatocyte-specific TBC1D15 deficiency or expression of non-phosphorylatable NUMB mutations. Liver-specific TBC1D15 deficiency or non-p-NUMB expression reduced TIC numbers and HCC development. TBC1D15 and p-NUMB are required for liver tumor development in vivo. We identified NuMA1 and NOTCH1-4 as TBC1D15-interacting proteins by large-scale immunoaffinity purification and LC-MS analysis. TBC1D15-NuMA1 association impaired asymmetric division machinery by hijacking NuMA from LGN binding, thereby favoring TIC self-renewal. TBC1D15-NOTCH1 interaction activated and stabilized NOTCH1 which upregulated transcription of NANOG essential for TIC expansion. Through interaction domain mapping of TBC1D15, 3-D computational structural docking analysis, and high-throughput screening, we identified a small molecule inhibitor of TBC1D15 interaction with NOTCH. This abrogated the growth of patient HCC in patient-derived xenograft (PDX) mice. TBC1D15 activated three new oncogenic pathways to promote self-renewal, p53 loss, and Nanog transcription in TICs. Thus, this central regulator can serve as a therapeutic target for treatment of hepatocellular carcinoma (HCC). We have discovered, first, in alcohol-induced TICs with symmetric division, NUMB is hyperphosphorylated through a NANOG-AurA kinase-aPKCζ pathway, causing p53 dissociation from NUMB and its degradation. NANOG protein is a pluripotency transcription factor; Aurora A kinase is an enzyme in the family of mitotic serine/threonine kinases; and atypical protein kinase C (aPKCζ) isozymes are unique in the PKC superfamily in that they are not regulated by the lipid second messenger diacylglycerol. Second, TICs overexpress TBC1D15 (which encodes TBC1 domain family member 15), a new NUMB-interacting protein which promotes aPKCζ activity for p53 degradation. Third, TIC self-renewal is dependent on TBC1D15 and NUMB phosphorylation. Fourth, TBC1D15 deficiency or non-phosphorylatable mutations of NUMB reduces liver tumor incidence and tumor-associated NANOG-positive TICs in hepatitis C virus (HCV) protein non-structural (NS) 5A transgenic (Tg) mice fed with alcohol Western diet. And next, the loss of p53 alone in hepatoblasts is not sufficient for transformation but expression of TBC1D15 endows these cells tumor-initiating activity. These results indicate that TBC1D15 is a new driver for symmetric division and possesses a previously uncharacterized tumorigenic property besides facilitating p53 degradation.

Chemical library screening and docking analysis have identified small molecules which blocks the TBC1D15-NOTCH interaction and Notch intracellular domain (NICD)-dependent Nanog promoter activity.

Various embodiments provide methods for treating a subject with a tumor or a cancer, or treating a subject suspected of having a tumor, wherein the methods include administering an effective amount of a composition comprising, or consisting of, an inhibitor of TBC1D15 and a pharmaceutically acceptable excipient to the subject. Methods for treating or reducing the severity of a cancer in a subject are also provided, which include administering an effective amount of a composition comprising an inhibitor of TBC1D15 and a pharmaceutically acceptable excipient to the subject. Furthermore, methods for treating a subject detected with $CD133^+$ TICs are also provided, which include administering an effective amount of a composition comprising an inhibitor of TBC1D15 and a pharmaceutically acceptable excipient to the subject. Yet, additional methods are provided for administering an inhibitor of TBC1D15 to a subject, which include administering an effective amount of a composition comprising an inhibitor of TBC and a pharmaceutically acceptable excipient to the subject, wherein the subject is diagnosed with a tumor, cancer, or carcinoma, or detected with a presence of CD133$^+$ TICs, or having one or more inflammations such as chronic inflammation or infection in one or more tissue. In various aspects of these methods, administering the inhibitor of TBC1D15 results in reduction or abrogation of TBC1D15-mediated NOTCH signaling pathway, thereby inducing apoptosis or inhibiting proliferation of TICs, and/or inhibiting the growth or reducing the size of tumor in the subject.

An inhibitor of TBC1D15 can be one that inhibits binding between TBC1D15 and NOTCH1, or one that inhibits expression of TBC1D15 gene.

Figure 7A:
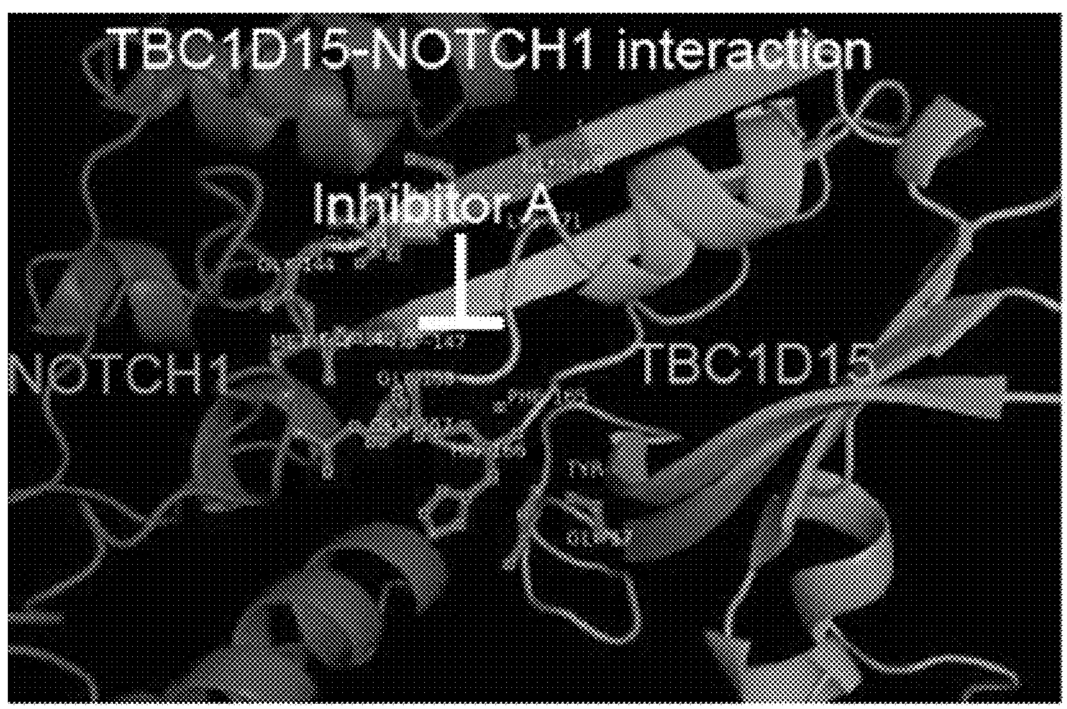
Figure 7B:
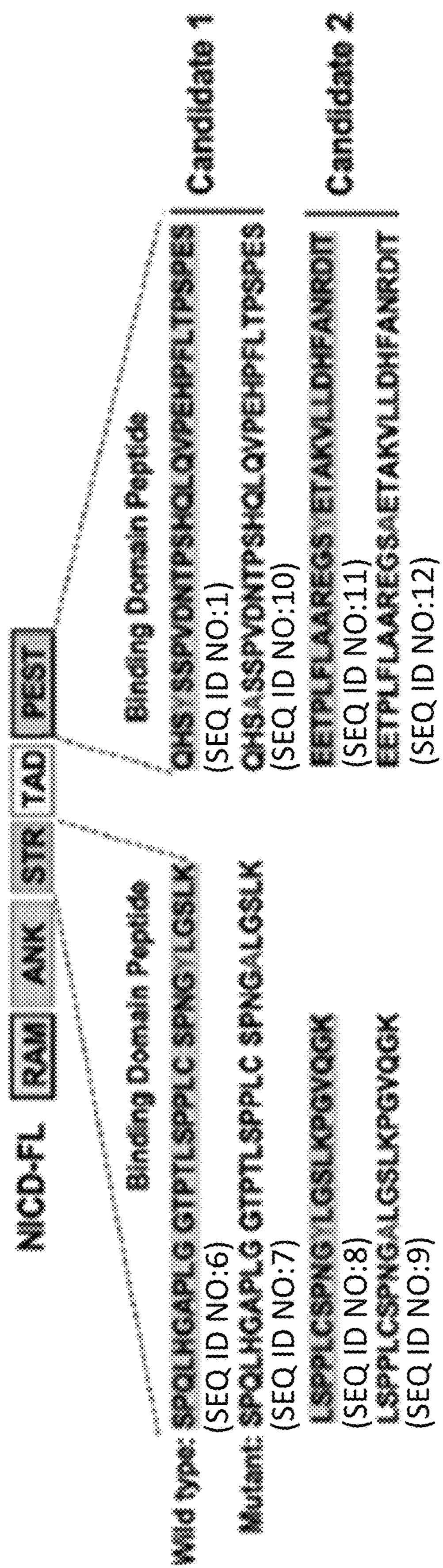

In some embodiments, an inhibitor of TBC1D15 is a compound that inhibits binding of TBC1D15 with NOTCH, or inhibits the interaction between TBC1D15 and NOTCH. For example, the inhibitor of TBC1D15 can bind to TBC1D15, thereby blocking the binding/interaction of TBC1D15 with a NOTCH protein (e.g., NOTCH1 or NOTCH3). In a further aspect, the inhibitor of TBC1D15 can bind to TBC1D15, thereby blocking the interaction of TBC1D15 with the NOTCH protein as well as blocking the interaction of TBC1D15 with NUMB protein. In another aspect, the inhibitor of TBC1D15 can block the interaction or binding between TBC1D15 and the Ser-Thr-rich (STR) region or the PEST region within a NOTCH-intracellular domain. In yet another aspect, the inhibitor of TBC1D15 can be identified through a fluorescence polarization assay, wherein a fluorophore-labeled, binding domain of NOTCH1 (e.g., the STR domain or the PEST domain, or a peptide fragment thereof, within NICD) would have an increased fluorescence polarization (FP) when it is non-covalently bound to TBC1D15, as depicted in FIG. 7B, or a decreased FP when it is not bound to TBC1D15 due to the presence of an inhibitor of TBC1D15. Other techniques for determining protein interactions or protein-protein affinity can also be used in screening for an inhibitor of TBC1D15, such as plasmon resonance or Förster resonance energy transfer.

In various aspects, the compound that inhibits binding/interaction between TBC1D15 and NOTCH is also effective in inducing toxicity selectively to a CD133$^+$ tumor cell or a CD133$^+$ TIC over a CD133$^-$ TIC or a normal cell, and/or reducing gene expression of NOTCH and/or NANOG in a tumor cell or a TIC. For example, the inhibitor of TBC1D15 can reduce proliferation or viability of CD133$^+$ TICs, but does not reduce proliferation or viability of CD133$^-$ TICs or a normal (non-TIC) cell. Alternatively, the inhibitor of TBC1D15 can reduce proliferation or viability of CD133$^+$ TICs significantly more than CD133$^-$ TICs or a normal (non-TIC) cell.

Various embodiments provide that the inhibitor of TBC1D15 is a prostaglandin analogue or a pharmacologically active metabolite, salt, solvate or racemate of prostaglandin analogue, which inhibits binding/interaction between TBC1D15 and NOTCH and optionally further effective in inducing toxicity selectively to a CD133$^+$ tumor cell or a CD133$^+$ TIC over a CD133$^-$ TIC or a normal cell, and/or reducing gene expression of NOTCH and/or NANOG in the tumor cell or the TIC. In some aspects, a prostaglandin analog includes latanoprost, travoprost, unoprostone and bimatoprost. In some embodiments, the inhibitor of TBC1D15 is latanoprost or a pharmacologically active metabolite, salt, solvate or racemate of latanoprost. In some embodiments, the inhibitor of TBC1D15 is latanoprost acid or a pharmacologically active metabolite, salt, solvate or racemate of latanoprost acid.

Further embodiments provide a small molecule inhibitor of TBC1D15 for use in treatment of cancer, such as one with CD133$^+$ TICs, including latanoprost acid, arginine, creatine, bethanidine, guanadrel, metformin, brimonidine, cimetidine, guanidine, zanamivir, clonidine, amiloride, guanabenz, tizanidine, epinastine, chlorhexidine, pheformin, famotidine, apraclonidine, guanfacine, streptomycin, proguanil, guanethidine, debrisoquine, iobenguane, cycloguanil, peramivir, romifidine, tegaserod, diphenylguanidine, guanoxan, biguanide, iobenguane sulfate I-123, α-bungarotoxin (CAS number 11032-79-4), tricyclic guanidine alkaloids, α-conotoxin AuIB (CAS number 216299-21-7), α-conotoxin PIA (CAS number 669050-68-4), α-conotoxinMII (CAS number 175735-93-0), α-conotoxin PnIA (CAS number 705300-84-1), phenformin, or a pharmacologically active metabolite, salt, solvate or racemate of any of these compounds. Preferably some of these compounds suppress the growth of tumor cells or TICs.

Some embodiments provide a method for treating cancer in a subject or inhibiting growth of tumor in a subject, comprising administering a pharmaceutical composition comprising an effective amount of latanoprost acid or latanoprost, thereby reducing or blocking the interaction between TBC1D15 and NOTCH1, and reducing or blocking the interaction of TBC1D15 with NUMB.

Latanoprost is an ester prodrug which can be activated to an acid form, latanoprost acid. Latanoprost acid, or (5Z,9α, 11α, 15R)-9,11,15-Trihydroxy-17-phenyl-18,19,20-trinor-prost-5-en-1-oic acid, (Z)-7-[(1R,2R,3R,5S)-3,5-Dihydroxy-2-[(3R)-3-hydroxy-5-phenylpentyl]cyclopentyl]hept-5-enoic acid, has the following structure:

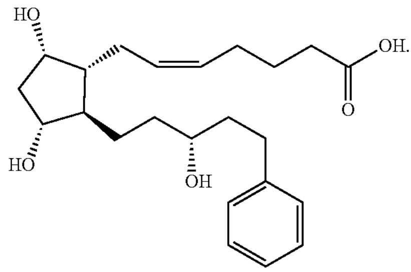 [SMILES: O=C(O)CCC/C=C\C[C@@H]1[C@@H](CC[C@@H](O)CCc2ccccc2)[C@H](O)C[C@@H]1O]

Further embodiments provide that an inhibitor of TBC1D15 is one that inhibits expression of TBC1D15 gene. For example, an inhibitor that inhibits expression of TBC1D15 gene can be a guide RNA that targets the TBC1D15 gene for nuclease (e.g., CRISPR-associated nuclease) cleavage. In some aspects, an inhibitor that inhibits expression of TBC1D15 gene can induce a gene knockout of TBC1D15, using one or more techniques such as homologous recombination, or involving site-specific nucleases, zinc-fingers, transcription activator-like effector nucleases (TALENs), or clustered regularly interspaced short palindromic repeats (CRISPR)/Cas9.

In various embodiments, the method is for treating hepatocellular carcinoma, liver cancer, lung cancer, breast cancer, ovary cancer, or a combination thereof, or a cancer associated with TBC1D15-mediated p53 apoptosis, or a cancer with increased level of TBC1D15 expression in tumors or an expression level of TBC1D15 above a reference value. In some embodiments, the reference value is the median or average expression level of TBC1D15 in primary tumors in a plurality of different cancer patients such as lung, breast, ovary and liver cancer patients. In other embodiments, the method is for treating a subject with hepatitis, especially chronic hepatitis, and at risk of developing a liver cancer. In additional embodiments, the methods further include selecting a patient with the hepatocellular carcinoma, liver cancer, lung cancer, breast cancer, or ovary cancer, or detecting the hepatocellular carcinoma, liver cancer, lung cancer, breast cancer, or ovary cancer in the subject, prior to the administration of the inhibitor of TBC1D15. In other embodiments, the methods can be used to treat a subject with a cancer including, but not limited to, blood cancer, B-cell lymphomas (Hodgkin's lymphomas and/or non-Hodgkins lymphomas), brain tumor, breast cancer, colon cancer, rectal cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer In some embodiments, the method is for treating a subject with an increased amount of TICs, especially $CD133^+$/$CD49f^+$ TICs, in one or more solid organ tissues (such as tumor tissue). In additional embodiments, the methods further include selecting a subject with a higher amount of TICs especially $CD133^+$/$CD49f^+$ TICs in one or more solid organ tissues, or detecting a higher amount of TICs especially $CD133^+$/$CD49f^+$ TICs in the one or more solid organ tissues, compared to that in a non-cancerous tissue or from a matched tissue in a healthy subject.

In some embodiments, the subject in the methods is one detected with an increased expression level of TBC1D15 protein or gene in a tumor sample, compared to that in a non-tumor sample, or the increased expression level in a tissue suspected of having a tumor of the subject, compared to that in a matched tissue from a subject free of the tumor. In additional embodiments, the methods further include selecting a subject detected with a higher expression level of TBC1D15 protein or gene in a tumor sample, compared to that in a non-tumor sample or a healthy subject.

In further embodiments, the method comprises measuring expression level of TBC1D15 prior to administration of the inhibitor. In other embodiments, the method further comprises measuring a decreased amount of $CD133^+$ tumor cells or $CD133^+$ TICs after administration of the inhibitor compared to the amount before the administration. In other embodiments, the method further comprises measuring an increased p53 protein level in the tumors after the administration of the inhibitor compared to the level before the administration.

In yet another embodiment, the subject has an increased phosphorylation of NUMB isoform 5 in $CD133^+$ TICs or $CD133^+$ tumor cells, compared to that in $CD133^-$ TICs or $CD133^-$ tumor cells, prior to receiving the administration of the inhibitor of TBC1D15; and/or the subject's phosphorylation level of NUMB isoform 5 in $CD133^+$ TICs or $CD133^+$ tumor cells is reduced, following the administration of the inhibitor of TBC1D15, compared to before the administration, or the phosphorylation level of NUMB isoform 5 in $CD133^+$ TICs or $CD133^+$ tumor cells after the administration is reduced to a level similar to that in a non-cancerous cell.

In yet another embodiment, the subject has an increased number of mitochondria in $CD133^+$ TICs or $CD133^+$ tumor cells, compared to that in $CD133^-$ TICs or $CD133^-$ tumor cells, prior to the administration of the inhibitor of TBC1D15; and/or the subject's amount of mitochondria in $CD133^+$ TICs or $CD133^+$ tumor cells is reduced, following the administration of the inhibitor of TBC1D15, compared to before the administration, or the mitochondria number in $CD133^+$ TICs or $CD133^+$ tumor cells after the administration is reduced to a level similar to that in a non-cancerous cell.

The compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to amino acids, starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

The compositions according to the invention can also be encapsulated, tableted or prepared to provide sustained or controlled release (or increase the half-life). Pharmaceutically acceptable solid or liquid carriers may be added to enhance or stabilize the composition, to facilitate preparation of the composition, or to provide sustained or controlled release (or increase the half-life) of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. Emulsion carriers include liposomes, or controlled release polymeric nanoparticles known in the art. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems such as polymeric nanoparticles are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277. The carrier may also include a sustained release material such as glyceryl monostearate or glyceryl distearate, alone or with a wax.

The pharmaceutical compositions according to the invention may be delivered in a therapeutically effective amount. The precise therapeutically effective amount is that amount of the composition that will yield the most effective results in terms of efficacy of treatment in a given subject, which can vary depending upon a variety of factors such as the physiological condition of the subject, the nature of the excipients, and the route of administration, and can be determined by a skilled clinical or pharmacological practitioner, for instance, by monitoring a subject's response to administration of a compound and adjusting the dosage accordingly. In some embodiments, the methods include administering the composition comprising the inhibitor of TBC1D15 at 1-10, 10-20, 20-30, 30-40, 40-50, 50-60, 60-70, 70-80, 80-90, 90-100, 100-200, 200-300, 300-400, 400-500, 500-600, 600-700, 700-800, 800-900, or 900-1,000 mg/kg of the subject. In some embodiments, the methods include administering the composition comprising the inhibitor of TBC1D15 at 1-10, 10-20, 20-30, 30-40, 40-50, 50-60, 60-70, 70-80, 80-90, 90-100,100-200, 200-300, 300-400, 400-500, 500-600, 600-700, 700-800, 800-900, or 900-1,000 μg/kg of the subject.

In some embodiments, a liquid/suspension formulation may be preferred for an intraperitoneal or intravenous administration of the composition. For example, these formulants may include oils, polymers, vitamins, carbohydrates, amino acids, salts, buffers, albumin, surfactants, bulking agents or combinations thereof.

Various methods of screening for, identifying, or assaying small molecule inhibitors of TBC1D15 for use in treating cancer are provided, or for inhibiting, blocking, or reducing the interaction of TBC1D15 and NOTCH. The screening/identification/assaying methods include measuring a decreased level of binding between TBC1D15 and NOTCH (e.g., NOTCH1 and/or NOTCH3) in the presence of the small molecule of interest compared to the level of binding in the absence of the small molecule of interest. In some implementations, these methods include contacting a molecule of interest with a mixture comprising TBC1D15 and NOTCH1, or TBC1D15 and NOTCH3, and measuring a decreased level of binding between TBC1D15 and NOTCH1 or NOTCH3 in the presence of the molecule of interest compared to the level before the contact with the molecule of interest, or compared to the level in the absence of the molecule of interest. A molecule of interest determined to decrease the binding between TBC1D15 and NOTCH1 or NOTCH3 is indicated to be an agent for use in treating a subject with the cancer or inhibiting the tumor growth.

In a further implementation, the methods also include detecting/measuring/assaying a decreased viability of $CD133^+$ tumor cells or $CD133^+$ TICs in the presence of the molecule of interest, compared to the amount in the absence of said molecule of interest. Preferably, the molecule of interest, or identified inhibitor of TBC1D15 does not lead to a decreased viability of $CD133^-$ TICs or non-tumor cells upon contact.

In some aspects, measuring a level of the binding between TBC1D15 and NOTCH1 or NOTCH 3 comprises performing an immunoprecipitation assay, a fluorescence polarization assay, a FRET assay, or a plasmon resonance.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

TBC1D15 Enhanced NOTCH1 Protein Activation and Stabilization in CD133-Positive TICs To generalize TBC1D15-mediated NOTCH stabilization and activation in different cancer types, we performed an extensive meta-analysis of TBC1D15 expression in tumors arising from diverse tissue types. TBC1D15 expression increased in various tumor types, including those derived from breast, lung, thyroid and ovary (FIG. 1A). The corresponding outcome worsened with higher levels of TBC1D15 mRNA expression in liver, lung, breast, and ovary cancer patients from the TCGA database (FIG. 1B). That is, the relevance of prognosis with TBC1D15 expression in lung, breast, and ovary cancer patients from TCGA database indicates that higher expression of TBC1D15 was associated with significant poor prognosis, similar to HCC.

We validated whether CD133(+) TICs have higher TBC1D15 protein levels. For this, CD133(+)/CD49f(+) TICs were isolated from lung cancer cell lines (Calu3 and H1299) by CD133 and CD49f affinity magnetic-microbeads (FIG. 1F). The TBC1D15 protein levels were confirmed to be higher in the CD133(+)/CD49f(+) TICs compared to CD133(−)/CD49f(−) TICs, indicating that TBC1D15 was associated with TIC characteristics, such as NOTCH-mediated stemness induction (FIG. 1G). That is, for investigation of high TBC1D15 expression, we isolated CD133-positive and CD49f-positive TICs from lung cancer cell lines (Calu3 and H1299 cell lines) by CD133 and CD49f microbeads. We found high expression of TBC1D15 in the CD133-/CD49f-double positive TICs cells. CD49f is also known as integrin α6.

TBC1D15 and NOTCH1 Expression is Increased in Hepatocellular Carcinoma (HCC) Patients We conducted a co-expression analysis of TBC1D15 protein in the Oncomine database (www.oncomine.org), which compared NOTCH1, NOTCH2, NOTCH3, NOTCH4, and TBC1D15 in 115 normal liver tissues vs. 95 HCC samples (FIG. 1H, top). We found a significant linkage of NOTCH gene expression to TBC1D15 by this comparison. Experimental validation of this information was carried out by immunohistochemistry (IHC) examination of HCC and matched normal liver tissues (FIG. 1C). The results showed that TBC1D15 expression was significantly higher in HCC than in normal tissue sections. Moreover, significant increases in NOTCH and NUMB expression appeared to correlate with HCC and TBC1D15 expression.

That is, we used Oncomine database (www.oncomine.org) to check the expression status of TBC1D15 and NUMB in various liver cancers (TCGA, Mas, Roessler, and Roessler liver 2 statics). The liver statics showed that expression of TBC1D15 was upregulated in HCC while NUMB showed downregulation. Subsequently, we conducted the co-expression analysis of TBC1D15 protein with Oncomine database which covers 5 genes (NOTCH1, NOTCH2, NOTCH3, NOTCH4, and NUMB) in 115 normal liver tissue vs 95 HCC samples. We identified NOTCHs and NUMB gene with correlation with TBC1D15. Moreover, we investigated the relevance of prognosis with TBC1D15 expression in HCC patients from TCGA database using SurvExpress web (bioinformatica.mty.itesm.mx:8080/Biomatec/SurvivaX.jsp) (FIG. 1H, bottom). By examining the TCGA HCC survival data with respect to TBC1D15 expression, we found that higher expression of TBC1D15 was associated with reduced disease-free survival. The results demonstrated that among the HCC, a significant ($p=0.046$) poor prognostics role was observed with TBC1D15 high expression in HCC, although the previous studies reported that TBC1D15 acted as a tumor enhancer in HCC. Immunohistochemistry (IHC) was carried out in HCC and matched normal liver tissues. The results showed that TBC1D15 expression was significantly higher in HCC comparing to matched normal sections. Moreover, significant NOTCH and NUMB expression was related in HCC.

TBC1D15 Interacts with NOTCH1-PEST and NOTCH1-STR Domains in CD133-Positive TICs Previous studies indicated that TBC1D15 mediates three new carcinogenic pathways in TICs which promote self-renewal, p53 loss, and Nanog transcription. One of three things, we showed that TBC1D15 inhibits NUMB-mediated NOTCH degradation by binding to the PEST domain of NOTCH-intracellular domain (NICD) (Choi et al., *Nat Commun* 11, 3084. 10.1038/s41467-020-16616-8).

To begin a mechanistic study as to how TBC1D15 activates the NOTCH and NICD pathways, we performed a protein domain mapping study by creating deletion mutants of protein domains of NOTCH and NICD, including the PEST domain (FIGS. 1D and 1I). Several NICD deletion mutants were constructed and overexpressed in CD133(+) and (−) TICs followed by confirmation of expression by IP-Western blot (FIGS. 1J and 1K). The PEST and STR (Ser-Thr-rich) domains of NICD reduced the interaction with TBC1D15, which was further diminished with mutations of the STR phosphorylation residues (3M and 4M) (FIG. 1D). In the mutants, phosphorylation sites of NOTCH1 STR domains were replaced with Alanine (non-phosphorylateable mutant): the triple mutant, d2171-3M, has 52122A, T2133A, and S2137A; and 4M has residues 2122, 2133, 2137, and 2142 all substituted with alanine. That is, we showed that NOTCH/NICD with deletion mutations where the PEST and STR domains are deleted do not bind to TBC1D15 in transfected CD133-positive TICs. The binding of TBC1D15 to the PEST domain of NOTCH (or the PEST domain in NICD) was confirmed in previous studies (Choi et al., *Nat Commun* 11, 3084. 10.1038/s41467-020-16616-8), but the binding to the STR domain was a new finding. (The STR domain lies within the transactivation domain (TAD), which is upstream or to the N-terminus of the PEST domain, both within the NICD.)

The STR domain has four Ser/Thr-Pro motifs that can be phosphorylated. These motifs are unique recognition sites for a series of proline-directed kinases, such as glycogen synthase kinase 3 beta, cyclin-dependent and MAP kinases. PIN1 (Peptidylprolyl cis/trans Isomerase, and NIMA-Interacting 1) contacts phosphorylated Ser/Thr-Pro motifs in multiple substrates and catalyzes the cis-trans isomerization of specific proline peptide bonds through the carboxy-terminal PPIase domain, resulting in protein conformational changes. It was reported that PIN1 binds to the STR domain and induces a conformational change favorable for NOTCH1 cleavage by γ-secretase.

We tested the binding of PIN1 to the STR domain of TBC1D15 to determine how it interacted through the STR domain. Overexpression of PIN1 in CD133(+) TICs increased binding to NICD and NICD-3M (FIG. 1E). NICD-3M is the triple mutant, d2171-3M (S2122A; T2133A; S2137A). Moreover, we observed decreased binding between TBC1D15 and NICD or STR upon overexpression of PIN1. The results of Myc-tag and HA-tag co-IP in Pin1 overexpressed CD133(+) TICs showed that binding to TBC1D15 was significantly reduced in the presence of Pin1. These results indicated that the binding of TBC1D15 to the NICD STR domain was reduced due to a conformational change of NICD induced upon Pin1 binding. These data indicated that Pin1 interrupted TBC1D15 binding to the NICD and NICD STR domains.

TBC1D15 Does Not Affect NOTCH1 Processing

Pin1 is known to promote tumor formation by binding to the NOTCH/NICD STR domain and regulating its activity. To determine how TBC1D15 affects NOTCH1 activity, we tested whether it regulates NOTCH1 processing through a combination of a disintegrin and metalloproteinase (ADAM) 17 and γ-secretase. We overexpressed a membrane-tethered, ligand-independent wild type NOTCH1, a NOTCH1 derivative [NΔE, that is constitutively cleaved by γ-secretase, releasing active NICD (Rustighi et al., *EMBO Mol Med* 6, 99-119. 10.1002/emmm.201302909)], NΔE-ΔPEST, and NΔE-V1745L in CD133(+) or (−) TICs. We then analyzed the effects of TBC1D15 on endogenous NOTCH1 processing by measuring the amount of NICD produced after ethylenediaminetetraacetic acid (EDTA) and DAPT treatment in vitro. This treatment has been shown to trigger NOTCH1 cleavage by γ-secretase and is blocked by γ-secretase inhibitor (GSI), N—[N-(3,5-Difluorophenacetyl)-L-alanyl]-S-phenylglycine t-butyl ester (DAPT). Treatment with DAPT and EDTA had no observed effect on NICD level (FIGS. 1M and 1N). These results indicated that TBC1D15 interacts with the NOTCH1-PEST domain but this does not affect NOTCH1 processing.

TBC1D15 has Preferentially Interacted with NUMB Isoform 5 and NOTCH1-PEST Domain in CD133-Positive TICs TBC1D15 interacts with the NOTCH1 PEST domain (Choi et al., *Nat Commun* 11, 3084. 10.1038/s41467-020-16616-8). To determine whether TBC1D15 stabilizes NOTCH1, CD133(+) TICs were transduced with shRNA lentivector against TBC1D15. Analysis by a co-IP Western blot analysis after introducing the NICD PEST domain deletion mutant into these cells showed no evidence of a protein band containing NICD (FIG. 1L). Rescue by over-expression of TBC1D15 in shTBC1D15-CD133(+) TICs restored interaction with the NICD PEST domain (FIG. 1L).

TBC1D15 bound with phosphotyrosine-binding (PTB) domain of NUMB: We further examined how TBC1D15 induces NUMB-mediated, NOTCH stability. The latter has three known, well-conserved aPKC (atypical protein kinase C) serine phosphorylation site. Although previous studies showed that TBC1D15 interacts directly with NUMB-3A (NUMB phosphorylation-null mutant) in transfected-CD133(+) TICs, it remains unclear as to which of the three significant serine residues of TBC1D15 are the site(s) of interaction. (That is, we also investigated the domain mapping study of NUMB and the presence or absence of NUMB phosphorylation, because the NUMB domain to which TBC1D15 binds and the mechanism for regulating NUMB phosphorylation are still unknown. To examine the direct interaction and determine which region is responsible for the interaction with Numb and TBC1D15, a cell-free in vitro binding assay was performed.) To identify the key serine residues of NUMB which interact with TBC1D15, NUMB domain deletion mutants were constructed and used (FIG. 10). GST-Numb deletion-fragments immobilized on beads were incubated with purified TBC1D15 protein (FIG. 1P). This experiment showed that TBC1D15 interacted with all GST-NUMB deletion constructs (GST-NUMB-full length, GST-NUMB-PTB, GST-NUMB-PRR/2, and GST-NUMB-PRR/3) with the exception of GST-NUMB-PRR/1. GST-NUMB-PTB showed significantly stronger signals than the other domains of NUMB (FIG. 1Q). These results indicated that the PTB domain of NUMB was responsible and required for optimal binding to TBC1D15.

Next, we investigated how TBC1D15-NICD binding affects the expression and phosphorylation of NUMB. To determine whether the regulation of NUMB expression and phosphorylation is TBC1D15 co-dependent or not, we used CD133-positive vs. CD133-negative TICs with TBC1D15 knockdown (KD) or overexpression (FIG. 2A). The mock-treated CD133(+) TICs expressed NUMB with/without TBC1D15 KD and was not phosphorylated. Likewise, CD133(−) TICs showed a similar expression pattern, for both NUMB and phosphorylated NUMB in mock-treated cells with/without TBC1D15 overexpression (FIG. 2A).

Recent studies indicated that NUMB alternative splicing is mis-regulated in various cancers. Expression of NUMB isoforms appears to modify the function of NUMB as an inhibitor of the NOTCH signaling pathway. Activation of the NOTCH pathway in both lung and breast cancer has been linked to global downregulation of NUMB at the protein level. The cellular expression of NUMB isoform mRNAs was examined to address a possibility of changes to NUMB isoform expression. This was accomplished by a semi-quantitative approach PCR approach in CD133(+) and CD133(−) TICs with or without TBC1D15 overexpression (FIG. 2G). In CD133(+) TICs, expression of all NUMB isoforms' mRNAs showed no distinct differences. However, the mRNA expression of NUMB isoforms 1, 3, 5 and 6 in CD133(−) TICs was lower than that in CD133(+) TICs. The expression of NUMB isoforms 1, 3, 5 and 6 was significantly increased relative to isoforms 2 and 4 in CD133(−) TICs with overexpressed TBC1D15.

The differences in NUMB isoform expression led us to investigate the effect of TBC1D15-NICD interactions with NUMB protein isoforms in CD133(+) TICs. When the NICD PEST domain was deleted in TBC1D15 KD CD133-positive TICs, alternative NUMB expression was observed (FIGS. 2A and 2G). Previous studies have established that NUMB protein is expressed as isoforms of approximately 74 kDa (NUMB isoforms 1 and 3), 72 kDa (NUMB isoforms 2 and 4), and 50 kDa (NUMB isoforms 5 and 6) kDa. Herein, the NUMB isoform that was observed in these cells was a 50 kDa species which we assigned to isoforms 5/6 and its expression was TBC1D15 dependent. (That is, through this result, we confirmed that the expression of NUMB isoform 5 is TBC1D15 dependent.)

We next assessed whether NUMB isoform 5 binds directly to TBC1D15. We performed cell-free in vitro binding assays and co-IP western blot in CD133(+) or (−) TICs combined with overexpression of full-length NUMB and NUMB isoforms 5, and 6 (FIGS. 2B and 2C). (That is, we overexpressed NUMB full-length, NUMB isoform 5, and NUMB isoform 6 in CD133-positive or -negative TICs, and then performed Co-IP western blot with TBC1D15 and cell-free in vitro binding assay.) Flag-tagged TBC1D15 protein strongly interacted with the NUMB isoform 5 in vitro (red arrowhead) (FIG. 2B). Other binding assays comparing NUMB full-length, isoform 5, and isoform 6 revealed that NUMB isoform 5 was important for the TBC1D15 interaction in CD133(+) TICs. In order to confirm whether TBD1D15 preferentially binds and induces phosphorylation with NUMB isoform 5, we performed co-IP in CD133(+) vs (−) TICs (FIG. 2C). We found that full-length NUMB and isoform 5 induced phosphorylation of NUMB. In addition, this protein-protein interaction was not found in CD133(−) TICs. (That is, as a result, we found that NUMB isoform 5 directly binds to TBC1D15.) In addition, we tested whether the trimeric TBC1D15-NUMB isoform 5-NICD complex was formed in CD133-positive TICs (FIG. 2D). These results indicated that the interaction of the TBC1D15-PEST domain of NICD activated NUMB isoform 5 phosphorylation via TBC1D15-aPKCζ-association.

NUMB Isoform 5 Co-Localized to the Cell Membrane and Mitochondria with TBC1D15 (NUMB Isoform 5 Stimulates Cell-Cell Contacts Site and Mitochondrial Localization of TBC1D15)

Next, we investigated the subcellular localization of TBC1D15 to compare its relationship to the functions of NUMB isoform 5 and full-length NUMB in CD133(+) TICs. Mammalian NUMB in polarized epithelial cells is known to be localized to the basolateral membrane. Furthermore, recent studies have shown that NUMB depletion accelerated mitochondrial fragmentation by promoting phosphorylation of Drp1, which in turn leads to mitochondrial dysfunction and apoptosis. In CD133(+) TICs, endogenous TBC1D15 showed punctate staining throughout the cytoplasm with accumulation at the cell membrane (FIGS. 2E and 2H). Under this condition, GFP-full-length NUMB is localized to sites at the cell membrane. GFP-NUMB isoform 5 was observed to accumulate in the cytoplasm and cell membrane in a manner similar to endogenous TBC1D15 as evident from overlapping immunostaining. In contrast, this was not observed with GFP-NUMB isoform 6. (When the cells were co-stained for TBC1D15, NUMB overlapped with these molecules at intercellular adhesion site. These data indicate that TBC1D15 localizes to intercellular adhesion site with NUMB isoform 5.)

We next investigated whether TBC1D15 specifically interacts with NUMB isoform 5 to induce recruitment of the former to mitochondria. Indeed, this was established by the observed co-localization with the mitochondrial marker (TOM20 and FIS1) (FIG. 2F). In addition, we investigated the intracellular localization and activity of NICD when the TBC1D15-NUMB isoform 5 complexes were recruited to mitochondria.

Figure 3A:
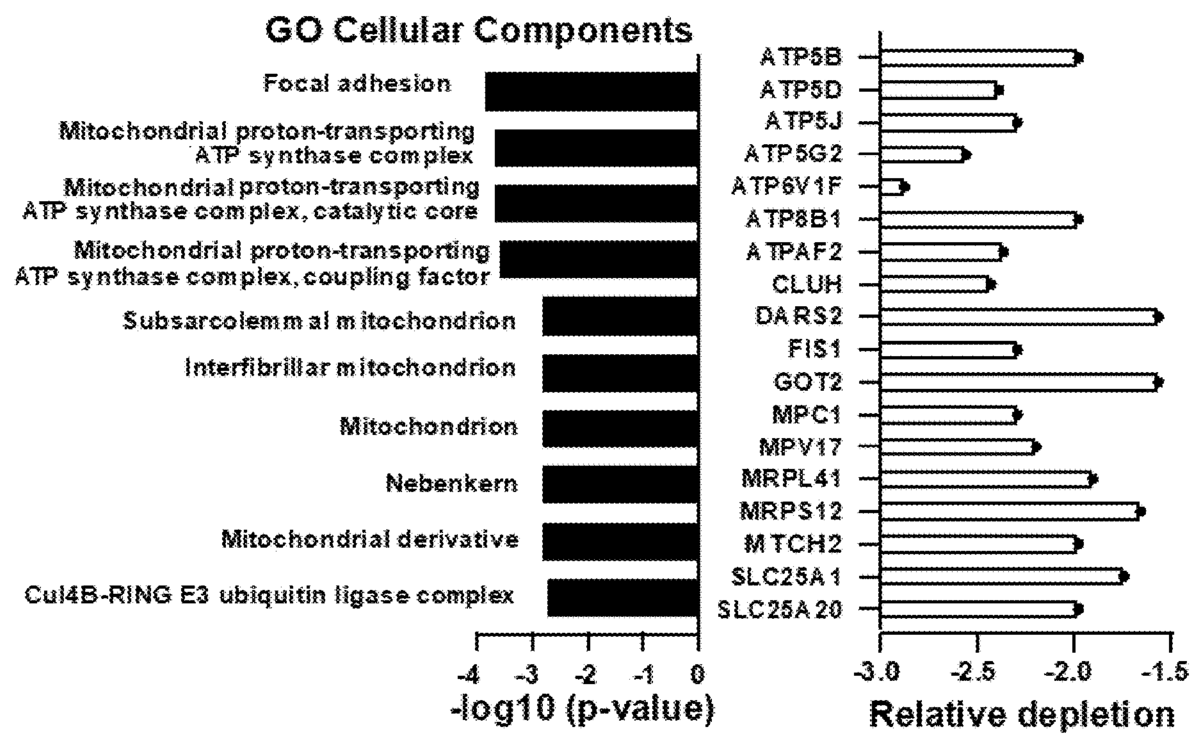
Figure 3A:
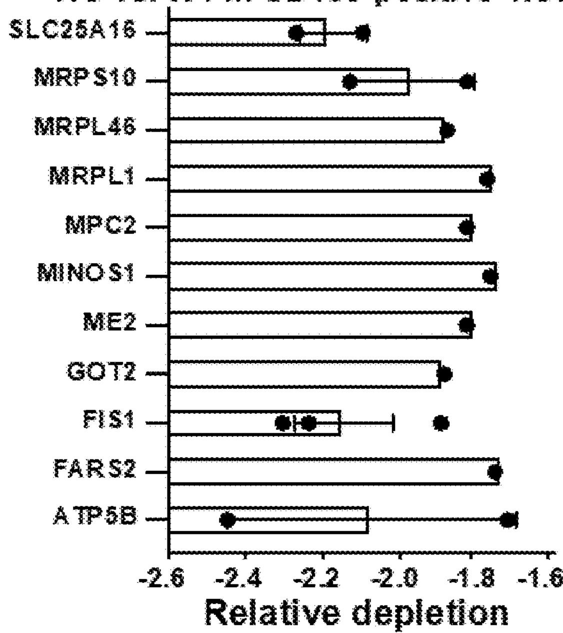

TBC1D15-NICD Interaction Increases Mitochondrial Number and Recruits Mitochondria to the Nucleus In a previous study through NANOG ChIP (chromatin immunoprecipitations)-seq analysis, we showed that NANOG regulates the expression of genes related to mitochondrial metabolic pathways required to maintain TICs (Chen et al., *Cell Metab* (2016) 23, 206-219. 10.1016/j.cmet.2015.12.004). To gain an understanding of the direct gene targets of NOTCH1, ChIP-seq experiments were performed using anti-NOTCH1 antibodies with CD133(+) and (−) TICs. Herein, we investigated the expression of genes related to the mitochondrial metabolic pathways following the expression of TBC1D15 through NOTCH1 ChIP-seq analysis (FIG. 3A). The gene ontology (GO) results indicated that CD133(+) TICs showed altered gene expression of proteins involved in mitochondrial metabolic-related pathways, such as mitochondrial proton-transporting ATP synthase complex, mitochondrial structure and morphology, and other related gene families (Table 1 and FIG. 3A). Mitochondrial metabolic-related signals in CD133(+) vs. (−) TICs and TBC1D15 KO vs. WT of CD133(+) TICs were compared for differences, followed by GO analysis of corresponding gene expression changes (FIG. 3A, Tables 2 and 3). These results demonstrated that TBC1D15 and NOTCH1 may play important roles in the regulation of mitochondrial metabolic pathways in CD133(+) TICs.

Figure 3B:
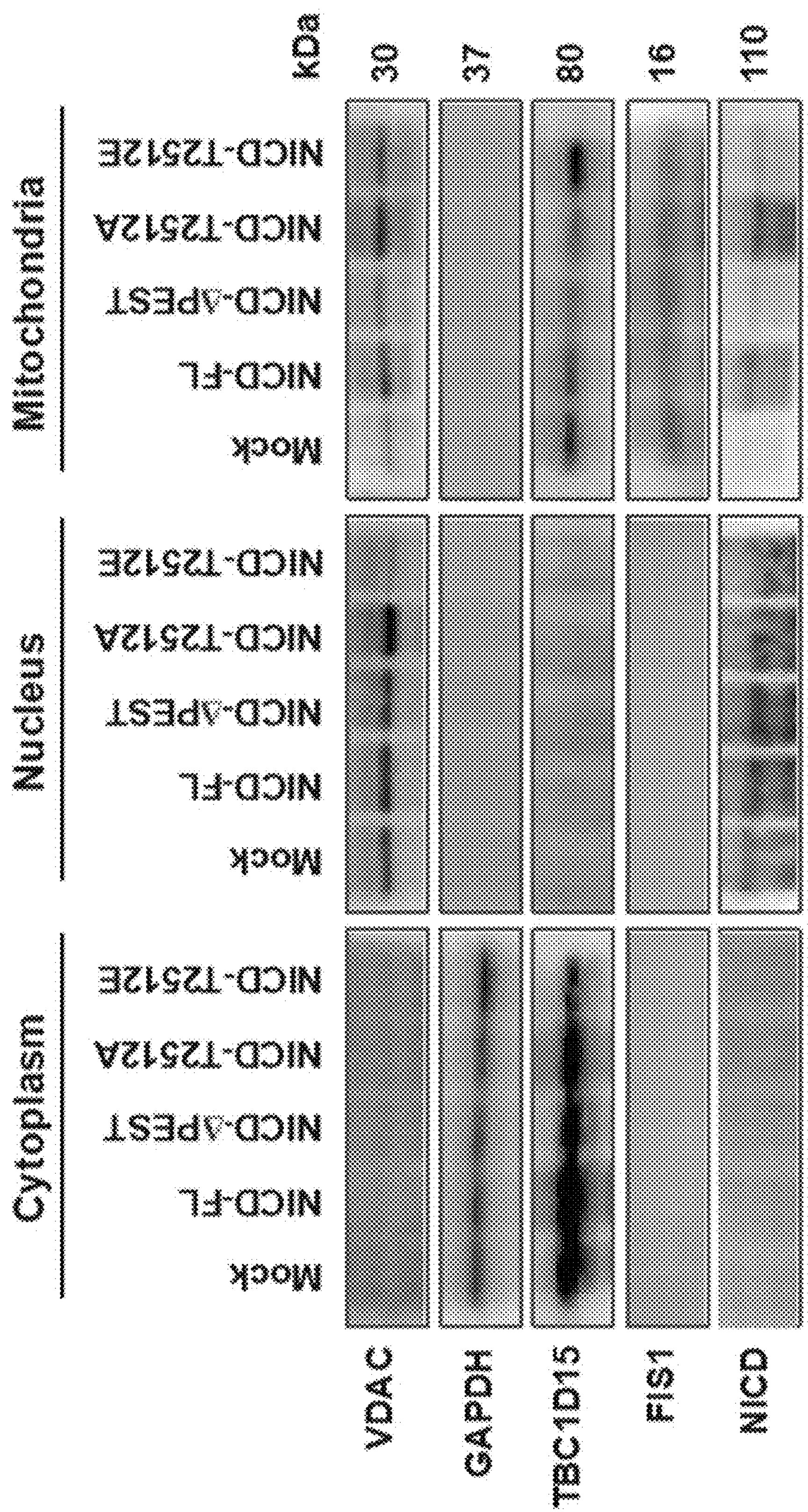
Figure 3C:
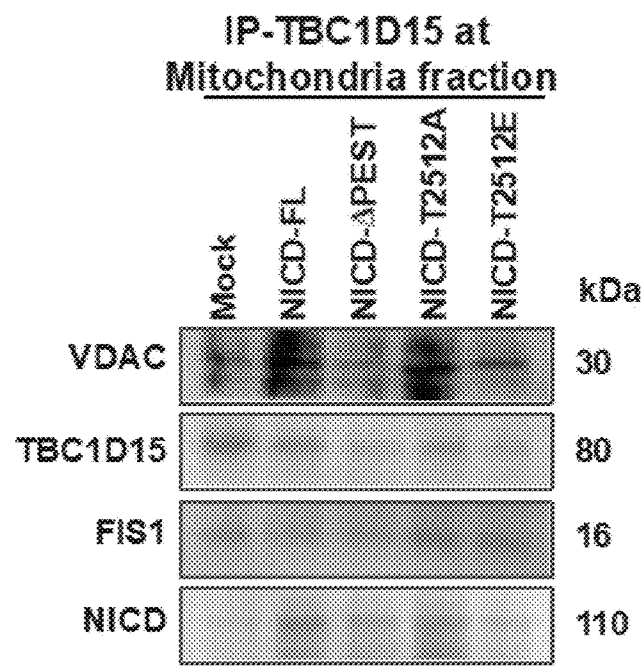
Figure 3D:
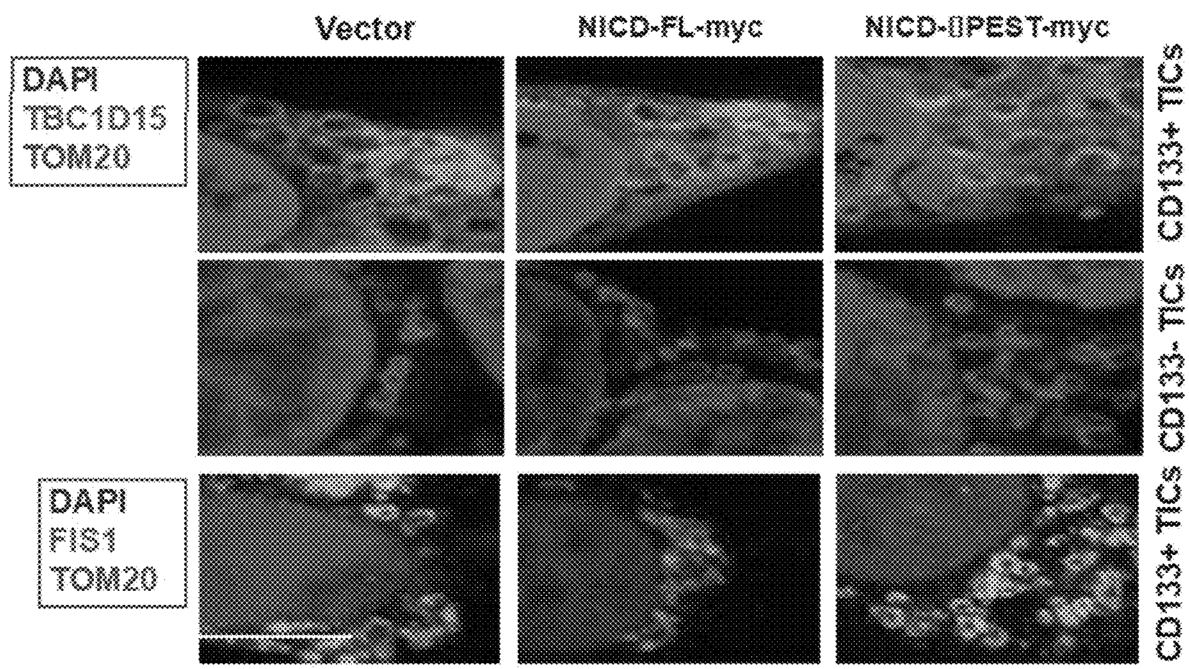
Figure 3G:
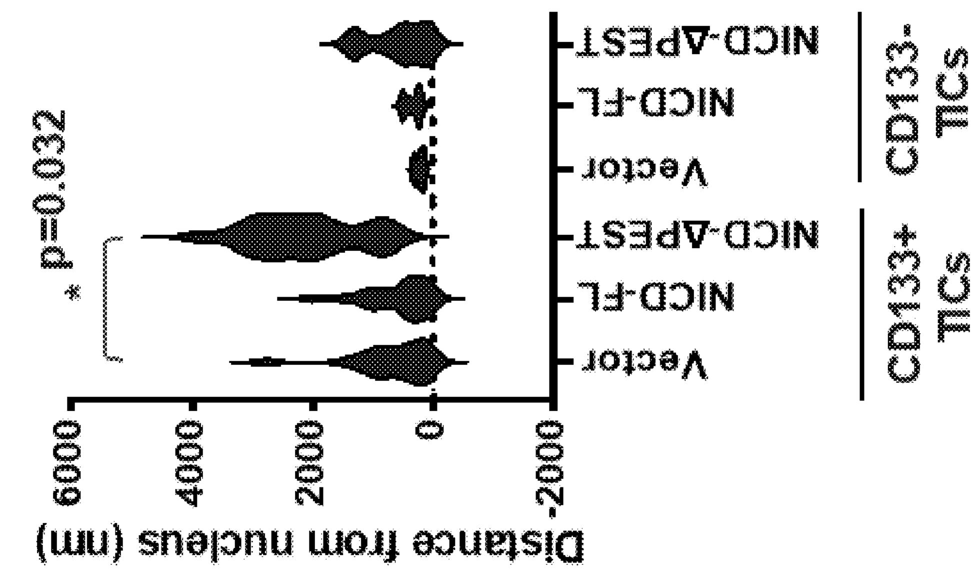
Figure 3F:
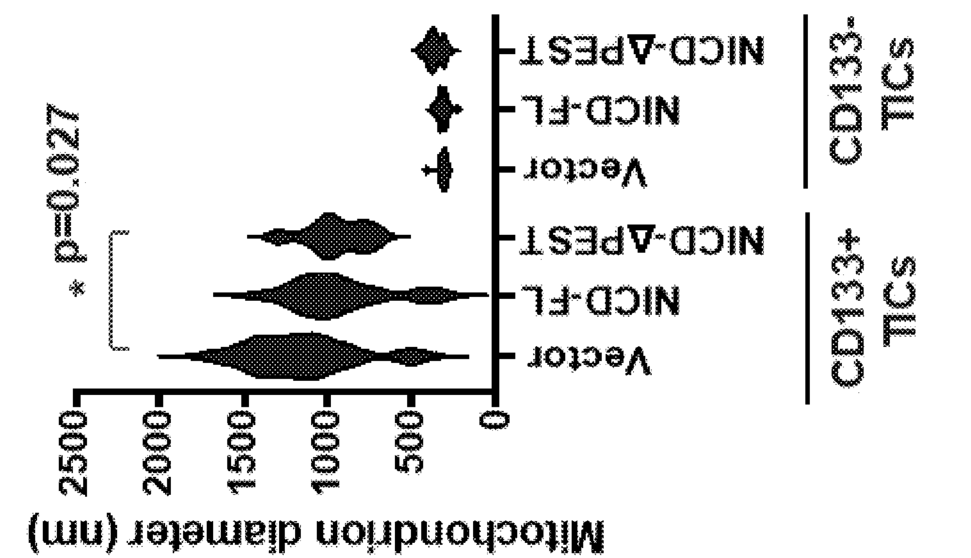
Figure 3E:
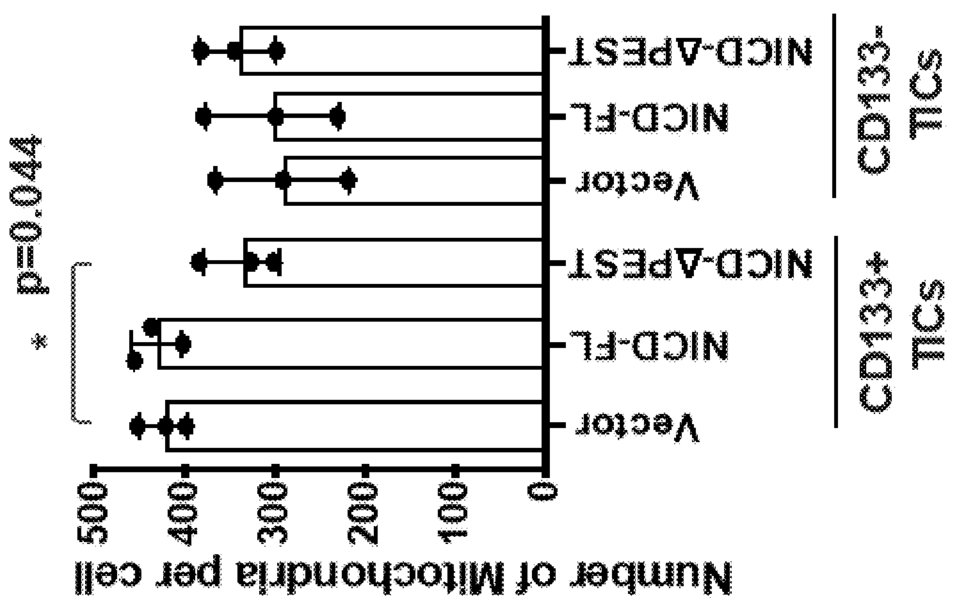

We next investigated the effect of interactions between TBC1D15 with PEST on the mitochondria of CD133(+) TICs. TBC1D15 and NICD were localized in mitochondrial fractions of CD133(+) TICs transfected with NICD mutants (FIG. 3B). In addition, the localization of TBC1D15 and NICD decreased in the mitochondrial fraction as indicated using anti-TBC1D15 (FIG. 3C) and showed an expression pattern similar to that observed by cellular fractionation (FIG. 3B). Next, we investigated the mitochondrial recruitment of endogenous TBC1D15 to NICD-PEST. Surprisingly, using confocal imaging of mitochondria marker TOM20 and TBC1D15, we found that mitochondrial sizes, numbers, and subcellular distribution differed between CD133(+) TICs and CD133(−) TICs (FIG. 3D). In CD133 (+) TICs, the number and sizes of mitochondria increased, and it was found that the mitochondria had a pronounced perinuclear localization (FIGS. 3E-3G). However, in CD133 (+) TICs, expressing the NICD-PEST domain deletion mutant, the number of mitochondria was reduced compared to NICD-FL expressing cells, additionally, the size was noticeably reduced to a small and constant size.

In CD133(−) TICs, compared to CD133(+) TICs, the mitochondrial numbers were fewer, more evenly distributed in the cytoplasm with a uniformly smaller size. In CD133(−) TICs expressing the NICD-PEST deletion mutant, the number of mitochondria was reduced in comparison to CD133 (+) TICs in addition to exhibiting a smaller size and a peri-nuclear localization (FIGS. 3E-3G). These data indicated that the binding of TBC1D15 to NICD-PEST resulted in recruitment to the mitochondria.

Figure 3H:
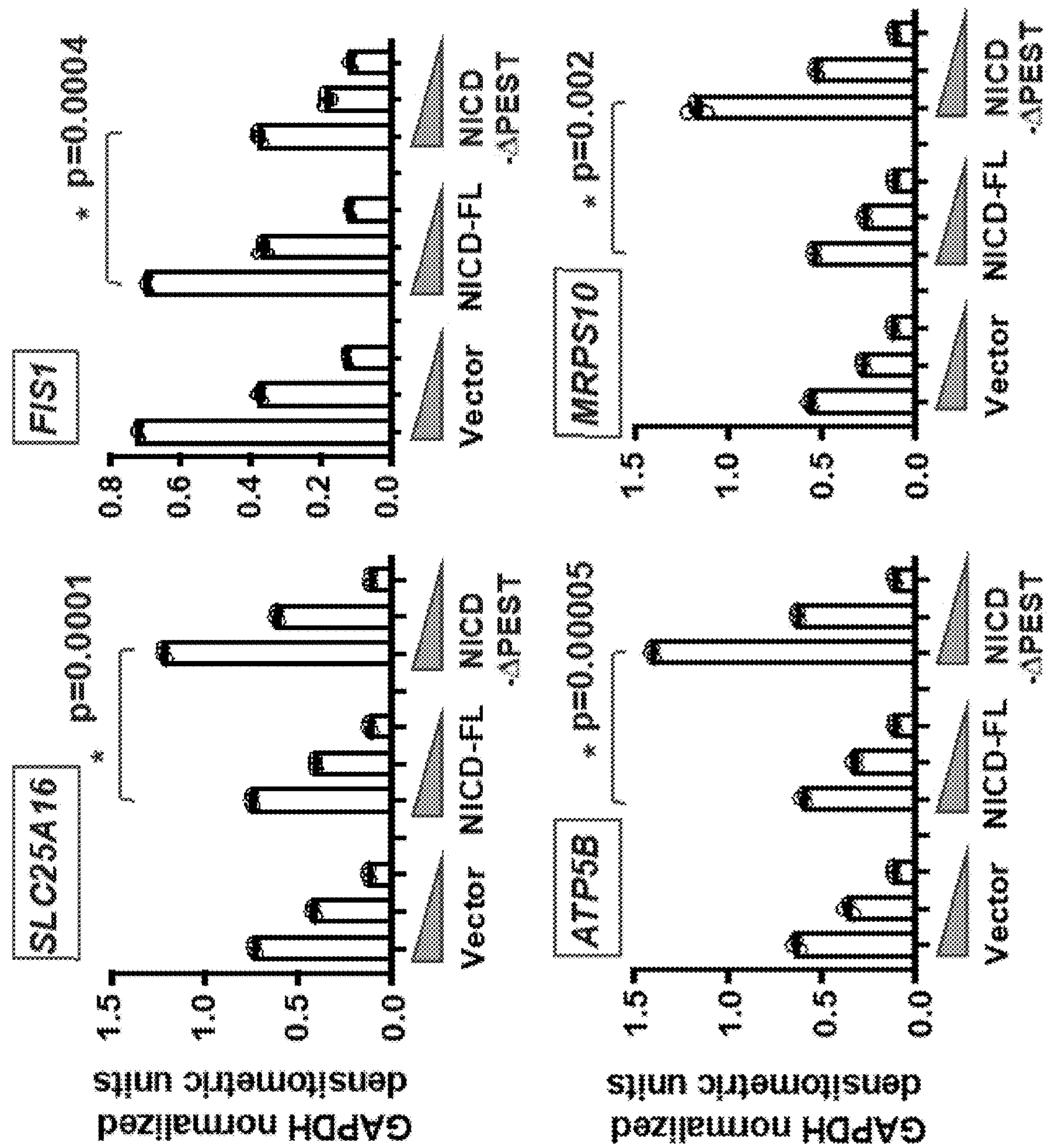

Changes to mitochondrial metabolism-related genes (SLC25A16, ATP5B, and MRPS10) showed de-repression in CD133(+) TICs with NICD-PEST deletion mutation compared to NICD-FL (FIG. 3H). These results suggested that TBC1D15 plays a role in the generation and expansion of liver TICs by increasing mitochondrial number, increased expression of metabolic enzymes, and recruitment of mitochondria to a perinuclear localization.

TABLE 1

List of cellular components (showing the top 10 ranked) by p-value by gene ontology analysis in ChIP-qPCR with anti-NOTCH1 in CD 133-positive vs. negative TICs.

| Rank | Term | p-value | q-value | Genes |
|---|---|---|---|---|
| 1 | Focal adhesion (GO:0005925) | 0.000143 | 0.035426 | [GRB7, ACTR2, MME, LRP1, GDI2, LMO7, SORBS3, RND3, CORO1B, ADD1, DCAF6, RPL7, ACTG1, HSP90B1, CSRP2, YWHAQ, PALLD, DLC1, GNA12, PIP5K1A, RPL27, RPL18, LIMS1] |
| 2 | Mitochondrial proton-transporting ATP synthase complex (GO:0005753) | 0.000216 | 0.035426 | [ATP5B, ATP5D, ATP5C1, ATP5J, ATP5G2] |
| 3 | Mitochondrial proton-transporting ATP synthase complex, catalytic core F(1) (GO:0000275) | 0.000216 | 0.035426 | [ATP5B, ATP5D, ATP5C1, ATP5J, ATP5G2] |
| 4 | Mitochondrial proton-transporting ATP synthase complex, coupling factor F(o) (GO:0000276) | 0.000274 | 0.035426 | [ATP5B, ATP5D, ATP5C1, ATP5J, ATP5G2] |
| 5 | Subsarcolemmal mitochondrion (GO:1990843) | 0.001607 | 0.092517 | [MRS2, MTCH2, NAXE, ECI2, ATP5C1, ATP5J, ETFA, ABCB8, PTS, MRPL41, ATP5B, NADK2, MPC1, FAM162A, ATP5D, MPV17, HARS, SLC25A20, JARID2, COX10, NKTR, POLG, CASP8AP2, FIS1, STARD5, MDH1, GK, OXSM, GOT2, MRPS18B, DARS2, TRNT1, SIRT3, PNKD, UQCRQ, NDUFS5, PCCB, OGDH, NDUFS2, SUCLG1, MXD1] |
| 6 | Interfibrillar mitochondrion (GO:1990844) | 0.001607 | 0.092517 | [MRS2, MTCH2, NAXE, ECI2, ATP5C1, ATP5J, ETFA, ABCB8, PTS, MRPL41, ATP5B, NADK2, MPC1, FAM162A, ATP5D, MPV17, HARS, SLC25A20, JARID2, COX10, NKTR, POLG, CASP8AP2, FIS1, STARD5, MDH1, GK, OXSM, GOT2, MRPS18B, DARS2, TRNT1, SIRT3, PNKD, UQCRQ, NDUFS5, PCCB, OGDH, NDUFS2, SUCLG1, MXD1] |
| 7 | Mitochondrion (GO0:0005739) | 0.001607 | 0.092517 | [MRS2, MTCH2, NAXE, ECI2, ATP5C1, ATP5J, ETFA, ABCB8, PTS, MRPL41, ATP5B, NADK2, MPC1, FAM162A, ATP5D, MPV17, HARS, SLC25A20, JARID2, COX10, NKTR, POLG, CASP8AP2, FIS1, STARD5, MDH1, GK, OXSM, GOT2, MRPS18B, DARS2, TRNT1, SIRT3, PNKD, UQCRQ, NDUFS5, PCCB, OGDH, NDUFS2, SUCLG1, MXD1] |
| 8 | Nebenkern (GO:0016006) | 0.001607 | 0.092517 | [MRS2, MTCH2, NAXE, ECI2, ATP5C1, ATP5J, ETFA, ABCB8, PTS, MRPL41, ATP5B, NADK2, MPC1, FAM162A, ATP5D, MPV17, HARS, SLC25A20, JARID2, COX10, NKTR, POLG, CASP8AP2, FIS1, STARD5, MDH1, GK, OXSM, GOT2, MRPS18B, DARS2, TRNT1, SIRT3, PNKD, UQCRQ, NDUFS5, PCCB, OGDH, NDUFS2, SUCLG1, MXD1] |

TABLE 1-continued

List of cellular components (showing the top 10 ranked) by p-value by gene ontology analysis in ChIP-qPCR with anti-NOTCH1 in CD 133-positive vs. negative TICs.

| Rank | Term | p-value | q-value | Genes |
|---|---|---|---|---|
| 9 | Mitochondrial derivative (GO:0016007) | 0.001607 | 0.092517 | [MRS2, MTCH2, NAXE, ECI2, ATP5C1, ATP5J, ETFA, ABCB8, PTS, MRPL41, ATP5B, NADK2, MPC1, FAM162A, ATP5D, MPV17, HARS, SLC25A20, JARID2, COX10, NKTR, POLG, CASP8AP2, FIS1, STARD5, MDH1, GK, OXSM, GOT2, MRPS18B, DARS2, TRNT1, SIRT3, PNKD, UQCRQ, NDUFS5, PCCB, OGDH, NDUFS2, SUCLG1, MXD1] |
| 10 | Cu14B-RING E3 ubiquitin ligase complex (GO:0031465) | 0.001917 | 0.098918 | [CUL5, DTL, DCAF7, DCAF6] |

TABLE 2

List of cellular components by gene ontology analysis in ChIP-qPCR with anti-NOTCH1 in CD133-positive TICs with/without TBC1D15 KD vs. WT. Table showing the top 10 ranked by p-value.

| Rank | Term | p-value | q-value | overlap_genes |
|---|---|---|---|---|
| 1 | Mitochondrial matrix (GO: 0005759) | 6.48E−09 | 1.75E−07 | [ALAS1, GOT2, ETFA, PDHB, ACADM, ME2, ACSF2, FARS2] |
| 2 | Intracellular organelle lumen (G0: 0070013) | 5.74E−06 | 7.75E−05 | [ALAS1, GOT2, ETFA, PDHB, ACADM, ME2, ACSF2, FARS2] |
| 3 | Mitochondrial membrane (GO: 0031966) | 1.95E−05 | 1.76E−04 | [SLC25A16, MRPL1, CYCS, MRPS10, ACADM, MRPL46] |
| 4 | Mitochondrial inner membrane (G0: 0005743) | 4.67E−05 | 3.15E−04 | [SLC25A16, MRPL1, CYCS, MRPS10, MRPL46] |
| 5 | Organelle inner membrane (GO: 0019866) | 6.02E−05 | 3.25E−04 | [SLC25A16, MRPL1, CYCS, MRPS10, MRPL46] |
| 6 | Integral component of mitochondrial membrane (GO: 0032592) | 3.06E−03 | 1.38E−02 | [FIS1, MPC2] |
| 7 | Mitochondrial envelope (G0: 0005740) | 1.09E−02 | 3.74E−02 | [CYCS, ACADM] |
| 8 | Peroxisome (G0: 0005777) | 1.11E−02 | 3.74E−02 | [FIS1, EHHADH] |
| 9 | Integral component of peroxisomal membrane (GO: 0005779) | 1.61E−02 | 4.69E−02 | [FIS1] |
| 10 | Intrinsic component of peroxisomal membrane (GO: 0031231) | 1.74E−02 | 4.69E−02 | [FIS1] |

TABLE 3

List of enriched anti-NOTCH1/NANOG ChiP-seq-based mitochondrial relate genes in CD133-positive TICs with TBC1D15 KD vs WT.

| Feature Gene | Description transcript | Start peak | End peak | Probe strand | Pro-moter | Relative enrichment | Fold depletion |
|---|---|---|---|---|---|---|---|
| Anti-NOTCH1 TBC1D15 KO vs WT in CD133-positive TICs | | | | | | | |
| Atp5b | ATP synthase H+ transporting mitochondrial F1 complex, beta subunit [Source: MGI Symbol; Acc: MGI: 107801] | 128086681 | 128088681 | + | | 2.445995 | 3.9267337 |
| Fis1 | fission, mitochondrial 1 [Source: MGI Symbol; Acc: MGI: 1913687] | 136961845 | 136963845 | + | | 2.3033295 | 4.2162404 |
| Slc25a16 | solute carrier family 25 (mitochondrial carrier Graves disease autoantigen) member 16 [Source: MGI Symbol; Acc: MGI: 1920382] | 62946026 | 62948026 | + | Yes | 2.267997 | 3.7568085 |
| Fis1 | fission, mitochondrial 1 [Source: MGI Symbol; Acc: MGI: 1913687] | 136961433 | 136963433 | + | | 2.2374082 | 4.457248 |
| Mrps10 | mitochondrial ribosomal protein S10 [Source: MGI Symbol; Acc: MGI: 1928139] | 47367891 | 47369891 | + | Yes | 2.1304934 | 3.7568085 |
| Slc25a16 | solute carrier family 25 (mitochondrial carrier Graves disease autoantigen) member 16 [Source: MGI Symbol; Acc: MGI: 1920382] | 62946075 | 62948075 | + | Yes | 2.0980718 | 3.9267337 |
| Fis1 | fission, mitochondrial 1 [Source: MGI Symbol; Acc: MGI: 1913687] | 136961077 | 136963077 | + | | 1.8960276 | 4.7568088 |
| Got2 | glutamatic-oxaloacetic transaminase 2 mitochondrial [Source: MGI Symbol; Acc: MGI: 95792] | 95867045 | 95869045 | − | | 1.8865674 | 3.9267337 |
| Mrpl46 | mitochondrial ribosomal protein L46 [Source: MGI Symbol; Acc: MGI: 1914558] | 78777366 | 78779366 | − | | 1.8789549 | 4.078737 |
| Mpc2 | mitochondrial pyruvate carrier 2 [Source: MGI Symbol; Acc: MGI: 1917706] | 165466500 | 165468500 | + | | 1.8085651 | 3.3417711 |
| Me2 | malic enzyme 2, NAD(+)-dependent mitochondrial [Source: MGI Symbol; Acc: MGI: 2147351] | 73814392 | 73816392 | − | Yes | 1.8085651 | 4.7568088 |
| Mrps10 | mitochondrial ribosomal protein S10 [Source: MGI Symbol; Acc: MGI: 1928139] | 47368197 | 47370197 | + | Yes | 1.8085651 | 4.078737 |
| Mrpl1 | mitochondrial ribosomal protein L1 [Source: MGI Symbol; Acc: MGI: 2137202] | 96208493 | 96210493 | + | | 1.7560978 | 4.5641637 |

TABLE 3-continued

List of enriched anti-NOTCH1/NANOG ChiP-seq-based mitochondrial relate genes in CD133-positive TICs with TBC1D15 KD vs WT.

| Feature Gene | Description transcript | Start peak | End peak | Probe strand | Pro-moter | Relative enrichment | Fold depletion |
|---|---|---|---|---|---|---|---|
| Minos1 | mitochondrial inner membrane organizing system 1 [Source: MGI Symbol; Acc: MGI: 1913628] | 139130113 | 139132113 | − | Yes | 1.7471647 | 4.341771 |
| Fars2 | phenylalanine-tRNA synthetase 2 (mitochondrial) [Source: MGI Symbol; Acc: MGI: 1917205] | 36458280 | 36460280 | − | | 1.7345643 | 4.078737 |
| tp5b | ATP synthase H+ transporting mitochondrial F1 complex, beta subunit [Source: MGI Symbol; Acc: MGI: 107801] | 128087552 | 128089552 | + | | 1.7016501 | 4.5641637 |
| | Anti-NANOG TBC1D15 KO vs WT in CD133-positive TICs | | | | | | |
| Atp6v1c2 | ATPase, H+ transporting, lysosomal V1 subunit C2 | 17323665 | 17325665 | − | Yes | 3.2333727 | 5.286448 |
| Atp6v1c2 | ATPase, H+ transporting, lysosomal V1 subunit C2 | 17323703 | 17325703 | − | Yes | 3.1860666 | 5.239142 |
| Atp8b4 | ATPase, class I, type 8B, member 4 | 126490573 | 126492573 | − | | 1.9345276 | 5.139606 |
| Atp8b2 | ATPase, class I, type 8B, member 2 | 89953639 | 89955639 | − | | 1.8276126 | 5.032691 |
| Me3 | malic enzyme 3, NADP(+)-dependent, mitochondrial | 89828282 | 89830282 | + | | 3.2333727 | 5.286448 |
| Immp2l | IMP2 inner mitochondrial membrane peptidase-like (*S. cerevisiae*) | 41544391 | 41546391 | + | | 2.985154 | 5.1902323 |
| Diablo | diablo, IAP-binding mitochondrial protein | 123517231 | 123519231 | + | | 2.8820603 | 5.0871387 |
| Mecr | mitochondrial trans-2-enoyl-CoA reductase | 131859233 | 131861233 | + | | 2.297098 | 5.5021763 |
| Atp5h | ATP synthase, H+ transporting, mitochondrial F0 complex, subunit D | 115416018 | 115418018 | − | | 2.2146356 | 5.419714 |
| Mtus1 | mitochondrial tumor suppressor 1 | 41053794 | 41055794 | − | | 1.9345276 | 5.139606 |
| Cmpk2 | cytidine monophosphate (UMP-CMP) kinase 2, mitochondrial | 26472930 | 26474930 | + | | 1.8820603 | 5.0871387 |
| Slc25a26 | solute carrier family 25 (mitochondrial carrier, phosphate carrier), member 26 | 94533140 | 94535140 | + | | 1.8276126 | 5.032691 |

Effects of TBC1D15 on PEST Domain Phosphorylation

NOTCH1 activation is regulated by phosphorylation and ubiquitination of CDK8. Mastermind promotes recruitment of the cyclin C-CDK8 complex and hyperphosphorylation of the PEST domain of NOTCH1. Although other kinases such as cyclin C and various CDKs (e.g., CDK3, CDK8 and CDK19) have been described to regulate NICD by phosphorylation of the PEST domain, the previous requirement of threonine 2512 (T2512) phosphorylation needed for Fbw7 interactions has been described in the literature.

To confirm the phosphorylation of PEST domain by cyclin C-CDK8 complex and TBC1D15, we investigated the interaction between CDK8 and TBC1D15 (FIG. 4A). Co-immunoprecipitation and immunoblot analysis of CDK8 and TBC1D15 revealed that they strongly interacted with the PEST domain of TBC1D15. Conversely, overexpression of CDK8 strongly suppressed NICD levels (FIG. 4B). These observations indicated that TBC1D15 controlled NICD levels through its interacting partners CDK8 and CDK19. The functional significance of the specific phosphorylation sites within the PEST domain was determined from NICD mutants (dominant negative Ala substitutions (S2490A, S2493A, S2500A, T2512A, S2514/2517A) vs. phosphomimetic T2512E or S2514E replacements). These recombinant proteins were expressed and purified and used for in vitro protein kinase assays with cell lysates. We found that TBC1D15 and CDK8 complexes could phosphorylate NICD (FIG. 4C). (Fbw7 bound to the peptide corresponding to NICD-PEST residues 2488-2517 is expected to induce 5 sites that were phosphorylated (FIG. 4C, Top panel). Co-IP western blot analysis of MYC-tag revealed interaction with threonine 2512 (T2512) and mutants of PEST domain (FIG. 4C, bottom). Moreover, CDK8 interacted with T2512.)

The NICD-PEST Domain Amino Acids T2512 and S2514 Region Comprises an Fbw7 Phospho-Degron Phosphorylation of the PEST domain converts it to a substrate for recognition by Fbw7, and Fbw7 binds directly to NICD promoting the polyubiquitination and proteasomal degradation of NICD by recruiting the components of an SCF ubiquitin ligase degradation complex.

The PEST domain of NICD is known to regulate protein stability and is a hot spot for mutations. NUMB binds the NICD-PEST domain to recruit the E3 ubiquitin ligases, ITCH and Fbw7 for ubiquitination and subsequent degradation of NOTCH/NICD. As TBC1D15 interacts with NUMB isoform 5, our results indicated that TBC1D15 interfered with NUMB isoform 5-mediated NOTCH1/NICD degradation by binding to the same PEST domain to prevent ubiquitination and degradation.

Furthermore, Fbw7 binding to NOTCH is dependent on an intact PEST domain, strongly indicating that the NOTCH CPD lies within this region. "CPD" refers to phosphopeptide binding motif for Cdc4, termed the Cdc4 phospho-degron. Alignment of the human NOTCH1 PEST domain with other Fbw7 substrates demonstrated a CPD consensus motif anchored around T2512. For this reason, we assessed whether two known NICD E3 ubiquitin ligase contributed to NICD-mediated degradation.

Figure 5A:
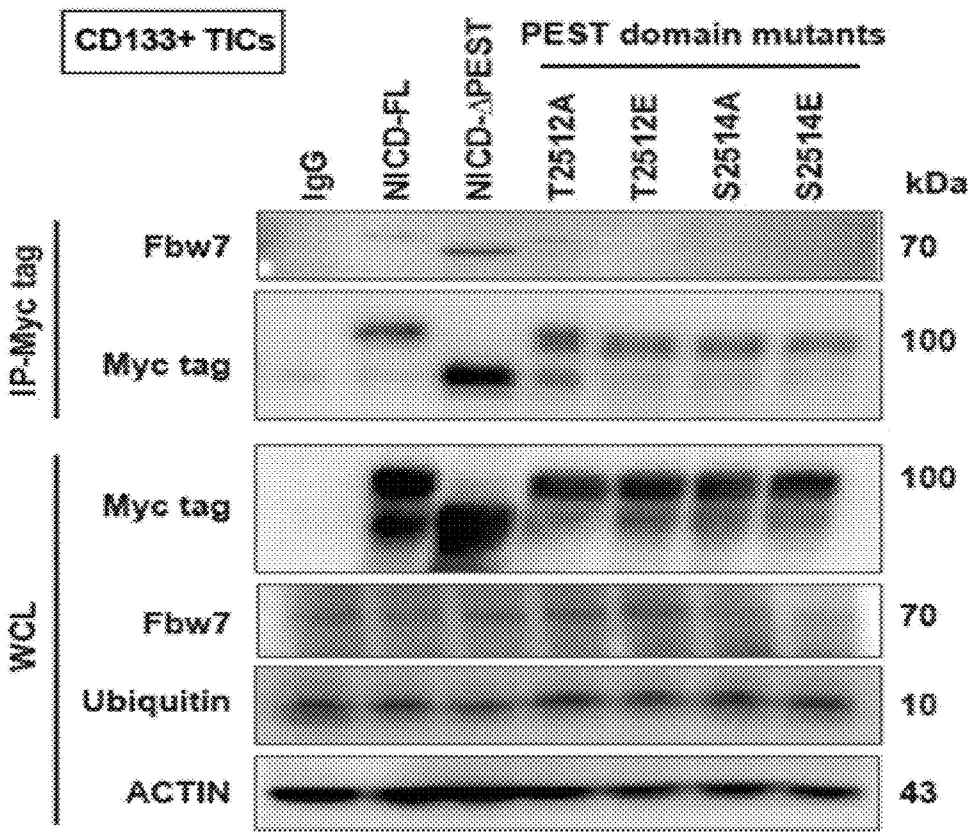

We overexpressed Flag-Fbw7 (FIG. 5A-5D) to determine if the T2512 and S2514 region contained a functional NOTCH CPD. We then examined the role of these phosphorylation sites in binding interactions between the NICD and Fbw7. We found that the T2512A and S2514A NICD mutants showed markedly decreased binding to Fbw7 when compared with NICD-FL (FIG. 5A). (Because CDK8 sites in the T2512 and 52514 region have been previously implicated in NOTCH degradation by Fbw7, we also tested the role of these residues in Fbw7 binding. We found that Fbw7 binding was disrupted by the T2512A and S2514A mutations and that binding was restored when T2512A and S2514A was replaced by a phosphor-mimetic residue (T2512E and S2514E) (FIG. 5A).)

Figure 5B:
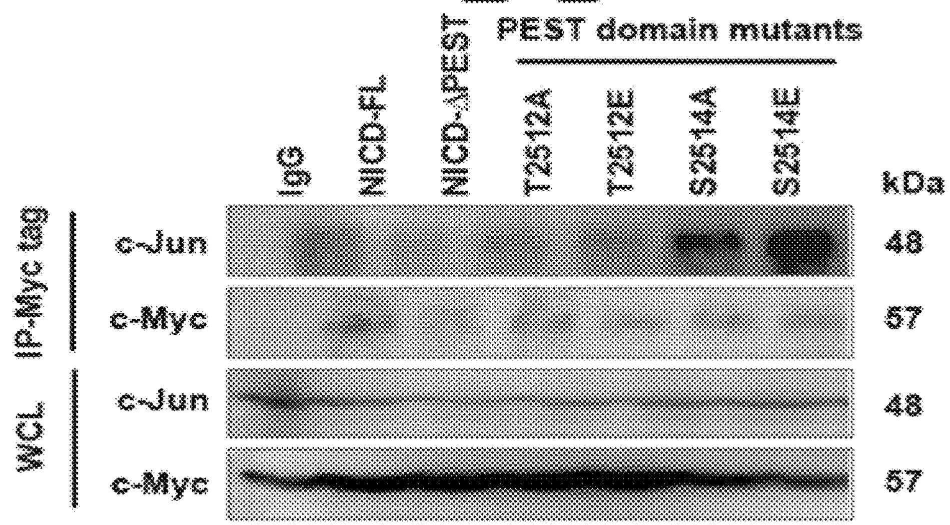
Figure 5C:
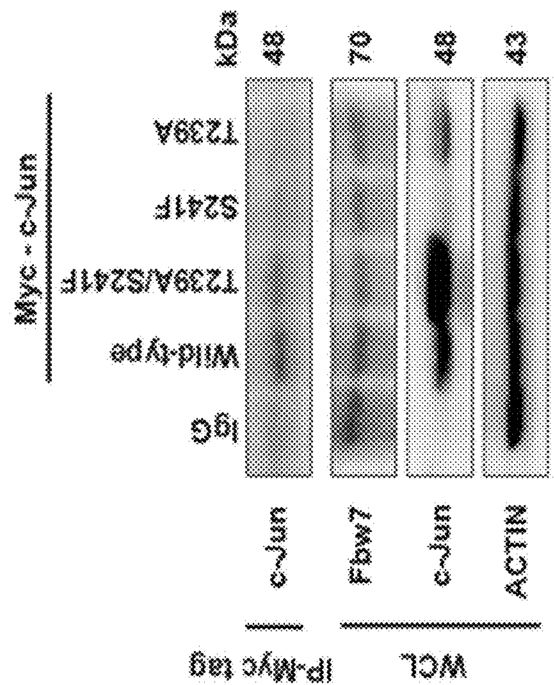
Figure 5D:
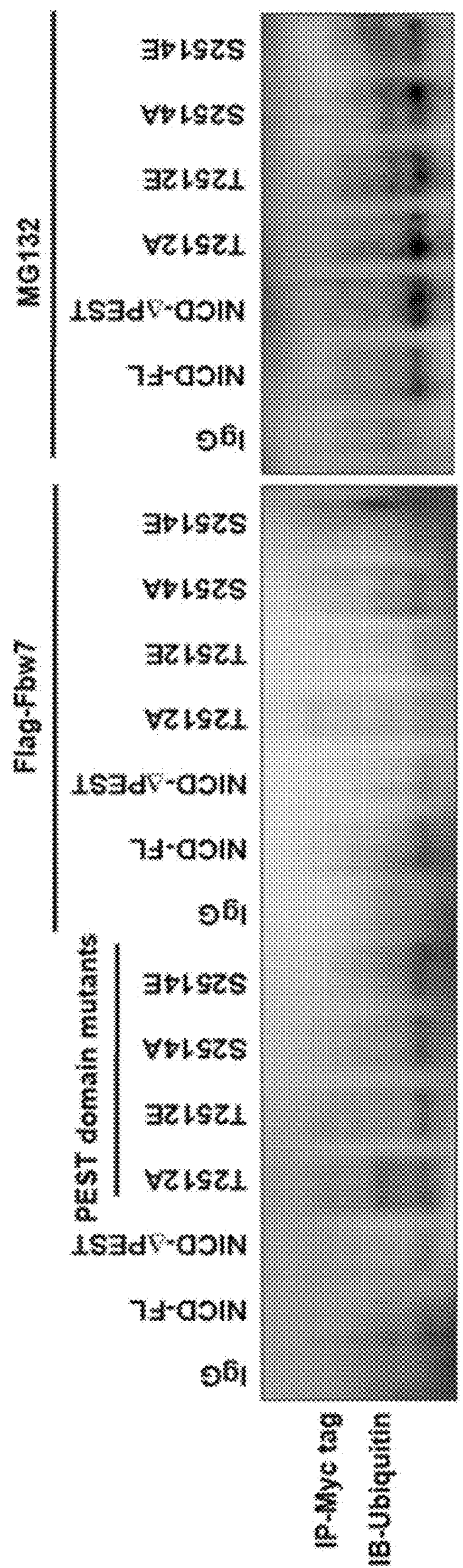

Previous reports showed that the CPD consensus motif is anchored around T2512 in human NOTCH1. This residue is highly conserved across all species of the NOTCH family. Also, these CPD consensus motif are present in c-Jun, c-Myc and cyclin E (FIG. 5B). As a positive control for Fbw7 binding to other CPD sites, we tested our experimental conditions with c-Jun and c-Myc which are known to contain the CPD which binds the NICD PEST domain. We performed IP assay (FIG. 5C) using anti-Fbw7 antibody after incubation with a peptide corresponding to c-Jun residues 229-253. This sequence region spans the putative Fbw7 binding site of c-Jun and is dependent on both Thr-239 and Ser-243 phosphorylation. As shown in FIG. 5C, wild-type c-Jun was co-precipitated with Fbw7 whereas the double amino acid substitution of T239A/S241F reduced the amount of c-Jun binding to Fbw7.

We next examined the role of T2512 of NICD in directing endogenous FBW7-mediated NICD ubiquitination. In accord with our binding studies, we found that the T2512A mutation markedly reduced NICD ubiquitination (FIG. 5D), indicating that T2512 phosphorylation promotes degradation while dephosphorylation of NOTCH T2512 stabilizes NICD.

Identification of Small Molecule Inhibitors

Figure 7C:
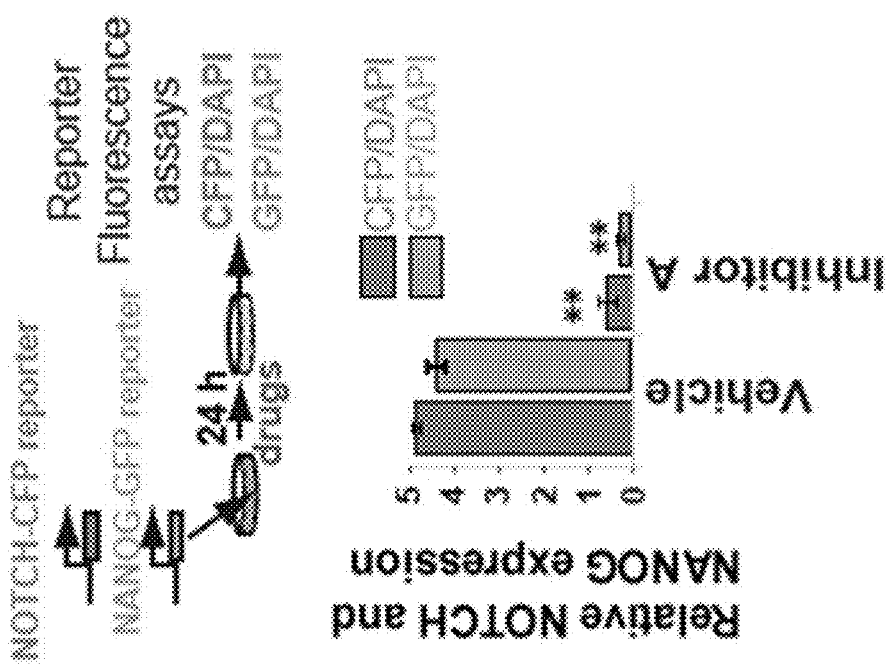
Figure 7C:
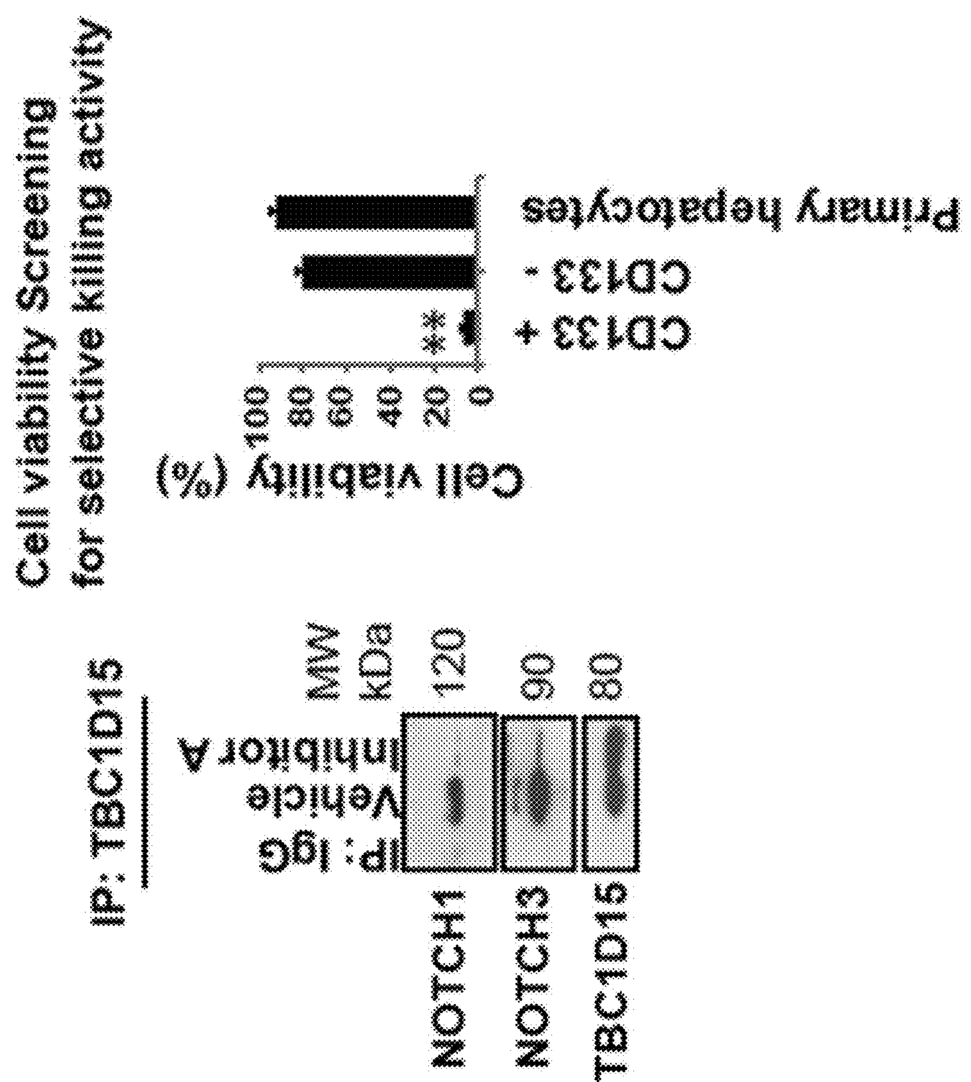

Based on our experimental studies and the results above, we conceive that interactions of TBC1D15 antagonists with NICD would decrease tumor incidence. To screen for small molecule inhibitors, FITC-tagged NOTCH1-TBC1D15 binding-domain peptide (wild type) or Y->A mutant of this peptide were synthesized to perform fluorescence polarization assay with recombinant TBC1D15 for the purpose of screening of a small molecule library (FIGS. 7A and 7B). The mutant peptide served as a negative control which cannot interact with TBC1D15. This powerful approach allowed for screening of 10,000 compounds to narrow the library of potential candidates to 630 compounds. We used other chemical libraries including the NCI/DTP Open Chemical Repository, the FDA-approved drug library (Enzo), Specs, and the Chembridge collection, to screen other compounds that are predicted to bind this interface with high affinity. Additional simulations were performed to generate intermediate structural models for a structure-based screening approach. High-ranking ligands (630 compounds) were passed to two different biological screening assays to identify the inhibitors that perform well in: 1) CD133-positive TICs viability screening with CD133-negative TICs as a control, and 2) use of HEY1-CFP and NANOG-GFP reporters in the Huh7 cell line for further screening (to select the top 10% candidates which downregulated both reporters). The latter reporter cell line was analyzed for CFP and GFP expression by FACS and 63 compounds suppressed both promoters based on a z-score less than −1.0 (the average z-score of vehicle control is 2.00±1.04). Viability screening showed that most of chemicals showed toxicity to both CD133-positive and CD133-negative TICs ($R^2$=0.80) except a subgroup of chemicals which stood out with selective toxicity toward CD133-positive TICs (FIG. 7C). By merging the activity rankings of the tested chemicals in these screening methods, an optimally performing compound was identified: Inhibitor A (5Z,9α, 11α, 15R)-9,11, 15-Trihydroxy-17-phenyl-18,19,20-trinor-prost-5-en-1-oic acid, which is latanoprost acid. Indeed, Inhibitor A effectively blocked the NOTCH-TBC1D15 interaction, reduced HEY1 and NANOG promoter activities, and selectively killed CD133 positive TICs (FIG. 7C).

Figure 7D:
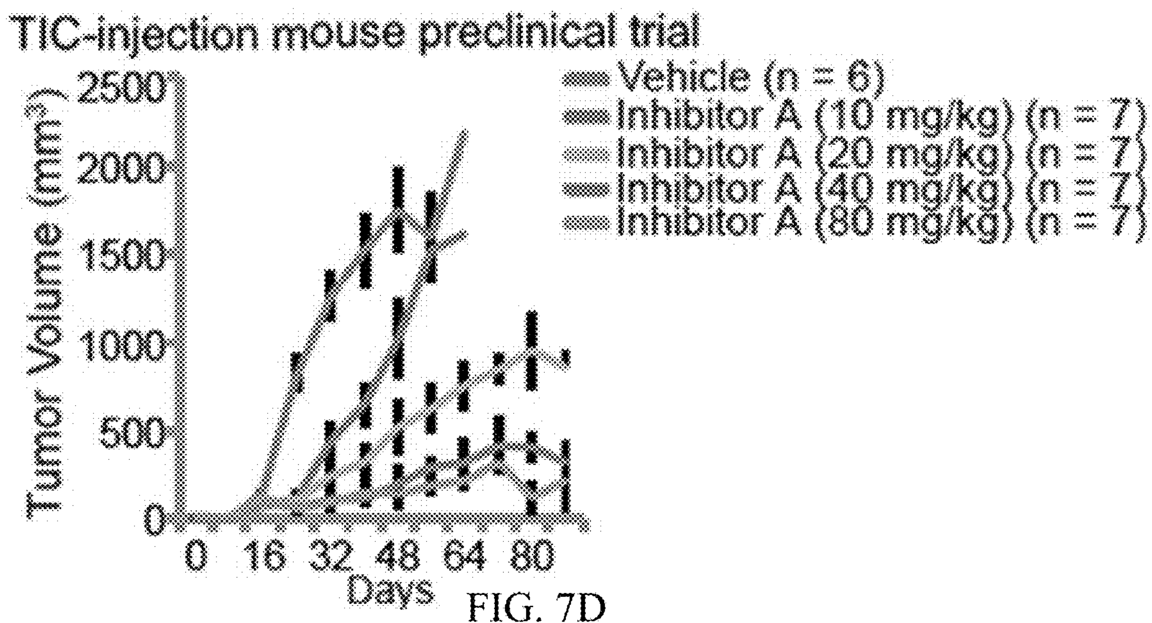
Figure 7E:
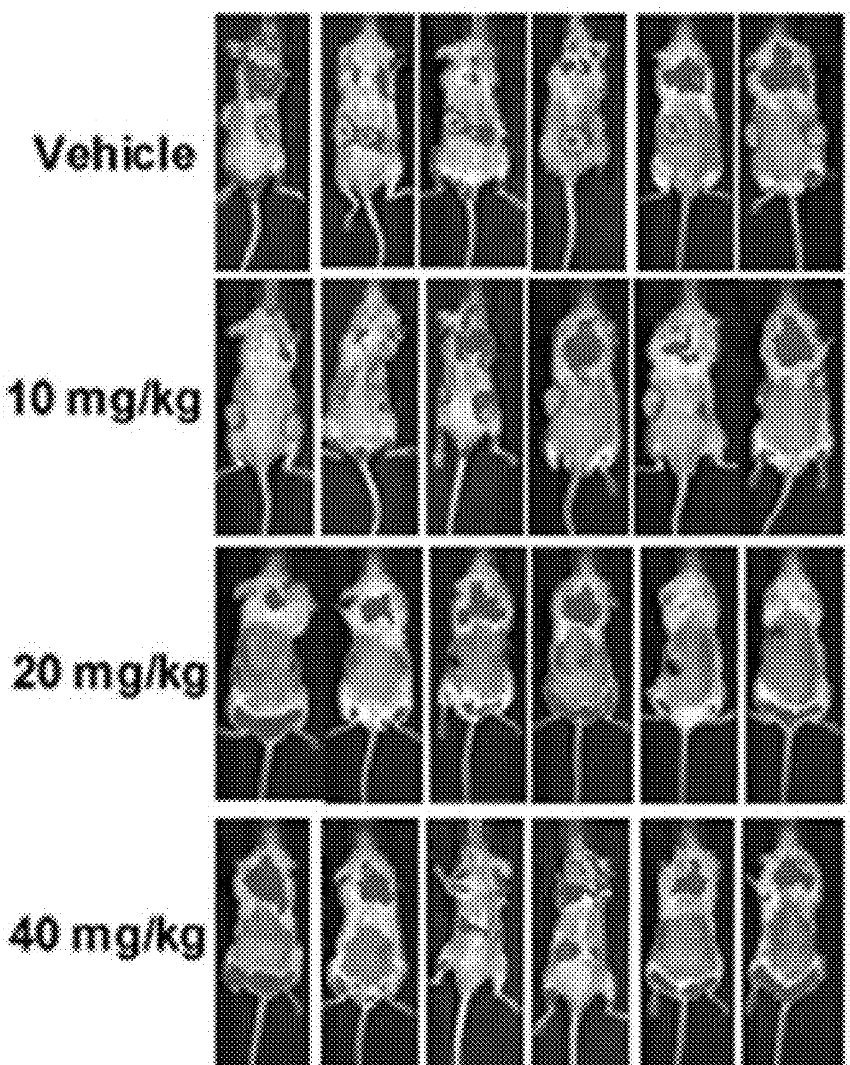

We tested the therapeutic efficacy of Inhibitor A in the patient-derived xenograft (PDX) model of HCC. The dose of 40 mg/kg given i.p. 5 times a week achieved a significant inhibition of tumor growth as monitored by red fluorescence dye (dsRed)-labeled TICs transplanted subcutaneously into NSG mice (FIGS. 7D, 7E). A separate pharmacokinetic study was conducted at three doses (10, 20, 40 mg/kg) administered i.p. into NSG mice to determine blood and tissue levels of the Inhibitor and tissue histology. From these studies, we assessed pharmacokinetic, toxicity, and efficacy data to select an optimal dosing scheme.

Figure 7F:
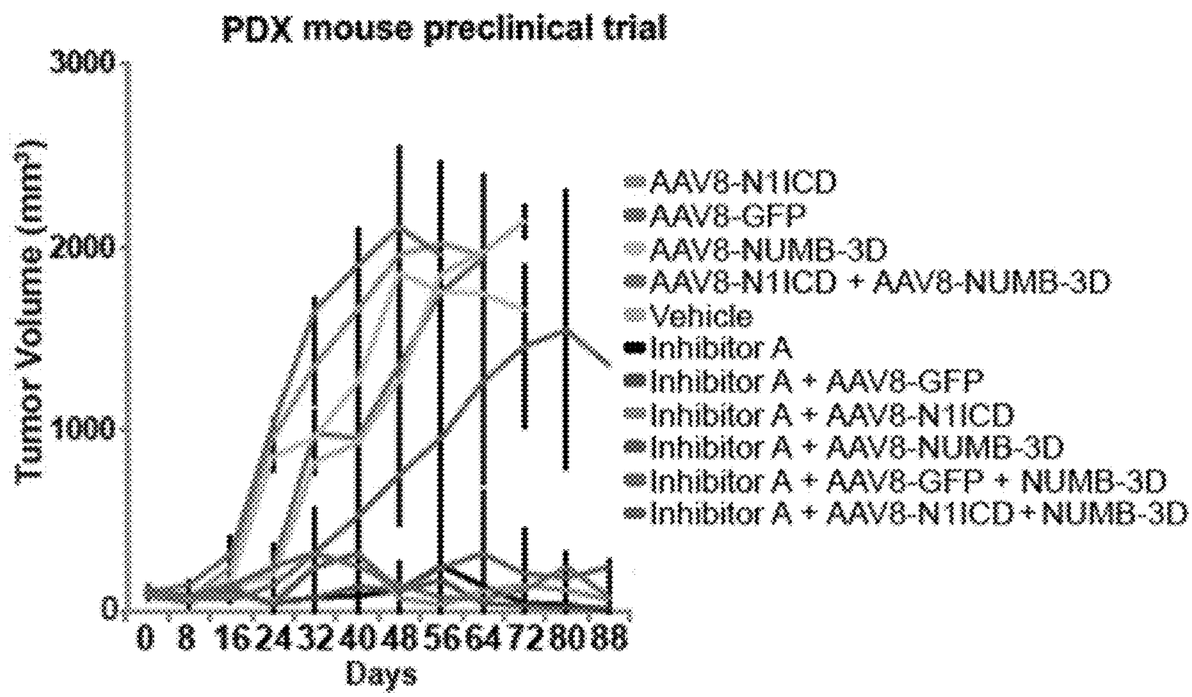
Figure 7G:
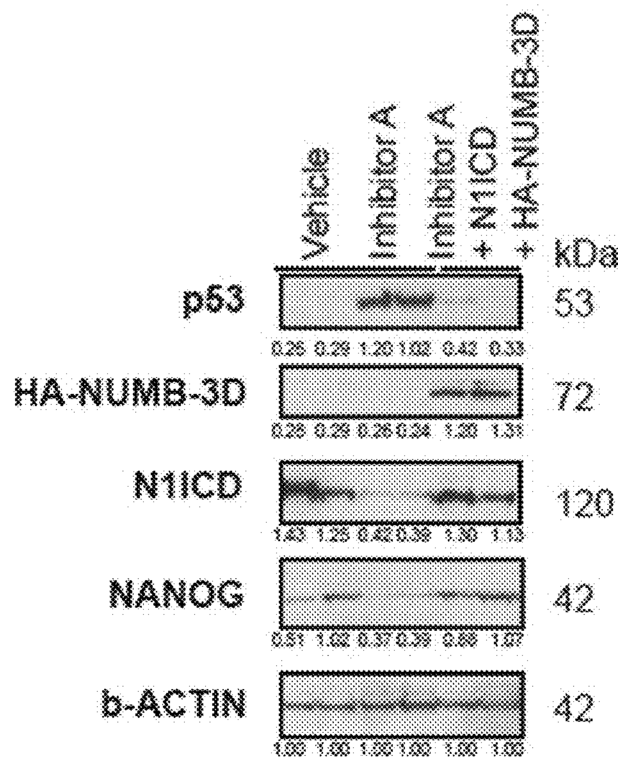

PDX mice were treated with the optimum dosing schedule. We monitored tumor sizes weekly three weeks post-transplantation for a total of 4 weeks (until the end of week 7). (If the tumor size reaches a diameter of ≥1.5 cm before 7 wk, we euthanized the mice per the IACUC guideline for tumor-bearing mice.) Our prior experience with the untreated HCC PDX model is 5-7 weeks are needed to generate tumors of the desired size (FIG. 7F). Experimental animals were euthanized at the end of the seven weeks study period and all tumor tissues were collected for histology for tumor characterization. Immunoblots were used to detect levels of for NANOG, TBC1D15, NICD, HES1 or HEY, CD133, p53, NUMB, and pS265-NUMB (FIG. 7G). Immunohistochemistry analysis was performed to monitor the expression of CD133, NANOG, p53, and Ki67.

Therapeutic Efficacy of Inhibitor A for TBC1D15-NICD Interaction

To test the therapeutic efficacy of the new inhibitor for its effect on TBC1D15-NICD interaction, we employed a true patient-derived xenograft (PDX) HCC model (FIG. 7F). We determined if newly identified small molecule inhibitors of the TBC1D15-NICD interaction would prevent tumor growth in the HCC PDX mouse model and specifically if this therapeutic effect was negatively affected by NICD expression, NUMB-3D expression, or the co-expression of NICD and NUMB-3D.

Aberrant NOTCH Signaling in Primary Hepatocyte is Sustained by TBC1D15 in Spite of FBW7 Expression To identify how TBC1D15 promotes the NOTCH pathway, we first determined the role of TBC1D15-NOTCH interaction in NOTCH/NICD stabilization: NUMB binds NOTCH/NICD at its C-terminal PEST domain to initiate NOTCH/NICD polyubiquitination and degradation. Our results show that TBC1D15 interacts with the same PEST and transactivation domains of NOTCH as NUMB, increases NICD level and Hes-1 promoter activity, the readout of NICD activity, generating a model that TBC1D15 interaction with NOTCH prevents NUMB-mediated NOTCH/NICD degradation and promotes NICD activity. We tested this model by performing site directed mutagenesis of the TBC1D15 interacting site of NICD and by using a putative small molecule inhibitor of this interaction.

To determine if TBC1D15 activates NOTCH, TBC1D15 knockdown increases full-length NOTCH1 level while reducing NOTCH1 intracellular domain (N1ICD), suggesting TBC1D15 also supports activation of NOTCH. We will test if TBC1D15 activates the degradation-resistant mutant of NOTCH1 (NOTCH1ΔPEST) and enhances recycling of NOTCH and its ligands via its inherent Rab7/11 GAP activity.

Effects of TBC1D15 on NUMB Phosphorylation and its Binding to the NICD PEST Domain To determine if TBC1D15 causes NUMB phosphorylation and its dissociation from the NICD PEST domain, we immunoprecipitated HA-N1ICD and/or endogenous N1ICD and immunoblot for NUMB and p-NUMB in both TIC TBC1D15 KD and hepatoblast TBC1D15 overexpression models. To test the causality of NUMB phosphorylation for dissociation from the PEST domain, we expressed the NUMB-3A mutant. This mutant carries S>A mutations to prevent phosphorylation at three critical Ser residues and may prevent TBC1D15-induced dissociation of NUMB from the PEST domain.

Effects of TBC1D15 on PEST Domain Phosphorylation, FBW7 Recruitment, and NICD Polyubiquitination Using the same cell models of TBC1D15 loss or gain of function approaches, the PEST domain phosphorylation which presumably signals for the ubiquitin ligase recruitment, was determined by immunoblot for phospho-Ser/Thr of HA-N1ICD precipitated by anti-HA. Anti-p-T2512 antibody were used. As the phosphorylation effect is observed, we tried to identify kinase(s) responsible for such phosphorylation regulated by TBC1D15 by in vitro kinase assays after immunoprecipitating potential kinases (CDK8, CDK3, CDK19, MEKK1, and aPKCζ) as previously described. We also overexpressed via lentivirus, potential recombinant kinases, kinase-dead mutants, or use shRNA targeting of candidate kinases vs. scrambled shRNA to determine their effects on the PEST domain phosphorylation. These results were correlated to changes in the PEST domain recruitment of FBW7, which is considered to be the major ubiquitin ligase for NICD. HA-N1ICD was precipitated and immunoblotted for presence of FBW7. Functional significance of the specific sites of PEST domain phosphorylation was determined from N1ICD mutants (S2490A, S2493A, S2500A, T2512A, S2514/2517A: dominant negative vs. T2512E or S2514/2517E: phosphomimetic) obtained in part from Prof. Jones (Salk Institute) and Dr. Del Sal (LNCIB, Italy) for their effects on FBW7 recruitment. Polyubiquitination of HA-N1ICD was determined by immunoblotting precipitated HA-N1CD with anti-ubiquitin antibody. To test the causality of FBW7, we knocked down this ligase in PIL4 hepatoblasts to determine if it stabilizes N1ICD.

Effects of the Small Molecule Inhibitors of TBC1D15-NICD Interaction

We tested our hypothesis by using the small molecule inhibitor of TBC1D15-NICD interaction we have discovered in TICs. This inhibitor would destabilize NICD via inhibition of TBC1D15 interaction with the PEST domain, and result in reciprocally increased NUMB binding to the PEST domain, thus leading to the PEST domain phosphorylation, FBW7 recruitment and polyubiquitination of NICD.

The TBC1D15 KD increased NUMB and FBW7 binding to the PEST domain of NICD leading to NICD polyubiquitination and degradation in TICs. For TBC1D15 expression, we used PIL4 hepatoblasts deficient in p53 as this cell model shows transformation upon this gain of function approach. This manipulation conversely reduced the same outcome parameters and promote NICD stability. As shown for TBC1D15-induced p53 degradation via NUMB phosphorylation, NUMB phosphorylation was causal for its loss of association with the PEST domain. The use of non-phosphorylatable NUMB-3A mutant helped determine if it prevents the ability of TBC1D15 to cause NUMB-3A dissociation from the PEST domain, recruitment of FBW7, and NICD degradation. It is possible that E3 ubiquitin ligases other than FBW7 may participate in NICD degradation. To determine the identity of the detected band(s) and the phosphorylated residues, we extracted proteins to tryptic digestion and mass-spectrometry. We acquired antibodies against phosphorylation-specific epitopes via commercial resources.

TBC1D15 KD increased NUMB and FBW7 binding to the PEST domain of NICD leading to NICD polyubiquitination and degradation in TICs. For TBC1D15 expression, we used PIL4 hepatoblasts deficient in p53 as this cell model shows transformation upon this gain of function approach. TBC1D15 expression in PIL4 hepatoblasts conversely reduce the same outcome parameters and promote NICD stability. NUMB phosphorylation was causal for its loss of association with the PEST domain through TBC1D15-induced p53 degradation via NUMB phosphorylation. Overexpression of non-phosphorylatable NUMB-3A mutant prevented the ability of TBC1D15 to cause NUMB-3A dissociation from the PEST domain, recruitment of FBW7, and NICD degradation. E3 ubiquitin ligases other than FBW7 contributed to NICD degradation. As FBW7 recruitment was not regulated by TBC1D15, which still stabilizes NICD, we tested other ubiquitin ligases such as c-Cbl. To determine the identity of the detected band(s) and the phosphorylated residues, we extracted proteins to tryptic digestion and mass-spectrometry. We developed and acquire antibodies against phosphorylation-specific epitopes via commercial resources. The use of anti-phospho-Ser/Thr antibody did not yield non-specific bands with high background.

TBC1D15 expression was associated with cleavage and activation of HA-N1ICDΔPEST, but not of the γ-secretase-resistant V1744K mutant while TBC1D15 KD has the reverse effects. This outcome led to the ensuring questions as to how TBC1D15 promotes the γ-secretase-dependent activation and whether this effect is mediated by the ability of TBC1D15 to more efficiently recruit ADAM-17 and γ-secretase. TBC1D15-stimulated recycling promoted surface expression of NOTCH receptors and ligands, elucidating TBC1D15-mediated NOTCH activation. TBC1D15 stimulated recycling of NOTCH1 and ligands. As this NUMB-mediated effect on NOTCH is shown to require the C-terminal PTB domain, we overexpressed the NUMBΔPTB mutant lacking the PTB domain to block the NUMB-driven NOTCH late endosome-lysosomal trafficking. This demonstrated whether this influences TBC1D15-mediated NOTCH recycling. If the TBC1D15's recycling effect is just a mere consequence of inhibition of NUMB trafficking, the mutant expression may shift the trafficking to the recycling pathway and abrogate the TBC1D15's stimulatory effect.

The both CSL sites of the Nanog gene were enriched by NICD in TICs and TBC1D15-expressing PIL4 cells by ChIP analysis and that these enrichments were attenuated in TBC1D15 KD TICs and control PIL4 cells. Newly generated reporter constructs to specifically address the functional cooperation of the respective CSL sites with the OCT4/SOX2 site, confirmed this functionality. Re-ChIP assay demonstrated NICD-OCT4/SOX2 interaction at the CSL and OCT4/SOX2 sites which are separated only by only 15 bp. A combination of ChIA-PET and ChIP-seq revealed the interaction between the enhancer CSL site and the OCT4/SOX2 site of the promoter. But these assays also revealed numerous chromatin interactions involving SCL/NICD sites on a genome-wide level. Although the current study only focused on the Nanog enhancer-promoter interaction, additional new information generated by these assays will allow us to explore global functions of NICD-mediated long-range chromatin interactions in the context of TIC biology. The proposed CRISPR/Cas9-mediated deletion of the CSL sites, abrogated NICD-mediated Nanog expression, self-renewal and tumorigenic activity of TICs. A deletion caused an unexpected phenotype if the CSL/NICD in either site has additional interacting partners besides OCT4/SOX2. We explored unexpected biological significance of the NICD in TICs. 3C or 4C analyses was performed in Alb-CreERT2; Tbc1d15$^{Flox/Flox}$ mice and WT mice injected with γ-Secretase or Inhibitor A to examine NOTCH's role for NANOG regulation.

TBC1D15 KD increased NUMB and FBW7 binding to the PEST domain of NICD leading to NICD polyubiquitination and degradation in TICs. For TBC1D15 expression, we used PIL4 hepatoblasts deficient in p53 as this cell model shows transformation upon this gain of function approach. TBC1D15 expression in PIL4 hepatoblasts conversely reduce the same outcome parameters and promote NICD stability. NUMB phosphorylation was causal for its loss of association with the PEST domain through TBC1D15-induced p53 degradation via NUMB phosphorylation. Overexpression of non-phosphorylatable NUMB-3A mutant prevented the ability of TBC1D15 to cause NUMB-3A dissociation from the PEST domain, recruitment of FBW7, and NICD degradation. E3 ubiquitin ligases other than FBW7 contributed to NICD degradation. As FBW7 recruitment was not regulated by TBC1D15, which still stabilizes NICD, we tested other ubiquitin ligases such as c-Cbl. To determine the identity of the detected band(s) and the phosphorylated residues, we extracted proteins to tryptic digestion and mass-spectrometry. We developed and acquire antibodies against phosphorylation-specific epitopes via commercial resources. The use of anti-phospho-Ser/Thr antibody did not yield non-specific bands with high background.

To identify how TBC1D15-activated NOTCH pathway contributes to TIC self-renewal and tumorigenesis, first we determined how NICD supports Nanog transcription. We have identified two previously uncharacterized CSL/RBPJ sites that are functionally important for Nanog transcription: one in a −5 kb upstream distal enhancer and another in a proximity to the critical OCT4/SOX2 element within the proximal promoter. We will test cooperative activities of these putative CSL/NICD sites with the OCT4/SOX2 element in TBC1D15-induced Nanog transcription by performing ChIP and re-ChIP assays and by using luciferase reporter constructs with deletions and site-specific mutations. To determine a long-range chromatin interaction between the distal enhancer CSL site with the promoter proximal OCT4/SOX2 element, we will perform parallel ChIP-seq and Chromatin Interaction Analysis by Capture-C analyses.

TBC1D15 expression was associated with cleavage and activation of HA-N1ICDΔPEST, but not of the γ-secretase-resistant V1744K mutant while TBC1D15 KD has the reverse effects. This outcome led to the ensuring questions as to how TBC1D15 promotes the γ-secretase-dependent activation and whether this effect is mediated by the ability of TBC1D15 to more efficiently recruit ADAM-17 and γ-secretase. TBC1D15-stimulated recycling promoted surface expression of NOTCH receptors and ligands, elucidating TBC1D15-mediated NOTCH activation. TBC1D15 stimulated recycling of NOTCH1 and ligands. As this NUMB-mediated effect on NOTCH is shown to require the C-terminal PTB domain, we overexpressed the NUMBΔPTB mutant lacking the PTB domain (McGill et al., *J Biol Chem* 278, 23196-23203, doi:10.1074/jbc.M302827200 (2003)) to block the NUMB-driven NOTCH late endosome-lysosomal trafficking. This demonstrated whether this influences TBC1D15-mediated NOTCH recycling. If the TBC1D15's recycling effect is just a mere consequence of inhibition of NUMB trafficking, the mutant expression may shift the trafficking to the recycling pathway and abrogate the TBC1D15's stimulatory effect.

The both CSL sites of the Nanog gene were enriched by NICD in TICs and TBC1D15-expressing PIL4 cells by ChIP analysis and that these enrichments were attenuated in TBC1D15 KD TICs and control PIL4 cells. Newly generated reporter constructs to specifically address the functional cooperation of the respective CSL sites with the OCT4/SOX2 site, confirmed this functionality. Re-ChIP assay demonstrated NICD-OCT4/SOX2 interaction at the CSL and OCT4/SOX2 sites which are separated only by only 15 bp. A combination of ChIA-PET and ChIP-seq revealed the interaction between the enhancer CSL site and the OCT4/SOX2 site of the promoter. But these assays also revealed numerous chromatin interactions involving SCL/NICD sites on a genome-wide level. Although the current study only focused on the Nanog enhancer-promoter interaction, additional new information generated by these assays allowed us to explore global functions of NICD-mediated long-range chromatin interactions in the context of TIC biology. The proposed CRISPR/Cas9-mediated deletion of the CSL sites, abrogated NICD-mediated Nanog expression, self-renewal and tumorigenic activity of TICs. A deletion caused an unexpected phenotype if the CSL/NICD in either site has additional interacting partners besides OCT4/SOX2. We explored unexpected biological significance of the NICD in TICs. 3C or 4C analyses was performed in Alb-CreERT2; Tbc1d15$^{Flox/Flox}$ mice and WT mice injected with γ-Secretase or Inhibitor A to examine NOTCH's role for NANOG regulation.

In Vivo Importance of the Putative Nanog CSL/NICD Sites in TIC-Mediated Tumorigenesis To determine the in vivo importance of the putative Nanog CSL/NICD sites in TIC-mediated tumorigenesis, we performed CRISPR/Cas9 gene editing to delete the CSL site in the Nanog distal enhancer vs. the promoter to determine their relative importance in TIC self-renewal and tumorigenic activity in orthotopically transplanted B6 mice fed alcohol diet.

Overall, our study indicated that TBC1D15 cooperates with the NOTCH pathway to support CD133 positive TIC tumorigenic activity and we tested that an inhibitor of this interaction is potentially therapeutic.

Our studies looked into NUMB isoform expression. Several recent studies have identified components of the splicing machinery involved in alternative splicing of human NUMB protein isoforms.

We highlight a relationship between TBC1D15, the phosphorylation of NUMB isoform 5, and the NOTCH1 signaling pathway. The Notch signaling pathway is a highly conserved developmental network that regulates a wide range of cellular functions in metazoans (multicellular organisms), including the determination of cell fate, survival, and proliferation. Abnormal activation of Notch signaling and upregulation of Notch target genes is implicated in many cancers. The cross-talk between the Notch and Numb signaling pathways results in the promotion of tumor growth and progression, and has been reported in several cancers.

We have defined the NOTCH phosphor-degron and demonstrated that the mutant forms of NOTCH1 PEST domain found in CD133-positive TICs cannot bind to the TBC1D15.

Inhibitor A suppressed interaction between TBC1D15 and NICD, which if left unchecked would promote HCC growth from the known etiologic backgrounds of alcoholism, obesity, and hepatitis. The NICD overexpression blocked the therapeutic effect of Inhibitor A thus demonstrating the competitive nature of this interaction. The therapeutic effect of Inhibitor A was associated with inhibition of TBC1D15-NICD interaction and MCD enrichments at the putative CSL sites of the NANOG gene. By contrast the N1ICD blockage resulted from abrogation of such inhibitions.

The stage of HCC from recruited patient materials will likely influence the chemoresistance and effectiveness of therapeutic agents. For this reason, histologic characterization of HCC plus clinical information on metastasis, etc. was carefully accounted and analyzed in the context of disease severity. Another influencing variable is prior chemotherapy of these patients as this tends to enrich for a CD133+ population. Thus an increased therapeutic efficacy against TBC1D15-NICD interaction is expected to be heightened in TICs. (For this reason, we saved fresh HCC samples for biochemical and immunohistochemical analysis.) An additional variable to be considered for tumor differences is the presence of mutations in NOTCH genes, which may influence the therapeutic inhibitor efficacy.

We conducted a pharmacokinetic study to assess the uptake of Inhibitor A by HCC tissues transplanted into NSG mice. The specific uptake by CD133+ cells, which we targeted, is a challenging tissue to address. In the proposed study, the causality of the TBC1D15-NOTCH mechanism will be tested in TIC orthotopic transplantation model and HCC PDX model but not in the whole animal model of liver tumorigenesis. But we are currently examining the liver tissues and CD133+ cells isolated from WT vs. TBC1D15 conditional KO HCV NS5A Tg mice fed with ethanol Western Diet, to determine if NOTCH activation is abrogated and NICD enrichments at the Nanog CSL sites are decreased to assess the relevance of our notion in this model.

The chemical and pharmacologic properties of the Inhibitor A are largely unknown, and it may have other effects besides interference of the TBCD1D15-NOTCH interaction. It is an analogue of prostaglandin F2α (e.g., carboprost or its analogue); and other inhibitors we have identified from the compound screening were also prostaglandin-related compounds. Our study focused on the new aspects of the TBCD1D15-NOTCH interaction, and any other biological effects of these inhibitors may also be studied.

Taken together, the results and clinical studies illustrate in detail the mechanisms underlying destabilization of the NUMB-p53 tumor suppressor complex and will lay the groundwork for new therapeutic strategies designed to restore function of this complex in tumor initiating cells, leading to improved clinical outcomes in alcoholic HCC patients.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as “open” terms (e.g., the term “including” should be interpreted as “including but not limited to,” the term “having” should be interpreted as “having at least,” the term “includes” should be interpreted as “includes but is not limited to,” etc.).

As used herein the term “comprising” or “comprises” is used in reference to compositions, methods, and respective component(s) thereof, that are useful to an embodiment, yet open to the inclusion of unspecified elements, whether useful or not. It will be understood by those within the art that, in general, terms used herein are generally intended as “open” terms (e.g., the term “including” should be interpreted as “including but not limited to,” the term “having” should be interpreted as “having at least,” the term “includes” should be interpreted as “includes but is not limited to,” etc.). Although the open-ended term “comprising,” as a synonym of terms such as including, containing, or having, is used herein to describe and claim the invention, the present invention, or embodiments thereof, may alternatively be described using alternative terms such as “consisting of” or “consisting essentially of.”

What is claimed is:

1. A method of treating a subject with a tumor or cancer, or suspected of having the tumor or cancer, comprising administering an effective amount of a composition comprising an inhibitor of Tre2-Bub2-Cdc16 domain family member 15 (TBC1D15) and a pharmaceutically acceptable excipient to the subject, wherein the inhibitor of TBC1D15 comprises latanoprost acid or latanoprost.

2. The method of claim 1, wherein the inhibitor of TBC1D15 inhibits the binding between TBC1D15 and NOTCH1.

3. The method of claim 1, wherein the inhibitor of TBC1D15 induces toxicity selectively to a $CD133^+$ tumor cell or a $CD133^+$ tumor-initiating stem-like cell (TIC) over a $CD133^-$ TIC or a normal cell, and/or wherein the inhibitor of TBC1D15 reduces gene expression of NOTCH and/or NANOG in a tumor cell or a TIC.

4. The method of claim 1, wherein the inhibitor of TBC1D15 blocks the binding between the TBC1D15 and a Ser-Thr-rich (STR) domain within a NOTCH-intracellular domain (NICD) of the NOTCH1, or wherein the inhibitor of TBC1D15 blocks the binding between the TBC1D15 and a PEST domain within the NICD of the NOTCH1.

5. The method of claim 1, wherein the inhibitor of TBC1D15 comprises latanoprost acid.

6. The method of claim 1, wherein the inhibitor of TBC1D15 comprises latanoprost.

7. The method of claim 1, wherein the subject is one detected with an increased expression level of TBC1D15 protein or gene in a tumor or cancerous sample, compared to that in a non-tumor and non-cancerous sample, or the increased expression level in a tissue of the subject suspected of having the tumor or cancer, compared to that in a matched tissue from a subject free of the tumor or cancer.

8. The method of claim 1, wherein the subject is one whose tumor or cancerous sample is positive for CD133 and CD49f, or one detected with a presence of $CD133^+$ and $CD49f^+$ TICs.

9. The method of claim 8, wherein prior to the administration, the subject has an increased phosphorylation of NUMB isoform 5 in $CD133^+$ TICs or $CD133^+$ tumor cells, compared to that in $CD133^-$ TICs or $CD133^-$ tumor cells; and/or wherein prior to the administration, has an increased number of mitochondria in $CD133^+$ TICs or $CD133^+$ tumor cells, compared to that in $CD133^-$ TICs or $CD133^-$ tumor cells.

10. The method of claim 1, wherein the effective amount of the composition comprises the inhibitor of TBC1D15 at 1-10, 10-20, 20-30, 30-40, 40-50, 50-60, 60-70, 70-80, 80-90, or 90-100 mg/kg of the subject administered intraperitoneally.

11. The method of claim 1, wherein the subject has a cancer comprising hepatocellular carcinoma, liver cancer, lung cancer, breast cancer, ovary cancer, or a combination thereof.

12. The method of claim 1, wherein the subject has hepatocellular carcinoma or a liver tumor, or wherein the subject has a liver disease comprising hepatitis B or hepatitis C.

13. The method of claim 1, further comprising detecting an increased p53 protein level expression, a decreased NOTCH1 expression level, a decreased NANOG expression level, or a combination thereof in a tumor sample of the subject following the administration, compared to respective level before the administration.

* * * * *

SEQUENCE LISTING

```
<160> NUMBER OF SEQ ID NOS: 12

<210> SEQ ID NO 1
<211> LENGTH: 30
<212> TYPE: PRT
```

```
<213> ORGANISM: Artificial Sequence
<220> FEATURE:
<223> OTHER INFORMATION: NOTCH1 aa.2488-2517

<400> SEQUENCE: 1

Gln His Ser Tyr Ser Ser Pro Val Asp Asn Thr Pro Ser His Gln Leu
1               5                   10                  15

Gln Val Pro Glu His Pro Phe Leu Thr Pro Ser Pro Glu Ser
            20                  25                  30


<210> SEQ ID NO 2
<211> LENGTH: 7
<212> TYPE: PRT
<213> ORGANISM: Artificial Sequence
<220> FEATURE:
<223> OTHER INFORMATION: synthetic contruct

<400> SEQUENCE: 2

Phe Leu Thr Pro Ser Pro Glu
1               5


<210> SEQ ID NO 3
<211> LENGTH: 7
<212> TYPE: PRT
<213> ORGANISM: Artificial Sequence
<220> FEATURE:
<223> OTHER INFORMATION: synthetic contruct

<400> SEQUENCE: 3

Leu Pro Thr Pro Ser Leu Ser
1               5


<210> SEQ ID NO 4
<211> LENGTH: 7
<212> TYPE: PRT
<213> ORGANISM: Artificial Sequence
<220> FEATURE:
<223> OTHER INFORMATION: synthetic contruct

<400> SEQUENCE: 4

Gly Glu Thr Pro Ser Leu Ser
1               5


<210> SEQ ID NO 5
<211> LENGTH: 7
<212> TYPE: PRT
<213> ORGANISM: Artificial Sequence
<220> FEATURE:
<223> OTHER INFORMATION: synthetic contruct

<400> SEQUENCE: 5

Leu Leu Thr Pro Ser Gln Ser
1               5


<210> SEQ ID NO 6
<211> LENGTH: 30
<212> TYPE: PRT
<213> ORGANISM: Artificial Sequence
<220> FEATURE:
<223> OTHER INFORMATION: synthetic contruct

<400> SEQUENCE: 6

Ser Pro Gln Leu His Gly Ala Pro Leu Gly Gly Thr Pro Thr Leu Ser
1               5                   10                  15

Pro Pro Leu Cys Ser Pro Asn Gly Tyr Leu Gly Ser Leu Lys
            20                  25                  30
```

<210> SEQ ID NO 7
<211> LENGTH: 30
<212> TYPE: PRT
<213> ORGANISM: Artificial Sequence
<220> FEATURE:
<223> OTHER INFORMATION: synthetic contruct

<400> SEQUENCE: 7

```
Ser Pro Gln Leu His Gly Ala Pro Leu Gly Gly Thr Pro Thr Leu Ser
1               5                   10                  15

Pro Pro Leu Cys Ser Pro Asn Gly Ala Leu Gly Ser Leu Lys
            20                  25                  30
```

<210> SEQ ID NO 8
<211> LENGTH: 22
<212> TYPE: PRT
<213> ORGANISM: Artificial Sequence
<220> FEATURE:
<223> OTHER INFORMATION: synthetic contruct

<400> SEQUENCE: 8

```
Leu Ser Pro Pro Leu Cys Ser Pro Asn Gly Tyr Leu Gly Ser Leu Lys
1               5                   10                  15

Pro Gly Val Gln Gly Lys
            20
```

<210> SEQ ID NO 9
<211> LENGTH: 22
<212> TYPE: PRT
<213> ORGANISM: Artificial Sequence
<220> FEATURE:
<223> OTHER INFORMATION: synthetic contruct

<400> SEQUENCE: 9

```
Leu Ser Pro Pro Leu Cys Ser Pro Asn Gly Ala Leu Gly Ser Leu Lys
1               5                   10                  15

Pro Gly Val Gln Gly Lys
            20
```

<210> SEQ ID NO 10
<211> LENGTH: 30
<212> TYPE: PRT
<213> ORGANISM: Artificial Sequence
<220> FEATURE:
<223> OTHER INFORMATION: synthetic contruct

<400> SEQUENCE: 10

```
Gln His Ser Ala Ser Ser Pro Val Asp Asn Thr Pro Ser His Gln Leu
1               5                   10                  15

Gln Val Pro Glu His Pro Phe Leu Thr Pro Ser Pro Glu Ser
            20                  25                  30
```

<210> SEQ ID NO 11
<211> LENGTH: 30
<212> TYPE: PRT
<213> ORGANISM: Artificial Sequence
<220> FEATURE:
<223> OTHER INFORMATION: synthetic contruct

<400> SEQUENCE: 11

```
Glu Glu Thr Pro Leu Phe Leu Ala Ala Arg Glu Gly Ser Tyr Glu Thr
1               5                   10                  15

Ala Lys Val Leu Leu Asp His Phe Ala Asn Arg Asp Ile Thr
```

```
            20                  25                  30


<210> SEQ ID NO 12
<211> LENGTH: 30
<212> TYPE: PRT
<213> ORGANISM: Artificial Sequence
<220> FEATURE:
<223> OTHER INFORMATION: synthetic contruct

<400> SEQUENCE: 12

Glu Glu Thr Pro Leu Phe Leu Ala Ala Arg Glu Gly Ser Ala Glu Thr
1               5                   10                  15

Ala Lys Val Leu Leu Asp His Phe Ala Asn Arg Asp Ile Thr
            20                  25                  30
```